United States Patent
Van Ginderachter et al.

(10) Patent No.: US 9,556,273 B2
(45) Date of Patent: *Jan. 31, 2017

(54) ANTI-MACROPHAGE MANNOSE RECEPTOR SINGLE VARIABLE DOMAINS FOR TARGETING AND IN VIVO IMAGING OF TUMOR-ASSOCIATED MACROPHAGES

(71) Applicants: VIB VZW, Ghent (BE); Vrije Universiteit Brussel, Brussels (BE)

(72) Inventors: Jo Van Ginderachter, Ninove (BE); Patrick De Baetselier, Berchem (BE); Nick Devoogdt, Zemst (BE); Tony Lahoutte, Ganshoren (BE); Damya Laoui, Limal (BE); Kiavash Movahedi, Frankfurt am Main (DE); Geert Raes, Sint-Genesius-Rode (BE); Steve Schoonooghe, Kessel-Lo (BE)

(73) Assignees: VIB VZW, Ghent (BE); Vrije Universiteit Brussel, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/402,301

(22) PCT Filed: Mar. 15, 2013

(86) PCT No.: PCT/EP2013/055427
§ 371 (c)(1),
(2) Date: Nov. 19, 2014

(87) PCT Pub. No.: WO2013/174537
PCT Pub. Date: Nov. 28, 2013

(65) Prior Publication Data
US 2015/0093336 A1    Apr. 2, 2015

Related U.S. Application Data

(63) Continuation-in-part of application No. 13/480,350, filed on May 24, 2012, now Pat. No. 9,101,674, which is a continuation-in-part of application No. 13/065,794, filed on Mar. 29, 2011, now abandoned.

(60) Provisional application No. 61/341,356, filed on Mar. 29, 2010.

(51) Int. Cl.
| | |
|---|---|
| *C07K 16/28* | (2006.01) |
| *A61K 51/10* | (2006.01) |
| *A61K 47/48* | (2006.01) |
| *B82Y 5/00* | (2011.01) |

(52) U.S. Cl.
CPC ..... *C07K 16/2851* (2013.01); *A61K 47/48484* (2013.01); *A61K 47/48561* (2013.01); *A61K 47/48761* (2013.01); *A61K 51/1027* (2013.01); *A61K 51/1096* (2013.01); *B82Y 5/00* (2013.01); *C07K 2317/22* (2013.01); *C07K 2317/35* (2013.01); *C07K 2317/569* (2013.01)

(58) Field of Classification Search
CPC ............... C07K 16/2851; A61K 47/48484; A61K 47/48561; A61K 47/48761; A61K 51/1027; A61K 51/1045–51/1072; A61K 51/1096
See application file for complete search history.

(56) References Cited

U.S. PATENT DOCUMENTS

| | | | | |
|---|---|---|---|---|
| 6,818,749 B1 * | 11/2004 | Kashmiri | ........... | A61K 49/0002 424/130.1 |
| 8,906,680 B2 * | 12/2014 | Blanchetot | ............. | C07K 16/24 435/326 |
| 8,907,065 B2 * | 12/2014 | Hermans | ............ | C07K 16/2818 424/130.1 |
| 9,101,674 B2 * | 8/2015 | Movahedi | ........ | A61K 47/48484 |
| 2010/0070191 A1 | 3/2010 | Gold et al. | | |
| 2011/0262348 A1 | 10/2011 | Movahedi et al. | | |
| 2012/0301394 A1 | 11/2012 | Movahedi et al. | | |
| 2015/0335770 A1 * | 11/2015 | Movahedi | ........ | A61K 47/48484 424/1.49 |
| 2016/0024213 A1 * | 1/2016 | De Baetselier | .... | C07K 16/2851 424/1.49 |

FOREIGN PATENT DOCUMENTS

| | | |
|---|---|---|
| EP | 1134231 B1 * | 4/2009 |
| WO | 9404678 A1 | 3/1994 |
| WO | 9425591 A1 | 11/1994 |
| WO | 9504079 A1 | 2/1995 |
| WO | 9634103 A1 | 10/1996 |
| WO | 9749805 A2 | 12/1997 |
| WO | 9937681 A2 | 7/1999 |
| WO | 0040968 A1 | 7/2000 |
| WO | 0043507 A1 | 7/2000 |
| WO | 0065057 A1 | 11/2000 |
| WO | 0121817 A1 | 3/2001 |
| WO | 0140310 A2 | 6/2001 |
| WO | 0144301 A1 | 6/2001 |
| WO | 0190190 A2 | 11/2001 |
| WO | 0248193 A2 | 6/2002 |
| WO | 02085945 A2 | 10/2002 |
| WO | 03025020 A1 | 3/2003 |
| WO | 03035694 A2 | 5/2003 |
| WO | 03054016 A2 | 7/2003 |
| WO | 03055527 A2 | 7/2003 |

(Continued)

OTHER PUBLICATIONS

Laoui et al., Immunobiol. 2011; 216:1192-1202.*

(Continued)

*Primary Examiner* — Jessica H Roark
(74) *Attorney, Agent, or Firm* — TraskBritt, P.C.

(57) ABSTRACT

The disclosure relates to immunoglobulin single variable domains directed against human macrophage mannose receptor (MMR) and their uses in the field of oncology. More specifically, it concerns immunoglobulin single variable domains, including single-domain antibodies (sdAbs), against human MMR and their use in targeting and in vivo imaging of tumor-associated macrophages, with applications in the field of cancer diagnostics and therapeutics and monitoring of the disease.

21 Claims, 6 Drawing Sheets

(56) References Cited

FOREIGN PATENT DOCUMENTS

| WO | 2004041862 A2 | 5/2004 |
|---|---|---|
| WO | 2004041863 A2 | 5/2004 |
| WO | 2004041865 A2 | 5/2004 |
| WO | 2004041867 A2 | 5/2004 |
| WO | 2004049794 A2 | 6/2004 |
| WO | 2004060965 A2 | 7/2004 |
| WO | 2004062551 A2 | 7/2004 |
| WO | 2005044858 A1 | 5/2005 |
| WO | 2006079372 A1 | 8/2006 |
| WO | 2006122786 A2 | 11/2006 |
| WO | 2006122787 A1 | 11/2006 |
| WO | 2006122825 A2 | 11/2006 |
| WO | 2008020079 A1 | 2/2008 |
| WO | 2012131078 A1 | 10/2012 |
| WO | 2013130381 A1 | 9/2013 |
| WO | 2013174537 A1 | 11/2013 |

OTHER PUBLICATIONS

Almagro & Fransson, Frontiers in Bioscience 2008; 13:1619-33.*
De Genst et al., Dev Comp Immunol 2006; 30:187-98.*
MacCallum et al., J Mol Biol. 1996; 262:732-745.*
Brown et al., J. Immunol. 1996; 156(9):3285-91.*
Bartolazzi et al., The Lancet 2008; 9:543-49.*
HogenEsch et al. J. Controlled Release 2012; 164:183-186.*
Tang et al. Cancer Letters 2016; 370:85-90.*
Vitetta & Ghetie, Science 2006; 313:308-309.*
Pearson H., Nature Mar. 17, 2006, Tragic Drug Trial Spotlights Potent Molecule, Nature News.*
Aspeslagh et al., Eur. J. Cancer 2016; 52:50-66.*
Sanmamed et al., Sem. Oncol. 2015; 24:640-655.*
Chakravarty et al., Theranostics 2014; 4(4):386-398.*
Dangaj et al., Mannose Receptor (MR) Engagement by Mesothelin GPI Anchor Polarizes Tumor-Associated Macrophages and is Blocked by Anti-MR Human Recombinant Antibody, PLOS ONE, Dec. 1, 2011, pp. e-28386-1, vol. 6, No. 12, Public Library of Science, US.
Kang et al, The human macrophage mannose receptor directs *Mycobacterium tuberculosis* lipoarabinomannan-mediated phagosome biogenesis, Journal of Experimental Medicine, Oct. 3, 2005, pp. 987-999, vol. 202, No. 7.
Rudikoff et al., Single amino acid substitution altering antigen-binding specificity, Proceedings of the National Academy of Sciences, Mar. 1, 1982, pp. 1979-1983, vol. 79, National Academy of Sciences, US.
PCT International Search Report, PCT/EP2013/055427, dated Nov. 6, 2013.
Gottlin et al., Isolation of Novel EGFR-Specific VHH Domains, J Biomol Screen, 2009, pp. 77-85, vol. 14.
Cortez-Retamozo et al., Efficient Cancer Therapy with a Nanobody-Based Conjugate, Cancer Res., 2004, pp. 2853-2857, vol. 64.
Harmsen et al., Properties, production, and applications of camelid single-domain antibody fragments. Appl. Microbial. Biotechnol. 77:13-22, 2007.
Heusinkveld M, van der Burg SH. Identification and manipulation of tumor associated macrophages in human cancers. Journal of Translational Medicine. 2011; 9:216.
Algars A, Irjala H, Vaittinen S, Huhtinen H, Sundstrom J, Salmi M, et al. Type and location of tumor-infiltrating macrophages and lymphatic vessels predict survival of colorectal cancer patients. Int J Cancer 2012; 131:864.

* cited by examiner

A.

C.

B.

US 9,556,273 B2

ANTI-MACROPHAGE MANNOSE RECEPTOR SINGLE VARIABLE DOMAINS FOR TARGETING AND IN VIVO IMAGING OF TUMOR-ASSOCIATED MACROPHAGES

CROSS-REFERENCE TO RELATED APPLICATIONS

This application is a national phase entry under 35 U.S.C. §371 of International Patent Application PCT/EP2013/055427, filed Mar. 15, 2013, designating the United States of America and published in English as International Patent Publication WO 2013/174537 A1 on Nov. 28, 2013, which claims the benefit under Article 8 of the Patent Cooperation Treaty and as a continuation-in-part to U.S. patent application Ser. No. 13/480,350, filed May 24, 2012.

STATEMENT ACCORDING TO 37 C.F.R. §1.821(c) or (e)-SEQUENCE LISTING SUBMITTED AS TXT AND PDF FILES

Pursuant to 37 C.F.R. §1.821(c) or (e), a file containing a TXT version and a PDF version of the Sequence Listing have been submitted concomitant with this application, the contents of which are hereby incorporated by reference.

TECHNICAL FIELD

The disclosure relates to immunoglobulin single variable domains directed against human macrophage mannose receptor (MMR) and their uses in the field of oncology. More specifically, it concerns immunoglobulin single variable domains, including single-domain antibodies (sdAbs) (or NANOBODIES® from Ablynx, Gent, Belgium), against human MMR and their use in targeting and in vivo imaging of tumor-associated macrophages, with applications in the field of cancer diagnostics and therapeutics and monitoring of the disease.

BACKGROUND

Non-invasive molecular imaging is a powerful technique aimed at tracking cellular and molecular events in their native environment in the intact living subject. In its broadest sense, molecular imaging entails the administration of a tracer molecule labeled with a contrast reagent for visualization. Primarily, radioactively labeled tracers are used in combination with positron-emission tomography (PET) or single photon emission-computed tomography (SPECT)-based imaging techniques (Pysz et al. 2010, Clin. Radiol. 65:500-16). In the clinic, the majority of cancer imaging is currently still performed based on detection of enhanced metabolism in cancer cells using $^{18}F$ radiolabeled deoxyglucose (Coenen et al. 2010, Nucl. Med. Biol. 37:727-40), while $^{99m}Tc$-labeled human serum albumin is used for lymphoscintigraphic mapping of the draining lymph nodes in cancer (Kim et al. 2001, Int. J. Oncol. 19:991-6). Although useful, these tracers do not target a specific molecule or receptor on the surface of the cells involved in the disease process. Therefore, there is a need for probes that allow a more specific molecular characterization of inflamed or diseased tissue using disease related membrane antigens. These specific markers can help to define the phenotype of a disease and can be targeted by specific agents like monoclonal antibodies (MAbs). In this context, the choice of the targeted molecular markers will be a critical factor in determining whether it is possible to acquire in-depth molecular information on the underlying disease process.

Several FDA approved MAbs directed against tumor-associated antigens (TAAs) on malignant cells are being applied for diagnosis and treatment of cancer, with a few of the most commonly used MAbs being human epidermal growth factor receptor 2 (HER2)-specific Trastuzumab (Dijkers et al. 2010, Clin. Pharmacol. Ther. 87:586-92), carcinoembryonic antigen (CEA)-specific Arcitumomab (Hong et al. 2008, Biomark Insights 3:435-451) and prostate-specific membrane antigen (PSMA)-specific Capromab (Aparici et al. 2012, Am. Nucl. Med. Mol. Imaging 2:48-54). Yet, although the direct targeting of antibody moieties to TAAs on malignant cells is a potent tool that has reached clinical maturity, the non-transformed cells present within the tumor microenvironment can also provide useful biomarkers for molecular imaging, as an alternative or complement to markers on the inherently genetically instable transformed cells. Indeed, tumors should be considered as organ-like structures featuring a complex bidirectional interplay between transformed (cancer) and non-transformed (stromal) cells, whereby stromal cells can critically contribute to tumor initiation, growth and metastasis. Hence, targeting these tumor-associated stroma cells for imaging could provide additional information on the state of the tumor or response to therapy.

In particular, tumor-associated macrophages (TAMs) are an important component of the tumor stroma, both in murine models and human patients (Pollard 2004, Nat. Rev. Cancer 4:71-8). TAMs can promote tumor-growth by affecting angiogenesis, immune suppression and invasion and metastasis (Lin et al. 2006, Cancer Res. 66:11238-46). The plasticity of macrophages offers perspectives for using them as in vivo sensors for the tumor microenvironment they are exposed to. As a matter of fact, at the tumor site, these cells are confronted with different tumor microenvironments, leading to different TAM subsets with specialized functions and distinct molecular profiles (Laoui et al. 2011, Int. J. Dev. Biol. 55:861-867). For example, in mammary tumors, at least two distinct TAM subpopulations have been described, based on a differential expression of markers such as the macrophage mannose receptor (MMR or MHC II), differences in pro-angiogenic or immunosuppressive properties and intratumoral localization (normoxic/perivascular tumor areas versus hypoxic regions). In particular, the association of MMR-high TAMs with hypoxic regions in the tumor (Movahedi et al. 2010, Cancer Res. 70:5728-5739) offers perspectives for image-guided radiotherapy.

Full-sized MAbs have a number of disadvantages that have so far limited their effective use in the clinic. MAbs are macromolecules with a relatively poor penetration into solid and isolated tissues such as tumors (Hughes et al. 2000, J. Clin. Oncol. 18:363-370). In addition, complete MAbs feature a long residence time in the body and a potential increase in background signals because of binding to Fc receptors on non-target cells, making them less suitable for molecular imaging applications. Indeed, for imaging the most important properties of a tracer are: rapid interaction with the target, fast clearing of unbound molecules from the body and low non-specific accumulation, especially around the area of interest. These requirements have led to the development of a myriad of antibody derived probe formats, like Fabs and scFvs, trying to combine specificity with a small size for favorable pharmacokinetics (Kaur et al. 2012, Cancer Lett. 315:97-111).

A novel approach for generating small and high-affinity antigen-binding moieties focuses on the use of single-domain VHH antibody fragments, named NANOBODIES®, derived from the heavy-chain only antibodies found in camelid species (Hamers-Casterman et al. 2003, *Nature* 363:446-448). sdAbs, conveniently labeled with $^{99m}$Tc at their carboxy-terminal hexahistidine-tail, have by now a solid track record for SPECT-based molecular imaging in preclinical animal models (reviewed in: Vaneycken et al. 2011, *Curr. Opin. Biotechnol.* 22:877-881), with rapid blood clearance of unbound probes and high signal-to-noise ratios as early as a few hours after inoculation. In particular, US2011/0262348 demonstrates the usefulness of $^{99m}$Tc-labeled mouse-specific anti-MMR sdAbs for targeting MMR-positive TAMs in mice models that spontaneously develop carcinomas. These results offer perspectives for applications of anti-MMR sdAbs in image-guided radiotherapy, whereby the distribution of radiation is adapted in function of localized risk factors such as hypoxia (Bentzen 2005, *Lancet Oncol.* 6:112-117). Moreover, as has been documented for sdAbs targeting the HER2 tumor antigen, sdAbs exhibiting effective tumor targeting can be converted from an imaging probe in a radioimmunotherapeutic compound by coupling it to a therapeutic radionuclide (D'Huyvetter et al. 2012, *Contrast Media Mol. Imaging* 7:254-264).

However, there is still a need for specific probes that can be used both in the clinic and in preclinical animal models, with applications including improved diagnosis, prognosis, treatment and therapy monitoring.

BRIEF SUMMARY

It has been found that MMR-positive TAMs can be detected in intratumoral hypoxic zones of human samples, as illustrated in human breast cancer samples, demonstrating the clinical relevance of targeting MMR-positive TAM subpopulations in the tumor stroma. Therefore, immunoglobulin single variable domains, in particular, sdAbs, were generated that specifically recognize human MMR. Several of these sdAbs were found to be cross-reactive with mouse MMR, which is of advantage for diagnostic and/or therapeutic development, since it allows the same immunoglobulin single variable domain to be tested in pre-clinical disease models as well as in clinical settings.

The disclosure thus provides for immunoglobulin single variable domains, including sdAbs, directed against the human macrophage mannose receptor, and their usefulness for selective in vivo targeting and imaging of MMR-positive TAM subpopulations in the tumor stroma. Evidence is provided that MMR-positive TAMs can be efficiently targeted in vivo using these anti-MMR immunoglobulin single variable domains in preclinical animal models, as illustrated in murine models.

Accordingly, a first aspect of the disclosure relates to an immunoglobulin single variable domain that is directed against and/or that specifically binds to human macrophage mannose receptor (SEQ ID NO: 1), wherein the immunoglobulin single variable domain comprises an amino acid sequence that comprises four framework regions (FR) and three complementarity-determining regions (CDR) according to the following formula (1):

FR1-CDR1-FR2-CDR2-FR3-CDR3-FR4 (1);

and wherein CDR1 is chosen from the group consisting of:
a. SEQ ID NOs: 67-96,
b. Polypeptides that have at least 80% amino acid identity with SEQ ID NOs: 67-96,
c. Polypeptides that have 1, 2 or 3 amino acid difference with SEQ ID NOs: 67-96, and wherein CDR2 is chosen from the group consisting of:
a. SEQ ID NOs: 127-156,
b. Polypeptides that have at least 80% amino acid identity with SEQ ID NOs: 127-156,
c. Polypeptides that have 1, 2 or 3 amino acid difference with SEQ ID NOs: 127-156, and wherein CDR3 is chosen from the group consisting of:
a. SEQ ID NOs: 187-216,
b. Polypeptides that have at least 80% amino acid identity with SEQ ID NOs: 187-216,
c. Polypeptides that have 1, 2 or 3 amino acid difference with SEQ ID NOs: 187-216.

In one embodiment, immunoglobulin single variable domains are provided as described above wherein the framework regions (FRs) have an amino acid sequence identity of more than 80% with the FRs of SEQ ID NOs: 37-66 (FR1), SEQ ID NOs: 97-126 (FR2), SEQ ID NOs: 157-186 (FR3), SEQ ID NOs: 217-246 (FR4).

More specifically, the disclosure envisages immunoglobulin single variable domains comprising an amino acid sequence chosen from the group of SEQ ID NOs: 7-36 or polypeptides that have at least 80% amino acid identity with SEQ ID NOs: 7-36. According to a preferred embodiment, the immunoglobulin single variable domain is a single-domain antibody (sdAb) chosen from SEQ ID NOs: 7, 8, 9 and 10.

It is particularly envisaged that the immunoglobulin single variable domains as described above are fused to a detectable label, such as a radionuclide. The immunoglobulin single variable domain as described above may also be fused to a functional moiety, preferably a therapeutically active agent.

Also encompassed are polypeptides comprising one or more of any of the above-described immunoglobulin single variable domains, as well as nucleic acids encoding an immunoglobulin single variable domain or a polypeptide as described above.

According to another aspect, the disclosure also relates to a pharmaceutical composition comprising an immunoglobulin single variable domain as described above, or a polypeptide as described above, and optionally at least one of a pharmaceutically acceptable carrier, adjuvant or diluent.

Further aspects of the disclosure relate to an immunoglobulin single variable domain as described above or a polypeptide as described above for use as contrast agent in non-invasive in vivo medical imaging; for use in diagnosis, prognosis and/or treatment of cancer; for use in monitoring the efficacy of cancer therapy. The immunoglobulin single variable domains and the uses as described are based on the characteristic that these immunoglobulin single variable domains specifically target MMR-positive tumor-associated macrophages (TAMs) inside a tumor.

Also envisaged is a method for producing an immunoglobulin single variable domain as described above or a polypeptide as described above, the method comprising the steps of:
expressing, in a suitable host cell or a suitable expression system, a nucleic acid sequence encoding an immunoglobulin single variable domain or a polypeptide as described above; and optionally
isolating and/or purifying the immunoglobulin single variable domain or the polypeptide.

Objects of the disclosure will be clear from the description that follows.

DETAILED DESCRIPTION

Figure 1:
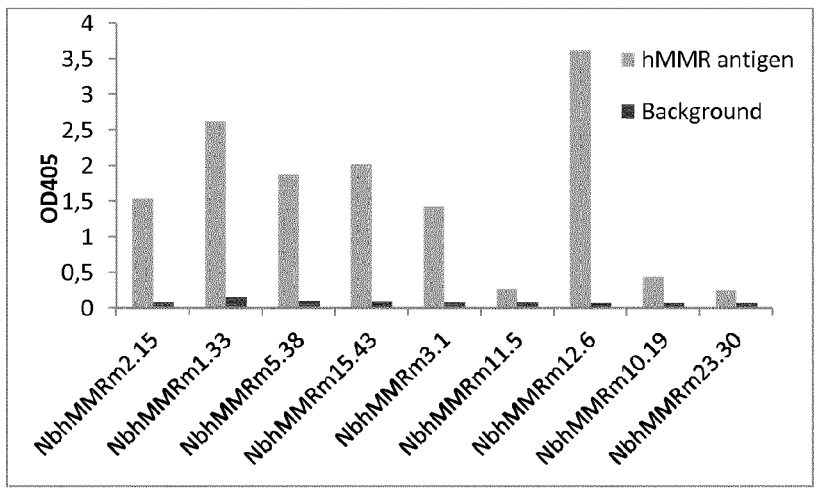
FIG. 1: PE-ELISA on human MMR. Summary of the selected anti-human MMR Nb clones. A clone was selected when the OD 405 nm was at least three times higher on specific antigen as compared to irrelevant milk-blocking proteins.

The disclosure will be described with respect to particular embodiments and with reference to certain drawings but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated. Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

Unless otherwise defined herein, scientific and technical terms and phrases used in connection with the disclosure shall have the meanings that are commonly understood by those of ordinary skill in the art. Generally, nomenclatures used in connection with, and techniques of molecular and cellular biology, structural biology, biophysics, pharmacology, genetics and protein and nucleic acid chemistry described herein are those well-known and commonly used in the art. The methods and techniques of the disclosure are generally performed according to conventional methods well known in the art and as described in various general and more specific references that are cited and discussed throughout the present specification unless otherwise indicated. See, for example, Sambrook et al. (2001), *Molecular Cloning: A Laboratory Manual,* 3rd ed., Cold Spring Harbor Laboratory Press, Cold Spring Harbor, N.Y.; Ausubel et al. (1992), *Current Protocols in Molecular Biology,* Greene Publishing Associates (and Supplements to 2002); Rup (2009), *Biomolecular Crystallography: Principles, Practice*

*and Applications to Structural Biology,* 1st edition, Garland Science, Taylor & Francis Group, LLC, an informa Business, N.Y.; Limbird (2004), *Cell Surface Receptors,* 3d ed., Springer.

As used herein, the terms "polypeptide," "protein," and "peptide" are used interchangeably herein, and refer to a polymeric form of amino acids of any length, which can include coded and non-coded amino acids, chemically or biochemically modified or derivatized amino acids, and polypeptides having modified peptide backbones.

As used herein, the terms "nucleic acid molecule," "polynucleotide," "polynucleic acid," and "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "sequence identity," as used herein, refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Determining the percentage of sequence identity can be done manually, or by making use of computer programs that are available in the art. Examples of useful algorithms are PILEUP (Higgins & Sharp, *CABIOS* 5:151 (1989), BLAST and BLAST 2.0 (Altschul et al. (1990), *J. Mol. Biol.* 215:403). Software for performing BLAST analyses is publicly available through the National Center for Biotechnology Information (World Wide Web at ncbi.nlm.nih.gov).

A "deletion" is defined here as a change in either amino acid or nucleotide sequence in which one or more amino acid or nucleotide residues, respectively, are absent as compared to an amino acid sequence or nucleotide sequence of a parental polypeptide or nucleic acid. Within the context of a protein, a deletion can involve deletion of about 2, about 5, about 10, up to about 20, up to about 30 or up to about 50 or more amino acids. A protein or a fragment thereof may contain more than one deletion.

An "insertion" or "addition" is that change in an amino acid or nucleotide sequences which has resulted in the addition of one or more amino acid or nucleotide residues, respectively, as compared to an amino acid sequence or nucleotide sequence of a parental protein. "Insertion" generally refers to addition to one or more amino acid residues within an amino acid sequence of a polypeptide, while "addition" can be an insertion or refer to amino acid residues added at an N- or C-terminus, or both termini. Within the context of a protein or a fragment thereof, an insertion or addition is usually of about 1, about 3, about 5, about 10, up to about 20, up to about 30 or up to about 50 or more amino acids. A protein or fragment thereof may contain more than one insertion.

A "substitution," as used herein, results from the replacement of one or more amino acids or nucleotides by different amino acids or nucleotides, respectively as compared to an amino acid sequence or nucleotide sequence of a parental protein or a fragment thereof. It is understood that a protein or a fragment thereof may have conservative amino acid substitutions which have substantially no effect on the protein's activity. By conservative substitutions is intended combinations such as gly, ala; val, ile, leu, met; asp, glu; asn, gln; ser, thr; lys, arg; cys, met; and phe, tyr, trp.

A first aspect of the disclosure relates to an immunoglobulin single variable domain that is directed against and/or specifically binds to human macrophage mannose receptor (SEQ ID NO: 1).

The term "macrophage mannose receptor" (MMR), as used herein, is known in the art and refers to a type I transmembrane protein, first identified in mammalian tissue macrophages and later in dendritic cells and a variety of endothelial and epithelial cells. Macrophages are central actors of the innate and adaptive immune responses. They are disseminated throughout most organs to protect against entry of infectious agents by internalizing and most of the time, killing them. Among the surface receptors present on macrophages, the mannose receptor recognizes a variety of molecular patterns generic to microorganisms. The MMR is composed of a single subunit with N- and O-linked glycosylations and consists of five domains: an N-terminal cysteine-rich region, which recognizes terminal sulfated sugar residues; a fibronectin type II domain with unclear function; a series of eight C-type, lectin-like carbohydrate recognition domains (CRDs) involved in $Ca^{2+}$-dependent recognition of mannose, fucose, or N-acetylglucosamine residues on the envelop of pathogens or on endogenous glycoproteins with CRDs 4-8 showing affinity for ligands comparable with that of intact MR; a single transmembrane domain; and a 45 residue-long cytoplasmic tail that contains motifs critical for MR-mediated endocytosis and sorting in endosomes (Chieppa et al. 2003, *J. Immunol.* 171:4552-60). In particular, the human macrophage mannose receptor is known as Mrc1 or CD206 (accession number nucleotide sequence: NM_002438.2; accession number protein sequence: NP_002429.1 and as in SEQ ID NO: 1).

The disclosure is in its broadest sense not particularly limited to or defined by a specific antigenic determinant, epitope, part, domain, subunit or conformation of human MMR (SEQ ID NO: 1) against which the immunoglobulin single variable domains are directed. It is expected that the immunoglobulin single variable domains according to the disclosure will generally bind to all naturally occurring or synthetic analogs, variants, mutants, alleles of the MMRs mentioned herein.

The human macrophage mannose receptor as referred to in this disclosure includes fragments of the full-length human MMR protein. A non-limiting example of a fragment of the full-length MMR protein includes the ectodomain of a particular MMR. The "ectodomain" as used herein, refers to a fragment of the MMR containing an N-terminus that is cysteine-rich, followed by a fibronectin type II domain and eight carbohydrate recognition domains (CRDs). All of the eight CRDs are particularly well conserved, especially CRD4. The ectodomain of the human macrophage mannose receptor is defined as the AA 19-AA 1383 fragment (SEQ ID NO: 5) of the corresponding full-length mouse MMR amino acid sequence as defined in NP_002429.1 (SEQ ID NO: 1), see also Table 7. Thus, according to a preferred embodiment, the immunoglobulin single variable domain specifically binds to the ectodomain of the human macrophage mannose receptor (SEQ ID NO: 5).

As used herein, the term "specifically recognizing" or "specifically binding to" or simply "specific for" refers to the ability of an immunoglobulin single variable domain to preferentially bind to a particular antigen that is present in a homogeneous mixture of different antigens and does not necessarily imply high affinity (as defined further herein). In certain embodiments, a specific binding interaction will discriminate between desirable and undesirable antigens in a sample, in some embodiments, more than about 10- to 100-fold or more (e.g., more than about 1000- or 10,000-fold). The terms "specifically bind," "selectively bind," "preferentially bind," and grammatical equivalents thereof, are used interchangeably herein.

The term "affinity," as used herein, refers to the degree to which an immunoglobulin single variable domain binds to an antigen so as to shift the equilibrium of antigen and immunoglobulin single variable domain toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the antibody (fragment) and the antigenic target. Typically, the dissociation constant is lower than $10^{-5}$ M. Preferably, the dissociation constant is lower than $10^{-6}$ M, more preferably, lower than $10^{-7}$ M. Most preferably, the dissociation constant is lower than $10^{-8}$ M.

An immunoglobulin single variable domain that can specifically bind to and/or that has affinity for a specific antigen or antigenic determinant (e.g., epitope) is said to be "against" or "directed against" the antigen or antigenic determinant. An immunoglobulin single variable domain according to the disclosure is said to be "cross-reactive" for two different antigens or antigenic determinants (such as macrophage mannose receptor from two different species of mammal, such as human MMR and mouse MMR) if it is specific for both these different antigens or antigenic determinants.

It will be appreciated that, according to the disclosure, immunoglobulin single variable domains that are directed against the human macrophage mannose receptor from one species may or may not show cross-reactivity with the macrophage mannose receptor from another species. For example, immunoglobulin single variable domains directed against human MMR, in particular, human MMR (SEQ ID NO: 1) may or may not show cross-reactivity with MMR from one or more other species of animals that are often used in animal models for diseases (for example, mouse, rat, rabbit, pig or dog). It will be clear to the skilled person that such cross-reactivity, when present, may have advantages for diagnostic and/or therapeutic development, since it allows the immunoglobulin single variable domains to be tested in such disease models.

A non-limiting example of a non-human MMR includes the mouse MMR (synonyms: MRC1 or CD206; accession number nucleotide sequence: NM_008625.2; accession number protein sequence: NP_032651.2 and as in SEQ ID NO: 3). Also, a non-limiting example of a fragment of a non-human MMR includes the ectodomain of the mouse macrophage mannose receptor, which is defined as the AA 19-AA 1388 fragment (SEQ ID NO: 6) of the corresponding full-length mouse MMR amino acid sequence as defined in NP_032651.2 (SEQ ID NO: 3). The deduced amino acid sequence of mouse mannose receptor has an overall 82% homology with the human mannose receptor, as can be easily measured in a BLASTp alignment (Altschul et al. 1990, *J. Mol. Biol.* 215:403-10).

The term "immunoglobulin single variable domain" defines molecules wherein the antigen binding site is present on, and formed by, a single immunoglobulin domain (which is different from conventional immunoglobulins or their fragments, wherein typically two immunoglobulin variable domains interact to form an antigen binding site). It should however be clear that the term "immunoglobulin single variable domain" does comprise fragments of conventional immunoglobulins wherein the antigen binding site is formed by a single variable domain.

Generally, an immunoglobulin single variable domain will have an amino acid sequence comprising four framework regions (FR1 to FR4) and three complementarity-determining regions (CDR1 to CDR3), preferably according to the following formula (1): FR1-CDR1-FR2-CDR2-FR3-CDR3-FR4 (1), or any suitable fragment thereof (which will then usually contain at least some of the amino acid residues that form at least one of the complementarity-detemaining regions).

Immunoglobulin single variable domains comprising four FRs and three CDRs are known to the person skilled in the art and have been described, as a non-limiting example, in (Wesolowski et al. 2009, *Med. Microbiol. Immunol.* 198: 157-174).

Typical, but non-limiting, examples of immunoglobulin single variable domains include light chain variable domain sequences (e.g., a VL domain sequence) or a suitable fragment thereof, or heavy chain variable domain sequences (e.g., a VH domain sequence or VHH domain sequence) or a suitable fragment thereof, as long as it is capable of forming a single antigen binding unit. Thus, according to a preferred embodiment, the immunoglobulin single variable domain is a light chain variable domain sequence (e.g., a VL domain sequence) or a heavy chain variable domain sequence (e.g., a VH domain sequence); more specifically, the immunoglobulin single variable domain is a heavy chain variable domain sequence that is derived from a conventional four-chain antibody or a heavy chain variable domain sequence that is derived from a heavy chain antibody. The immunoglobulin single variable domain may be a domain antibody, or a single-domain antibody, or a "dAB" or dAb, or a Nanobody (as defined herein), or another immunoglobulin single variable domain, or any suitable fragment of any one thereof. For a general description of single-domain antibodies, reference is made to the following book: "Single domain antibodies," *Methods in Molecular Biology*, Eds. Saerens and Muyldermans, 2012, Vol. 911. The immunoglobulin single variable domains, generally comprise a single amino acid chain that can be considered to comprise four "framework sequences" or FRs and three "complementarity-determining regions" or CDRs (as defined hereinbefore). It should be clear that framework regions of immunoglobulin single variable domains may also contribute to the binding of their antigens (Desmyter et al. 2002, *J. Biol. Chem.* 277:23645-50; Korotkov et al. 2009, *Structure* 17:255-65). The delineation of the CDR sequences (and thus also the FR sequences) can be based on the IMGT unique numbering system for V-domains and V-like domains (Lefranc et al. 2003, *Develop. Comparat. Immunol.* 27:55-77). Alternatively, the delineation of the FR and CDR sequences can be done by using the Kabat numbering system as applied to VHH domains from Camelids in the article of Riechmann and Muyldermans 2000, *J. Immunol. Methods* 240:185-195.

It should be noted that the immunoglobulin single variable domains as binding domain moiety in their broadest sense are not limited to a specific biological source or to a specific method of preparation. The term "immunoglobulin single variable domain" encompasses variable domains of different origin, comprising mouse, rat, rabbit, donkey, human, shark, camelid variable domains. According to specific embodiments, the immunoglobulin single variable domains are derived from shark antibodies (the so-called immunoglobulin new antigen receptors or IgNARs), more specifically from naturally occurring heavy chain shark antibodies, devoid of light chains, and are known as VNAR domain sequences. Preferably, the immunoglobulin single variable domains are derived from camelid antibodies. More preferably, the immunoglobulin single variable domains are derived from naturally occurring heavy chain camelid antibodies, devoid of light chains, and are known as VHH domain sequences or sdAbs.

The term "NANOBODY®" (Nb), as used herein, is a single-domain antigen binding fragment. It particularly refers to a single variable domain derived from naturally occurring heavy chain antibodies and is known to the person skilled in the art. sdAbs are usually derived from heavy chain only antibodies (devoid of light chains) seen in camelids (Hamers-Casterman et al. 1993, *Nature* 363:446-448; Desmyter et al. 1996, *Nat. Struct. Biol.* 803-811) and consequently are often referred to as VHH antibody or VHH sequence. Camelids comprise old world camelids (*Camelus bactrianus* and *Camelus dromedarius*) and new world camelids (for example, *Lama paccos, Lama glama, Lama guanicoe* and *Lama vicugna*). NANOBODY® and NANOBODIES® are registered trademarks of Ablynx NV (Belgium). For a further description of VHHs or sdAbs, reference is made to the book "Single domain antibodies," *Methods in Molecular Biology*, Eds. Saerens and Muyldermans, 2012, Vol. 911, in particular, to the Chapter by Vincke and Muyldermans (2012), as well as to a non-limiting list of patent applications, which are mentioned as general background art, and include: WO 94/04678, WO 95/04079, WO 96/34103 of the Vrije Universiteit Brussel; WO 94/25591, WO 99/37681, WO 00/40968, WO 00/43507, WO 00/65057, WO 01/40310, WO 01/44301, EP 1 134 231 and WO 02/48193 of Unilever; WO 97/49805, WO 01/21817, WO 03/035694, WO 03/054016 and WO 03/055527 of the Vlaams Instituut voor Biotechnologie (VIB); WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. The small size and unique biophysical properties of Nbs excel conventional antibody fragments for the recognition of uncommon or hidden epitopes and for binding into cavities or active sites of protein targets. Further, Nbs can be designed as multi-specific and multivalent antibodies (as defined further herein) or attached to reporter molecules (Conrath et al. 2011, *Antimicrob. Agents Chemother.* 45:2807-2812). Nbs are stable, survive the gastro-intestinal system and can easily be manufactured. Therefore, Nbs can be used in many applications including drug discovery and therapy, but also as a versatile and valuable tool for purification, functional study and crystallization of proteins (Saerens et al. 2008, *Curr. Opin. Pharmacol.* 8:600-608).

The sdAbs of the disclosure generally comprise a single amino acid chain that can be considered to comprise four "framework regions" or FRs and three (complementarity-determining regions" or CDRs, according to formula (1) (as define above). The term "complementarity-determining region" or "CDR" refers to variable regions in sdAbs and contains the amino acid sequences capable of specifically binding to antigenic targets. These CDR regions account for the basic specificity of the sdAb for a particular antigenic determinant structure. Such regions are also referred to as "hypervariable regions." The sdAbs have three CDR regions, each non-contiguous with the others (termed CDR1, CDR2, CDR3). The delineation of the FR and CDR sequences is often based on the IMGT unique numbering system for V-domains and V-like domains (Lefranc et al. 2003, *Develop. Comparat. Immunol.* 27:55-77). Alternatively, the delineation of the FR and CDR sequences can be done by using the Kabat numbering system as applied to $V_H H$ domains from Camelids in the article of Riechmann and Muyldermans 2000, *J. Immunol. Methods* 240:185-195. As will be known by the person skilled in the art, the sdAbs can, in particular, be characterized by the presence of one or more Camelidae hallmark residues in one or more of the framework sequences (according to Kabat numbering), as described, for example, in WO 08/020079, on page 75, Table A-3, incorporated herein by reference.

In one embodiment, the disclosure relates to an immunoglobulin single variable domain immunoglobulin single variable domain that is directed against and/or that specifically binds to human macrophage mannose receptor (SEQ ID NO: 1), wherein the immunoglobulin single variable domain comprises an amino acid sequence that comprises four framework regions (FR) and three complementarity-determining regions (CDR) according to the following formula (1):

FR1-CDR1-FR2-CDR2-FR3-CDR3-FR4 (1), and wherein CDR1 is chosen from the group consisting of:
 a. SEQ ID NOs: 67-96,
 b. Polypeptides that have at least 80% amino acid identity with SEQ ID NOs: 67-96,
 c. Polypeptides that have 1, 2 or 3 amino acid difference with SEQ ID NOs: 67-96,
and wherein CDR2 is chosen from the group consisting of:
 a. SEQ ID NOs: 127-156,
 b. Polypeptides that have at least 80% amino acid identity with SEQ ID NOs: 127-156,
 c. Polypeptides that have 1, 2 or 3 amino acid difference with SEQ ID NOs: 127-156,
and wherein CDR3 is chosen from the group consisting of:
 a. SEQ ID NOs: 187-216,
 b. Polypeptides that have at least 80% amino acid identity with SEQ ID NOs: 187-216,
 c. Polypeptides that have 1, 2 or 3 amino acid difference with SEQ ID NOs: 187-216.

More specifically, the framework regions (FRs) of the immunoglobulin single variable domains as described hereinabove have an amino acid sequence identity of more than 80% with the FRs of SEQ ID NOs: 37-66 (FR1), SEQ ID NOs: 97-126 (FR2), SEQ ID NOs: 157-186 (FR3), SEQ ID NOs: 217-246 (FR4).

Non-limiting examples of immunoglobulin single variable domains, according to the disclosure, are as described herein and include anti-human and cross-reactive anti-human/anti-mouse MMR sdAbs, for example, in Table 1, in particular, SEQ ID NOs: 8, 10-29; in Table 2, in particular, SEQ ID NOs: 7, 9, 20-36). In a specific embodiment, the sdAbs of the disclosure may comprise at least one of the complementarity-determining regions (CDRs) as described herein, for example, CDRs with an amino acid sequence selected from SEQ ID NOs: 67-96, 127-156, 187-216 (see Table 6). Preferably, the sdAbs of the disclosure comprise a CDR1, a CDR2 and a CDR3 selected from the group consisting of SEQ ID NOs: 67-96, 127-156, 187-216, according to the above-described formula (1). Preferably, a sdAb is provided comprising an amino acid sequence according to formula (1) with a CDR1 consisting of SEQ ID NO: 67, a CDR2 consisting of SEQ ID NO: 127, a CDR3 consisting of SEQ ID NO: 187, or with polypeptides that have at least 80% amino acid identity with SEQ ID NO: 67, SEQ ID NO: 127, SEQ ID NO: 187. More specifically, the sdAbs can be selected from the group comprising SEQ ID NOs: 7-36, or a functional fragment thereof. A "functional fragment" or a "suitable fragment," as used herein, may, for example, comprise one of the CDR loops. Preferably, the functional fragment comprises CDR3. More specifically, the sdAbs consist of any of SEQ ID NOs: 7-36, preferably SEQ ID NOs: 7, 8, 9, 10, most preferably SEQ ID NO: 7.

It should be noted that the terms "NANOBODY®" and "single-domain antibody" as used herein in their broadest sense is not limited to a specific biological source or to a specific method of preparation. For example, the sdAbs of the disclosure can generally be obtained: (1) by isolating the $V_HH$ domain of a naturally occurring heavy chain antibody; (2) by expression of a nucleotide sequence encoding a naturally occurring $V_HH$ domain; (3) by "humanization" of a naturally occurring $V_HH$ domain or by expression of a nucleic acid encoding a such humanized $V_HH$ domain; (4) by "camelization" of a naturally occurring VH domain from any animal species and, in particular, from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a sdAb using techniques for nucleic acid synthesis known per se, followed by expression of the nucleic acid thus obtained; and/or (8) by any combination of one or more of the foregoing.

One preferred class of sdAbs corresponds to the $V_HH$ domains of naturally occurring heavy chain antibodies directed against a macrophage mannose receptor, preferably against a human macrophage mannose receptor. As further described herein, such $V_HH$ sequences can generally be generated or obtained by suitably immunizing a species of Camelid with a desired MMR (i.e., so as to raise an immune response and/or heavy chain antibodies directed against a desired MMR), by obtaining a suitable biological sample from the Camelid (such as a blood sample, or any sample of B-cells), and by generating $V_HH$ sequences directed against the MMR, starting from the sample, using any suitable technique known per se. Such techniques will be clear to the skilled person. Alternatively, such naturally occurring $V_HH$ domains against MMR can be obtained from naive libraries of Camelid $V_HH$ sequences, for example, by screening such a library using MMR or at least one part, fragment, antigenic determinant or epitope thereof using one or more screening techniques known per se. Such libraries and techniques are, for example, described in WO 9937681, WO 0190190, WO 03025020 and WO 03035694. Alternatively, improved synthetic or semi-synthetic libraries derived from naive $V_HH$ libraries may be used, such as $V_HH$ libraries obtained from naive $V_HH$ libraries by techniques such as random mutagenesis and/or CDR shuffling, as, for example, described in WO 0043507. Yet another technique for obtaining $V_HH$ sequences directed against a desired MMR involves suitably immunizing a transgenic mammal that is capable of expressing heavy chain antibodies (i.e., so as to raise an immune response and/or heavy chain antibodies directed against a MMR), obtaining a suitable biological sample from the transgenic mammal (such as a blood sample, or any sample of B-cells), and then generating $V_HH$ sequences directed against the MMR starting from the sample, using any suitable technique known per se. For example, for this purpose, the heavy chain antibody-expressing mice and the further methods and techniques described in WO 02085945 and in WO 04049794 can be used.

Accordingly, the disclosure encompasses methods of generating immunoglobulin single variable domains according to the disclosure. As a non-limiting example, a method is provided of generating sdAbs directed against or specifically binding to the human macrophage mannose receptor (as described herein), comprising:

(i) immunizing an animal with a MMR, in particular, a human MMR (e.g., SEQ ID NOs: 1 or 2), or a fragment thereof (e.g., SEQ ID NO: 5); and (ii) screening for sdAbs specifically binding to human MMR.

For the immunization of an animal with a MMR, the MMR may be produced and purified using conventional methods that may employ expressing a recombinant form of the MMR in a host cell, and purifying the MMR using affinity chromatography and/or antibody-based methods. Any suitable animal, e.g., a warm-blooded animal, in particular, a mammal such as a rabbit, mouse, rat, camel, sheep, cow, shark, or pig or a bird such as a chicken or turkey, may be immunized using any of the techniques well known in the art suitable for generating an immune response. The screening for sdAbs, as a non-limiting example, specifically binding to a MMR may, for example, be performed by screening a set, collection or library of cells that express heavy chain antibodies on their surface (e.g., B-cells obtained from a suitably immunized Camelid), or bacteriophages that display a fusion of genIII and sdAb at their surface, by screening of a (naïve or immune) library of $V_HH$ sequences or sdAb sequences, or by screening of a (naïve or immune) library of nucleic acid sequences that encode VHH sequences or sdAb sequences, which may all be performed in a manner known per se, and which method may optionally further comprise one or more other suitable steps, such as, for example, and without limitation, a step of affinity maturation, a step of expressing the desired amino acid sequence, a step of screening for binding and/or for activity against the desired antigen (in this case, the MMR), a step of determining the desired amino acid sequence or nucleotide sequence, a step of introducing one or more humanizing substitutions, a step of formatting in a suitable multivalent and/or multi-specific format, a step of screening for the desired biological and/or physiological properties (i.e., using a suitable assay known in the art), and/or any combination of one or more of such steps, in any suitable order.

A particularly preferred class of immunoglobulin single variable domains of the disclosure comprises sdAbs with an amino acid sequence that corresponds to the amino acid sequence of a naturally occurring $V_HH$ domain, but that has been "humanized," i.e., by replacing one or more amino acid residues in the amino acid sequence of the naturally occurring $V_HH$ sequence and, in particular, in the framework sequences, by one or more of the amino acid residues that occur at the corresponding position(s) in a VH domain from a conventional four-chain antibody from a human being. This can be performed in a manner known per se, which will be clear to the skilled person, on the basis of the further description herein and the prior art on humanization. Again, it should be noted that such humanized sdAbs of the disclosure can be obtained in any suitable manner known per se (i.e., as indicated under points (1)-(8) above) and thus are not strictly limited to polypeptides that have been obtained using a polypeptide that comprises a naturally occurring $V_HH$ domain as a starting material. Humanized sdAbs may have several advantages, such as a reduced immunogenicity, compared to the corresponding naturally occurring $V_HH$ domains. Such humanization generally involves replacing one or more amino acid residues in the sequence of a naturally occurring $V_HH$ with the amino acid residues that occur at the same position in a human VH domain, such as a human VH3 domain. The humanizing substitutions should be chosen such that the resulting humanized sdAbs still retain the favorable properties of sdAbs as defined herein. The skilled person will be able to select humanizing substitutions or suitable combinations of humanizing substitutions which optimize or achieve a desired or suitable balance between the favorable properties provided by the humanizing substitutions on the one hand and the favorable properties of naturally occurring $V_HH$ domains on the other hand.

Another particularly preferred class of immunoglobulin single variable domains of the disclosure comprises sdAbs with an amino acid sequence that corresponds to the amino acid sequence of a naturally occurring VH domain, but that has been "camelized," i.e., by replacing one or more amino acid residues in the amino acid sequence of a naturally occurring VH domain from a conventional 4-chain antibody by one or more of the amino acid residues that occur at the corresponding position(s) in a VHH domain of a heavy chain antibody. Such "camelizing" substitutions are preferably inserted at amino acid positions that form and/or are present at the VH-VL interface, and/or at the so-called Camelidae hallmark residues, as defined herein (see, for example, WO 9404678, WO 08/020079). Preferably, the VH sequence that is used as a starting material or starting point for generating or designing the camelized sdAb is preferably a VH sequence from a mammal, more preferably the VH sequence of a human being, such as a VH3 sequence. However, it should be noted that such camelized sdAbs of the disclosure can be obtained in any suitable manner known per se (i.e., as indicated under points (1)-(8) above) and thus are not strictly limited to polypeptides that have been obtained using a polypeptide that comprises a naturally occurring VH domain as a starting material.

For example, both "humanization" and "camelization" can be performed by providing a nucleotide sequence that encodes a naturally occurring $V_HH$ domain or VH domain, respectively, and then changing, in a manner known per se, one or more codons in the nucleotide sequence in such a way that the new nucleotide sequence encodes a "humanized" or "camelized" sdAb of the disclosure, respectively. This nucleic acid can then be expressed in a manner known per se, so as to provide the desired sdAb of the disclosure. Alternatively, based on the amino acid sequence of a naturally occurring VHH domain or VH domain, respectively, the amino acid sequence of the desired humanized or camelized sdAb of the disclosure, respectively, can be designed and then synthesized de novo using techniques for peptide synthesis known per se. Also, based on the amino acid sequence or nucleotide sequence of a naturally occurring $V_HH$ domain or VH domain, respectively, a nucleotide sequence encoding the desired humanized or camelized sdAb of the disclosure, respectively, can be designed and then synthesized de novo using techniques for nucleic acid synthesis known per se, after which the nucleic acid thus obtained can be expressed in a manner known per se, so as to provide the desired sdAb of the disclosure. Other suitable methods and techniques for obtaining the sdAbs of the disclosure and/or nucleic acids encoding the same, starting from naturally occurring VH sequences or preferably VHH sequences, will be clear from the skilled person, and may, for example, comprise combining one or more parts of one or more naturally occurring VH sequences (such as one or more FR sequences and/or CDR sequences), one or more parts of one or more naturally occurring $V_HH$ sequences (such as one or more FR sequences or CDR sequences), and/or one or more synthetic or semi-synthetic sequences, in a suitable manner, so as to provide a sdAb of the disclosure or a nucleotide sequence or nucleic acid encoding the same.

The Also within the scope of the disclosure are natural or synthetic analogs, mutants, variants, alleles, homologs and orthologs (herein collectively referred to as "variants") of the immunoglobulin single variable domains of the disclosure as defined herein. Some particularly preferred, but non-limiting examples of immunoglobulin single variable domains, as well as combinations of CDR sequences are mentioned in Table 6, which lists the CDR sequences that are present in a number of preferred, but non-limiting immunoglobulin single variable domains of the disclosure. Thus, according to one embodiment of the disclosure, the term "immunoglobulin single variable domain of the disclosure," in its broadest sense, also covers such variants, in particular, variants of the sdAbs of SEQ ID NOs: 7-36 (see Table 1, Table 2). Generally, in such variants, one or more amino acid residues may have been replaced, deleted and/or added, compared to the sdAbs of the disclosure as defined herein. Such substitutions, insertions or deletions may be made in one or more of the framework regions and/or in one or more of the CDRs and, in particular, variants of the CDRs of the sdAbs of SEQ ID NOs: 7-36, the CDRs corresponding to SEQ ID NOs: 67-96 (CDR1), SEQ ID NOs: 127-156, SEQ ID NOs: 187-216 (CDR3) (Table 6). Variants, as used herein, are sequences wherein each or any framework region and each or any complementarity-determining region shows at least 80% identity, preferably at least 85% identity, more preferably 90% identity, even more preferably 95% identity or, still even more preferably 99% identity with the corresponding region in the reference sequence (i.e., FR1_variant versus FR1_reference, CDR1_variant versus CDR1_reference, FR2_variant versus FR2_reference, CDR2_variant versus CDR2_reference, FR3_variant versus FR3_reference, CDR3_variant versus CDR3_reference, FR4_variant versus FR4_reference), as can be measured electronically by making use of algorithms such as PILEUP and BLAST (Altschul et al. 1990, *J. Mol. Biol.* 215:403; Higgins & Sharp 1989, *CABIOS* 5:151). Software for performing BLAST analyses is publicly available through the National Center for Biotechnology Information (World Wide Web at ncbi.nlm.nih.gov). Such variants of immunoglobulin single variable domains may be of particular advantage since they may have improved potency or other desired properties.

By means of non-limiting examples, a substitution may, for example, be a conservative substitution (as described herein) and/or an amino acid residue may be replaced by another amino acid residue that naturally occurs at the same position in another $V_HH$ domain. Thus, any one or more substitutions, deletions or insertions, or any combination thereof, that either improve the properties of the sdAb of the disclosure or that at least do not detract too much from the desired properties or from the balance or combination of desired properties of the sdAb of the disclosure (i.e., to the extent that the sdAb is no longer suited for its intended use) are included within the scope of the disclosure. A skilled person will generally be able to determine and select suitable substitutions, deletions or insertions, or suitable combinations of thereof, based on the disclosure herein and optionally after a limited degree of routine experimentation, which may, for example, involve introducing a limited number of possible substitutions and determining their influence on the properties of the sdAbs thus obtained.

According to particularly preferred embodiments, variants of the immunoglobulin single variable domains, in particular, the sdAbs of the disclosure may have a substitution, deletion or insertion, of 1, 2 or 3 amino acids in one, two or three of the CDRs, more specifically, (i) in CDR1 or CDR2 or CDR3; (ii) in CDR1 and CDR2, or, in CDR1 and CDR3, or, in CDR2 and CDR3; (iii) in CDR1 and CDR2 and CDR3, as listed in Table 6. More preferably, variants of the immunoglobulin single variable domains, in particular, the sdAbs of the disclosure, may have a conservative substitution (as defined herein) of 1, 2 or 3 amino acids in one, two or three of the CDRs, more specifically, (i) in CDR1 or CDR2 or CDR3; (ii) in CDR1 and CDR2, or, in CDR1 and CDR3, or, in CDR2 and CDR3; (iii) in CDR1 and CDR2 and CDR3, as listed in Table 6.

Further, depending on the host organism used to express the immunoglobulin single variable domain of the disclosure, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example, to allow site-specific pegylation.

Examples of modifications, as well as examples of amino acid residues within the immunoglobulin single variable domain, preferably the sdAb sequence, that can be modified (i.e., either on the protein backbone but preferably on a side chain), methods and techniques that can be used to introduce such modifications and the potential uses and advantages of such modifications will be clear to the skilled person. For example, such a modification may involve the introduction (e.g., by covalent linking or in another suitable manner) of one or more functional groups, residues or moieties into or onto the immunoglobulin single variable domain of the disclosure and, in particular, of one or more functional groups, residues or moieties that confer one or more desired properties or functionalities to the immunoglobulin single variable domain of the disclosure. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins and, in particular, for the modification of antibodies or antibody fragments (including ScFvs and single-domain antibodies), for which reference is, for example, made to *Remington's Pharmaceutical Sciences*, 16th ed., Mack Publishing Co., Easton, Pa. (1980). Such functional groups may, for example, be linked directly (for example, covalently) to a immunoglobulin single variable domain of the disclosure, or optionally via a suitable linker or spacer, as will again be clear to the skilled person.

One of the most widely used techniques for increasing the half-life and/or reducing immunogenicity of pharmaceutical proteins comprises attachment of a suitable pharmacologically acceptable polymer, such as poly(ethylene glycol) (PEG) or derivatives thereof (such as methoxypoly(ethylene glycol) or mPEG). Generally, any suitable form of pegylation can be used, such as the pegylation used in the art for antibodies and antibody fragments (including but not limited to (single) domain antibodies and ScFvs); reference is made to, for example, Chapman, *Nat. Biotechnol.* 54:531-545 (2002); by Veronese and Harris, *Adv. Drug Deliv. Rev.* 54:453-456 (2003); by Harris and Chess, *Nat. Rev. Drug Discov.* 2 (2003); and in WO 04060965. Various reagents for pegylation of proteins are also commercially available, for example, from Nektar Therapeutics, USA. Preferably, site-directed pegylation is used, in particular, via a cysteine-residue (see, for example, Yang et al., *Protein Engineering* 16, 10:761-770 (2003). For example, for this purpose, PEG may be attached to a cysteine residue that naturally occurs in a sdAb of the disclosure, a sdAb of the disclosure may be modified so as to suitably introduce one or more cysteine residues for attachment of PEG, or an amino acid sequence comprising one or more cysteine residues for attachment of PEG may be fused to the N- and/or C-terminus of a sdAb of the disclosure, all using techniques of protein engineering known per se to the skilled person. Preferably, for the immunoglobulin single variable domains and proteins of the disclosure, a PEG is used with a molecular weight of more than 5000, such as more than 10,000 and less than 200,000, such as less than 100,000; for example, in the range of 20,000-80,000.

Another, usually less preferred modification comprises N-linked or O-linked glycosylation, usually as part of co-translational and/or post-translational modification, depending on the host cell used for expressing the immunoglobulin single variable domain or polypeptide of the disclosure. Another technique for increasing the half-life of an immunoglobulin single variable domain may comprise the engineering into bifunctional constructs (for example, one sdAb against the target MMR and one against a serum protein such as albumin) or into fusions of immunoglobulin single variable domains with peptides (for example, a peptide against a serum protein such as albumin).

Yet another modification may comprise the introduction of one or more detectable labels or other signal-generating groups or moieties, depending on the intended use of the labeled sdAb. Suitable labels and techniques for attaching, using and detecting them will be clear to the skilled person and, for example, include, but are not limited to, fluorescent labels (such as IRDye800, VivoTag800, fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, therometric acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro, or in situ diagnosis and imaging, as well as chromophores and enzymes (such as malate dehydrogenase, staphylococcal nuclease, delta V steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person and, for example, include moieties that can be detected using NMR or ESR spectroscopy. Such labeled sdAbs and polypeptides of th disclosure may, for example, be used for in vitro, in vivo, or in situ assays (including immunoassays known per se, such as ELISA, RIA, EIA and other "sandwich assays," etc.) as well as in vivo diagnostic and imaging purposes, depending on the choice of the specific label. As will be clear to the skilled person, another modification may involve the introduction of a chelating group, for example, to chelate one of the metals or metallic cations referred to above. Suitable chelating groups, for example, include, without limitation, 2,2',2"-(10-(2-((2,5-dioxopyrrolidin-1-yl)oxy)-2-oxoethyl)-1,4,7,10-tetraazacyclododecane-1,4,7-triyl)triacetic acid (DOTA), 2,2'-(7-(2-((2,5-dioxopyrrolidin-1-yl)oxy)-2-oxoethyl)-1,4,7-triazonane-1,4-diyl)diacetic acid (NOTA), diethyl-enetriaminepentaacetic acid (DTPA) or ethylenediaminetetraacetic acid (EDTA). Yet another modification may comprise the introduction of a functional group that is one part of a specific binding pair, such as the biotin-(strept)avidin binding pair. Such a functional group may be used to link the sdAb of the disclosure to another protein, polypeptide or chemical compound that is bound to the other half of the binding pair, i.e., through formation of the binding pair. For example, a sdAb of the disclosure may be conjugated to biotin, and linked to another protein, polypeptide, compound or carrier conjugated to avidin or streptavidin. For example, such a conjugated sdAb may be used as a reporter, for example, in a diagnostic system where a detectable signal-producing agent is conjugated to avidin or streptavidin. Such binding pairs may, for example, also be used to bind the sdAb of the disclosure to a carrier, including carriers suitable for pharmaceutical purposes. One non-limiting example are the liposomal formulations described by Cao and Suresh, *Journal of Drug Targetting* 8, 4:257 (2000). Such binding pairs may also be used to link a therapeutically active agent to the sdAb of the disclosure.

Thus, according to a preferred embodiment, the immunoglobulin single variable domain as used in the disclosure is coupled or fused to a detectable label, either directly or through a linker. Preferably, the detectable label is a radio-isotope, in particular, a radioactive tracer suitable for medical applications, such as in in vivo nuclear imaging. Examples include, without the purpose of being limitative, technetium 99m ($^{99m}$Tc), iodium 123 ($^{123}$I), zirconium 89 ($^{89}$Zr), iodium 125 ($^{125}$I), indium 111 ($^{111}$In) fluor 18 ($^{18}$F), copper 64 ($^{64}$Cu), gallium 67 ($^{67}$Ga), gallium 68 ($^{68}$Ga), and any other radio-isotope which can be used in animals, in particular, mouse, rabbit or human. According to a specific embodiment, the detectable label is $^{99m}$Tc.

In another preferred embodiment, the immunoglobulin single variable domain as used in the disclosure is coupled to or fused to a functional moiety, in particular, a therapeutically active agent, either directly or through a linker. As used herein, a "therapeutically active agent" means any molecule that has or may have a therapeutic effect (i.e., curative or stabilizing effect) in the context of treatment of a disease (as described further herein).

Preferably, a therapeutically active agent is a disease-modifying agent, which can be a cytotoxic agent, such as a toxin, or a cytotoxic drug, or an enzyme capable of converting a prodrug into a cytotoxic drug, or a radionuclide, or a cytotoxic cell, or which can be a non-cytotoxic agent. Even more preferably, a therapeutically active agent has a curative effect on the disease. Specific, but non-limiting, examples of such moieties are described in the Example section. According to one specific embodiment, the therapeutically active agent is not a cytotoxic agent.

As used herein, "linker molecules" or "linkers" are peptides of 1 to 200 amino acids length, and are typically, but not necessarily, chosen or designed to be unstructured and flexible. For instance, one can choose amino acids that form no particular secondary structure. Or, amino acids can be chosen so that they do not form a stable tertiary structure. Or, the amino acid linkers may form a random coil. Such linkers include, but are not limited to, synthetic peptides rich in Gly, Ser, Thr, Gln, Glu or further amino acids that are frequently associated with unstructured regions in natural proteins (Z. Dosztányi, V. Csizmok, P. Tompa, and I. Simon (2005), IUPred: web server for the prediction of intrinsically unstructured regions of proteins based on estimated energy content, *Bioinformatics* (Oxford, England), 21 (16):3433-4).

Thus, according to specific embodiments, the amino acid (AA) linker sequence is a peptide of between 0 and 200 AA, between 0 and 150 AA, between 0 and 100 AA, between 0 and 90 AA, between 0 and 80 AA, between 0 and 70 AA, between 0 and 60 AA, between 0 and 50 AA, between 0 and 40 AA, between 0 and 30 amino acids, between 0 and 20 AA, between 0 and 10 amino acids, between 0 and 5 amino acids. Non-limiting examples of suitable linker sequences include $(GS)_5$ (GSGSGSGSGS; SEQ ID NO: 248), $(GS)_{10}$ (GSGSGSGSGSGSGSGSGSGS; SEQ ID NO: 249), $(G_4S)_3$ (GGGGSGGGGSGGGGS; SEQ ID NO: 250), llama IgG2 hinge (AHHSEDPSSKAPKAPMA; SEQ ID NO: 251) or human IgA hinge (SPSTPPTPSPSTPPAS; SEQ ID NO: 252) linkers. Examples of sequences of short linkers include, but are not limited to, PPP, PP or GS.

For certain applications, it may be advantageous that the linker molecule comprises or consists of one or more particular sequence motifs. For example, a proteolytic cleavage site can be introduced into the linker molecule such that detectable label or moiety can be released. Useful cleavage sites are known in the art, and include a protease cleavage site such as Factor Xa cleavage site having the sequence IEGR (SEQ ID NO: 253), the thrombin cleavage site having the sequence LVPR (SEQ ID NO: 254), the enterokinase cleaving site having the sequence DDDDK (SEQ ID NO: 255), or the PreScission cleavage site LEVLFQGP (SEQ ID NO: 256).

Alternatively, in case the immunoglobulin single variable domain is linked to a detectable label or moiety using chemoenzymatic methods for protein modification, the linker moiety may exist of different chemical entities, depending on the enzymes or the synthetic chemistry that is used to produce the covalently coupled molecule in vivo or in vitro (reviewed in: Rabuka 2010, *Curr. Opin. Chem. Biol.* 14:790-796).

In a particular embodiment, the immunoglobulin single variable domains of the disclosure are in a "multivalent" form and are formed by bonding, chemically or by recombinant DNA techniques, together two or more monovalent immunoglobulin single variable domains. Non-limiting examples of multivalent constructs include "bivalent" constructs, "trivalent" constructs, "tetravalent" constructs, and so on. The immunoglobulin single variable domains comprised within a multivalent construct may be identical or different. In another particular embodiment, the immunoglobulin single variable domains of the disclosure are in a "multi-specific" form and are formed by bonding together two or more immunoglobulin single variable domains, of which at least one with a different specificity. Non-limiting examples of multi-specific constructs include "bi-specific" constructs, "tri-specific" constructs, "tetra-specific" constructs, and so on. To illustrate this further, any multivalent or multispecific (as defined herein) immunoglobulin single variable domain of the disclosure may be suitably directed against two or more different epitopes on the same antigen, for example, against two or more different parts of the MMR ectodomain; or may be directed against two or more different antigens, for example, against MMR and one or more other marker. Preferably, a monovalent immunoglobulin single variable domain of the disclosure is such that it will bind to the MMR (as described herein) with an affinity less than 500 nM, preferably less than 200 nM, more preferably less than 10 nM, such as less than 500 pM. Multivalent or multispecific immunoglobulin single variable domains of the disclosure may also have (or be engineered and/or selected for) increased avidity and/or improved selectivity for the desired MMR, and/or for any other desired property or combination of desired properties that may be obtained by the use of such multivalent or multispecific immunoglobulin single variable domains.

In a further aspect, the disclosure also provides a polypeptide comprising any of the immunoglobulin single variable domains according to the disclosure, either in a monovalent, multivalent or multi-specific form. Thus, polypeptides comprising monovalent, multivalent or multispecific sdAbs are included here as non-limiting examples.

Another aspect of the disclosure relates to a nucleic acid sequence encoding an immunoglobulin single variable domain, in particular, a sdAb, or a polypeptide of the disclosure, as described hereinbefore. Further, the disclosure also envisages expression vectors comprising nucleic acid sequences encoding any of the above immunoglobulin single variable domains or polypeptides, as well as host cells expressing such expression vectors. Suitable expression systems include constitutive and inducible expression systems in bacteria or yeasts, virus expression systems, such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris*, and the like. Suitable animal host cells include HEK 293, COS, S2, CHO, NSO, DT40 and the like. The cloning, expression and/or purification of the sdAbs can be done according to techniques known by the skilled person in the art.

In still another aspect, the disclosure also relates to a pharmaceutical composition comprising a immunoglobulin single variable domain of the disclosure, and at least one of a pharmaceutically acceptable carrier, adjuvant or diluent. Preferably, the pharmaceutical composition comprises a therapeutically effective amount of an immunoglobulin single variable domain of the disclosure, and at least one of a pharmaceutically acceptable carrier, adjuvant or diluent.

A "carrier" or "adjuvant," in particular, a "pharmaceutically acceptable carrier" or "pharmaceutically acceptable adjuvant" is any suitable excipient, diluent, carrier and/or adjuvant which, by themselves, do not induce the production of antibodies harmful to the individual receiving the composition nor do they elicit protection. So, pharmaceutically acceptable carriers are inherently non-toxic and nontherapeutic, and they are known to the person skilled in the art. Suitable carriers or adjuvantia typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles. Carriers or adjuvants may be, as a non-limiting example, Ringer's solution, dextrose solution or Hank's solution. Non aqueous solutions such as fixed oils and ethyl oleate may also be used. A preferred excipient is 5% dextrose in saline. The excipient may contain minor amounts of additives such as substances that enhance isotonicity and chemical stability, including buffers and preservatives.

As used herein, the terms "therapeutically effective amount," "therapeutically effective dose" and "effective amount" mean the amount needed to achieve the desired result or results. As used herein, "pharmaceutically acceptable" means a material that is not biologically or otherwise undesirable, i.e., the material may be administered to an individual along with the compound without causing any undesirable biological effects or interacting in a deleterious manner with any of the other components of the pharmaceutical composition in which it is contained.

Certain of the above-described immunoglobulin single variable domains may have diagnostic, prognostic and/or therapeutic utility. More specifically, the disclosure also envisages immunoglobulin single variable domains of the disclosure for use in diagnosis, prognosis, prevention and/or treatment of cancer, as well as for monitoring or assessing the impact of a therapy.

As used herein, the term "diagnosing" or grammatically equivalent wordings, means determining whether or not a subject suffers from a particular disease or disorder. As used herein, "prognosing" or grammatically equivalent wordings, means determining whether or not a subject has a risk of developing a particular disease or disorder.

As used herein, the term "preventing cancer" means inhibiting or reversing the onset of the disease, inhibiting or reversing the initial signs of the disease, inhibiting the appearance of clinical symptoms of the disease. As used herein, "treating cancer" or "treating a subject or individual having cancer" includes substantially inhibiting the disease, substantially slowing or reversing the progression of the disease, substantially ameliorating clinical symptoms of the disease or substantially preventing the appearance of clinical symptoms of the disease. In particular, it includes inhibition of the replication of cancer cells, inhibition of the spread of cancer, reduction in tumor size, lessening or reducing the number of cancerous cells in the body, and/or amelioration or alleviation of the symptoms of cancer. A treatment is considered therapeutic if there is a decrease in mortality and/or morbidity, and may be performed prophylactically, or therapeutically. A variety of subjects or individuals are treatable. Generally the "subjects" are mammals or mammalian, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects will be humans.

As used herein, the term "cancer" refers to any neoplastic disorder, including such cellular disorders as, for example, renal cell cancer, Kaposi's sarcoma, chronic leukemia, breast cancer, sarcoma, ovarian carcinoma, rectal cancer, throat cancer, melanoma, colon cancer, bladder cancer, mastocytoma, lung cancer, mammary adenocarcinoma, pharyngeal squamous cell carcinoma, and gastrointestinal or stomach cancer.

Accordingly, the disclosure also relates to a method of preventing and/or treating cancer, comprising administering a pharmaceutically effective amount of an immunoglobulin single variable domain of the disclosure or a pharmaceutical composition derived thereof to a subject in need thereof.

In a specific embodiment, the disclosure relates to a method of inhibiting tumor growth or tumor metastases in a subject in need thereof comprising selectively targeting TAM subpopulations linked to different intratumoral regions, such as hypoxic or normoxic regions of a solid tumor. As a specific embodiment, the above method comprises administering to the subject a pharmaceutically effective amount of an immunoglobulin single variable domain or a pharmaceutical composition or a polypeptide according to the disclosure, in particular, an immunoglobulin single variable domain fused to a toxin, or to a cytotoxic drug, or to an enzyme capable of converting a prodrug into a cytotoxic drug, or to a radionuclide, or coupled to a cytotoxic cell, and the like (see also Example section).

As used herein, "TAM subpopulations" refer to distinct subsets of tumor-associated macrophages (TAMs) that are present in a tumor environment, which are characterized by the differential expression of molecular markers, as listed in Table 1 on p. 5733 of Movahedi et al. 2010, *Cancer Res.* 70:5728-39, incorporated herein by reference. For example, the macrophage mannose receptor (MMR) is one of the molecular markers that is specifically expressed on a TAM subpopulation that resides predominantly in the hypoxic regions of a tumor. According to particular embodiments, a TAM subpopulation can be defined as MHC II$^{low}$ or MHC II$^{hi}$. In a preferred embodiment, the TAM subpopulation is defined as MHC II$^{low}$. In an even more preferred embodiment, a TAM subpopulation is defined as a MMR-positive TAM subpopulation. The term "MMR-positive TAMs" means tumor-associated macrophages that express the macrophage mannose receptor at a high amount on their surface and predominantly reside in the hypoxic region of a tumor, in contrast to "MMR-negative TAMs," which do not or only poorly express the macrophage mannose receptor and mainly reside in the normoxic regions of a tumor (see also Movahedi et al. 2010, *Cancer Res.* 70:5728-39).

The immunoglobulin single variable domain and/or pharmaceutical composition may be administered by any suitable method within the knowledge of the skilled man. The administration of an immunoglobulin single variable domain as described above or a pharmaceutically acceptable salt thereof may be by way of oral, inhaled or parenteral administration. In particular embodiments, the immunoglobulin single variable domain is delivered through intrathecal or intracerebroventricular administration. The active compound may be administered alone or preferably formulated as a pharmaceutical composition. An amount effective to treat a certain disease or disorder that express the antigen recognized by the immunoglobulin single variable domain depends on the usual factors such as the nature and severity of the disorder being treated and the weight of the mammal. However, a unit dose will normally be in the range of 0.01 to 50 mg, for example, 0.01 to 10 mg, or 0.05 to 2 mg of immunoglobulin single variable domain or a pharmaceutically acceptable salt thereof. Unit doses will normally be administered once or more than once a day, for example, 2, 3, or 4 times a day, more usually 1 to 3 times a day, such that the total daily dose is normally in the range of 0.0001 to 1 mg/kg; thus a suitable total daily dose for a 70 kg adult is 0.01 to 50 mg, for example, 0.01 to 10 mg or more usually 0.05 to 10 mg.

It is greatly preferred that the immunoglobulin single variable domain or a pharmaceutically acceptable salt thereof is administered in the form of a unit-dose composition, such as a unit dose oral, parenteral, or inhaled composition. Such compositions are prepared by admixture and are suitably adapted for oral, inhaled or parenteral administration, and as such may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tableting agents, lubricants, disintegrants, colorants, flavorings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate. These solid oral compositions may be prepared by conventional methods of blending, filling, tableting or the like.

Repeated blending operations may be used to distribute the active agent throughout those compositions employing large quantities of fillers. Such operations are, of course, conventional in the art. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example, sorbitol, syrup, methyl cellulose, gelatin, hydroxyethylcellulose, carboxymethyl cellulose, aluminium stearate gel or hydrogenated edible fats, emulsifying agents, for example, lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example, methyl or propyl p-hydroxybenzoate or sorbic acid, and if desired conventional flavoring or coloring agents. Oral formulations also include conventional sustained release formulations, such as tablets or granules having an enteric coating. Preferably, compositions for inhalation are presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, for example, between 1 and 5 microns, such as between 2 and 5 microns. A favored inhaled dose will be in the range of 0.05 to 2 mg, for example, 0.05 to 0.5 mg, 0.1 to 1 mg or 0.5 to 2 mg. For parenteral administration, fluid unit dose forms are prepared containing a compound of the disclosure and a sterile vehicle. The active compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anesthetic, preservatives and buffering agents are also dissolved in the vehicle.

To enhance the stability, the composition can be frozen after filling into the vial and the water removed under vacuum. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the active compound. Where appropriate, small amounts of bronchodilators, for example, sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included. As is common practice, the compositions will usually be accompanied by written or printed directions for use in the medical treatment concerned. All these medicaments can be intended for human or veterinary use.

The efficacy of the immunoglobulin single variable domains of the disclosure, and of compositions comprising the same, can be tested using any suitable in vitro assay, cell-based assay, in vivo assay and/or animal model known per se, or any combination thereof, depending on the specific disease or disorder involved.

In a specific embodiment, it should be clear that the therapeutic method of the disclosure against cancer can also be used in combination with any other cancer therapy known in the art such as irradiation, chemotherapy or surgery.

Reliable hypoxia tracers that can be used for non-invasive tumor imaging are currently unavailable or limiting. The availability of such tracers would represent a significant progress in the field of radiotherapy, since they would allow the radiotherapist to adapt the radiation dose, depending on the targeted tumor region (hypoxic versus normoxic). The identification of tumor-associated macrophage (TAM) subsets that are situated in hypoxic/normoxic environments allows for the identification of macrophage-specific biomarkers that can be used for non-invasive imaging of hypoxic/normoxic areas in tumors. For example, MMR represents such a marker, since it is preferentially expressed on the hypoxic MHC II$^{low}$ TAMs. Due to their small size and high tumor penetrance, immunoglobulin single variable domains, in particular, sdAbs, are the ideal format for non-invasive imaging. Immunoglobulin single variable domains raised against markers that are preferentially expressed on the hypoxic MHC II$^{low}$ TAMs can be used for the imaging of hypoxia in tumors. The immunoglobulin single variable domains against human MMR (or cross-reactive against human/mouse MMR) can be used in this respect.

Other applications of TAM subset-specific immunoglobulin single variable domains coupled to tracers for imaging (for example, Near Infrared Fluorescent or NIRF tracers), include but are not limited to, (i) accurately quantifying the amount of TAM or TAM subsets inside any given tumor, which can be of prognostic value, (ii) assessing the impact of therapy, including TAM-directed therapies as presently claimed, on the amount and/or the activation state of TAM, (iii) visualizing hypoxic/normoxic regions within the tumor.

Accordingly, in a further aspect, the disclosure provides immunoglobulin single variable domains for use as contrast agent in non-invasive in vivo medical imaging. In a preferred embodiment, nuclear imaging is envisaged using the immunoglobulin single variable domains of the disclosure, whereby MMR-positive tumor-associated macrophages are targeted inside a tumor. In one specific embodiment, the disclosure provides immunoglobulin single variable domains for use in monitoring the relative percentage of MMR-positive TAMs and/or the evolution in function of time of the relative percentage of MMR-positive TAMs.

As used herein, the term "medical imaging" refers to the technique and process that is used to visualize the inside of an organism's body (or parts and/or functions thereof), for clinical purposes (e.g., disease diagnosis, prognosis or therapy monitoring) or medical science (e.g., study of anatomy and physiology). Examples of medical imaging methods include invasive techniques, such as intravascular ultrasound (IVUS), as well as non-invasive techniques, such as magnetic resonance imaging (MRI), ultrasound (US) and nuclear imaging. Examples of nuclear imaging include positron emission tomography (PET) and single photon emission-computed tomography (SPECT).

The disclosure also encompasses a method of in vivo imaging tumor cells in a subject, the method comprising the step of:
  administering to the subject an immunoglobulin single variable domain according to the disclosure fused to a detectable label.

As used herein, "tumor cells" or simply "tumor" refers to the tumor tissue as a whole, including different cell types that are present in a tumor environment. Tumor cells include cancer cells but also non-transformed host cells, or tumor-associated stroma cells. Examples of tumor-associated stroma cells include myeloid cells, in particular, tumor-associated macrophages.

Preferably, the above-described method may further comprise one or more of the following steps of:
  selectively targeting and/or visualizing MMR-positive TAMs linked to a hypoxic region of a solid tumor;
  determining a relative percentage of the MMR-positive TAMs, and optionally assessing the impact of a cancer therapy on the relative percentage of the MMR-positive TAMs.

Further, in still another aspect, the disclosure envisages a method of diagnosing cancer or prognosing cancer aggressiveness in a subject suffering from or suspected to suffer from cancer comprising the steps of:
  administering to the subject an immunoglobulin single variable domain of the disclosure, and
  determining the presence and/or relative percentage of MMR-positive TAMs in the subject, and
  diagnosing cancer or prognosing cancer aggressiveness in the subject according to the relative percentage of the MMR-positive TAMs.

In particular embodiments, the method comprises the steps of (i) providing a sample from the individual comprising cancer cells or suspected to comprise cancer cells; (ii) determining in the sample the presence and/or relative percentage of MMR-positive TAMs; (iii) classifying the individual as having a good/prognosis or diagnosing the individual as having cancer according to the results of step (ii).

A sample may comprise any clinically relevant tissue sample, such as a tumor biopsy or fine needle aspirate, or a sample of bodily fluid, such as blood, plasma, serum, lymph, ascitic fluid, cystic fluid, urine or nipple exudate. The sample may be taken from a human, or, in a veterinary context, from non-human animals such as ruminants, horses, swine or sheep, or from domestic companion animals such as felines and canines. The sample may also be paraffin-embedded tissue sections. It is understood that the cancer tissue includes the primary tumor tissue as well as an organ-specific or tissue-specific metastasis tissue.

In the context of the disclosure, prognosing an individual suffering from or suspected to suffer from cancer refers to a prediction of the survival probability of individual having cancer or relapse risk which is related to the invasive or metastatic behavior (i.e., malignant progression) of tumor tissue or cells. As used herein, "good prognosis" means a desired outcome. For example, in the context of cancer, a good prognosis may be an expectation of no recurrences or metastasis within two, three, four, five years or more of initial diagnosis of cancer. "Poor prognosis" means an undesired outcome. For example, in the context of cancer, a poor prognosis may be an expectation of a recurrence or metastasis within two, three, four, or five years of initial diagnosis of cancer. Poor prognosis of cancer may indicate that a tumor is relatively aggressive, while good prognosis may indicate that a tumor is relatively nonaggressive.

As used herein, the terms "determining," "measuring," "assessing," and "assaying" are used interchangeably and include both quantitative and qualitative determinations. In particular, ways to determine the presence and/or relative percentage of TAM subpopulations, in particular, MMR-positive TAMs, are known to the person skilled in the art, for example, by using flow cytometry, and is illustrated into more detail, but without the purpose of being limitative, e.g., in US2011/0262348 and in Movahedi et al. 2010, *Cancer Res.* 70:5728-39, all incorporated herein by reference).

Next, it is commonly known that finding tumor-specific markers for antibody-based targeting remains a difficult task. This is especially true when targeting the tumor stroma, since stromal antigens are typically not restricted to tumors. This may hamper the usefulness of these tools both for diagnostic and therapeutic applications. Therefore, it will often be desired to block extratumoral binding sites without competing for free binding sites in the tumor.

According to a preferred embodiment, any of the above-described methods for in vivo imaging, diagnosis/prognosis or treatment of cancer may comprise an additional step of co-administering a monovalent labeled immunoglobulin single variable domain according to the disclosure and an unlabeled bivalent form of an immunoglobulin single variable domain directed against the same target (macrophage mannose receptor) to block extratumoral binding sites. According to a preferred embodiment, the unlabeled bivalent form of the anti-MMR immunoglobulin single variable domain may comprise two identical or two different immunoglobulin single variable domains, as long as at least one of the immunoglobulin single variable domains is directed against the same target (macrophage mannose receptor). As used herein, "unlabeled" refers to the absence of a detectable label, in particular, a radio-isotope or radioactive tracer as defined hereinbefore. It should be clear that this does not exclude the absence of another modification (as defined hereinbefore).

A further aspect of the disclosure relates to a method for producing an immunoglobulin single variable domain according to the disclosure or a polypeptide comprising an immunoglobulin single variable domain according to the disclosure, the method comprising the steps of:
 expressing, in a suitable host cell or expression system, a nucleic acid sequence encoding an immunoglobulin single variable domain or a polypeptide comprising an immunoglobulin single variable domain according to the disclosure; and, optionally
 isolating and/or purifying the immunoglobulin single variable domain or the polypeptide.

Suitable expression systems include constitutive and inducible expression systems in bacteria or yeasts, virus expression systems, such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris*, and the like. Suitable animal host cells include HEK 293, COS, S2, CHO, NSO, DT40 and the like. The cloning, expression and/or purification of the immunoglobulin single variable domains can be done according to techniques known by the skilled person in the art.

The following examples more fully illustrate preferred features of the disclosure, but are not intended to limit the disclosure in any way. Those having ordinary skill in the art and access to the teachings herein will recognize additional modifications and embodiments within the scope thereof. Therefore, the disclosure is limited only by the claims attached herein. All of the starting materials and reagents disclosed below are known to those skilled in the art, and are available commercially or can be prepared using well-known techniques.

EXAMPLES

Material and Methods to the Examples

Mice and Cell Lines

Female Balb/c and C57BL/6 mice for biodistribution experiments in naïve animals were purchased from Harlan. C57BL/6 MMR-deficient mice were provided by Etienne Pays (Université Libre de Bruxelles). All animal studies were approved by and performed according to the guidelines of the institutional review board. The 3LL-R clone of the C57BL/6 Lewis Lung Carcinoma was injected subcutaneously (sc) in the flank ($3 \times 10^6$ cells). 12-14 days after inoculation, 3LL-R tumor-bearing mice were imaged.
Generation of Anti-Human MMR and Anti-Human/Mouse MMR Cross-Reactive sdAbs.

The anti-human macrophage mannose receptor (MMR) and anti-human/mouse MMR cross-reactive sdAbs (Nbs) were isolated from an immune phage library in a similar way as described before (Saerens et al. 2008, *Current Opin. Pharmacol.* 8:600-608; Saerens et al. 2004, *J. Biol. Chem.* 279:51965-72; Saerens et al. 2008, *Immunol. Methods* 329: 138-50). However, in order to generate cross-reactive Nbs, an alternating immunization schedule was carried out. An alpaca (*Vicugna pacos*) was immunized with 100 μg human MMR (R&D Systems #2534) followed by 100 μg mouse MMR (R&D Systems #2535) one week later. This alternating schedule was maintained for a total of 6 weeks and both proteins were mixed with the Gerbu adjuvant before injection. After immunization, blood was collected and the peripheral blood lymphocytes were isolated. mRNA was extracted from these cells using TRIzol (Invitrogen) and was reverse-transcribed with oligo(dT) and SUPERSCRIPT® II RT (Invitrogen), following the manufacturer's instructions. The gene sequences encoding the variable domains (VHHs) were PCR amplified, with the leader sequence-specific CALL001 (5'-GTC CTG GCT CTC TTC TAC AAG G-3'; SEQ ID NO: 257) and CH2 exon-specific CALL002 (5'-GGT ACG TGC TGT TGA ACT GTT CC-3; SEQ ID NO: 258) primers. After 1% agarose gel separation, the 600 bp fragment VHH—CH2 fragment was isolated from gel and re-amplified using the nested primers A6E (5'-GAT GTG CAG CTG CAG GAG TCT GGR GGA GG-3'; SEQ ID NO: 259) and PMCF (5'-CTA GTG CGG CCG CTG AGG AGA CGG TGA CCT GGG T-3; SEQ ID NO: 260), specific for the framework-1 and framework-4 regions, respectively. These PCR fragments were ligated into the phagemid vector pMECS, a variant of pHEN4 (Arbabi Ghahroudi et al. 1997, *FEBS Lett.* 414:521-6), after digestion with the PstI and NotI restriction enzymes. The pMECS differs from the pHEN4 in coding for a HA (YPYDVPDYGS; SEQ ID NO: 261) and 6× histidine tag fusion at the C-terminus of the Nb instead of a HA tag only fusion. Ligated material was transformed in freshly prepared E. coli TG1 cells and plated on LB plates with ampicillin. The colonies were scraped from the plates, washed and stored at −80° C. in LB-medium supplemented with glycerol (50% final concentration). Using M13VCS helper phage infection, the VHH library was expressed on phages. Specific sdAb phages were enriched by several consecutive rounds of in vitro selection on antigen coated to wells of microtiter plates (Nunc). For isolation of human/mouse MMR cross-reactive Nbs, screening was performed using human and mouse MMR alternatingly. Bound phage particles were eluted with 100 mM triethylamine (pH 11.0), immediately neutralized with 1 M Tris-HCl (pH 7.4) and used to infect E. coli TG1 cells. Individual colonies were picked and expression of recombinant sdAb-M13 protein III by addition of 1 mM isopropyl-β-D-thiogalac-topyranoside (IPTG). The periplasmic extract of each clone was subsequently tested in ELISA for human MMR recognition with non-specific antigen coated wells serving as a negative control. Human/mouse MMR cross-reactive Nbs were also screened in a similar fashion against mouse MMR, only clones reactive with both human and mouse antigens were withheld as cross-reactive Nbs. Each ELISA was performed on plates coated with 1 µg/ml MMR in 100 mM NaHCO$_3$ buffer pH=8.8. After coating the plates are washed with PBS+0.05% TWEEN®-20 (PBST) and blocked for 2 hours with PBS+0.05% TWEEN® 20+2% non-fat dry milk powder (Nestle) (PBSM). The PE extracts are then incubated for 1 hour on the plate and then washed with PBST followed by 1 hour incubation of 0.5 µg/ml mouse anti-HA tag antibody (16B12, Covance) in PBSM. After washing with PBST, 1.5 µg/ml alkaline phosphatase conjugated anti-mouse antibody (Sigma) in PBSM in added to the plate for 1 hour followed by PBST washing. Finally, the ELISA is developed using 2 mg/ml alkaline phosphatase substrate (Sigma) in AP-buffer (100 mM NaCl, 50 mM MgCl$_2$, 100 mM Tris pH=9.5) and the optical density signal at 405 nm is measured.

Expression and Purification of Anti-Human MMR and Anti-Human/Mouse MMR Cross-Reactive sdAbs The pMECS-Nb plasmids of the clones that scored positive in ELISA were transformed into E. coli WK6 cells. These cells stop translation at the TAG codon and, therefore, express the Nbs without a phage protein fusion. Production of recombinant VHH was performed in shaker flasks by growing the bacteria in Terrific Broth supplemented with 0.1% glucose and ampicillin until an absorbance at 600 nm between 0.6 and 0.9 was reached. VHH expression was then induced with 1 mM IPTG for 16 hours at 28° C. After pelleting the cells, the periplasmic proteins were extracted by osmotic shock. This periplasmic extract was loaded on a nickel-nitrilotriacetic acid (Thermo Scientific), and after washing, the bound proteins were eluted in PBS with 500 mM imidazole. The eluted fraction was dialyzed to VIVAS-PIN® 2 centrifugal concentrators (Sartorius). The final purity of the protein was checked by SDS-PAGE. The final yield was determined from UV absorption at 280 nm using the calculated theoretical extinction coefficient of the VHH.

Figure 4:
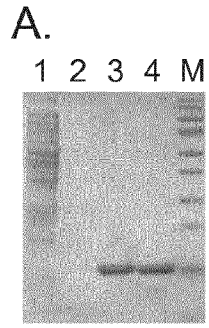
FIG. 4: Purification of a number of selected Nb clones. Panel A: Coomassie stained 12% SDS-PAGE gel loaded with protein fractions after IMAC purification of NbhmMMRm5.38 periplasmic extract. Lane 1, column flow-through, lane 2, wash fraction, lane 3 and 4, elution fractions, M indicates a molecular weight ladder. Panel B: Chromatogram of IMAC purified Nb5.38 samples run on a S75 gel-filtration column in PBS. Solid line depicts the OD 280 nm dotted line depicts conductivity, dashed line depicts pH. Only fractions in the main Nb peak around fraction 30 were withheld for further experiments. Panel C: Coomassie stained 12% SDS-PAGE gel loaded with protein fractions after gel-filtration of NbhmMMRm3.1 (lane 1), NbhmMMRm14.4 (lane 2), NbhmMMRm5.38 (lane 3), NbhmMMRm26.70 (lane 4) and NbhmMMRm3.49 (lane 5). M indicates a molecular weight ladder. All Nbs were confirmed to be >95% pure and have sizes of 13-15 kDa.
Figure 4:
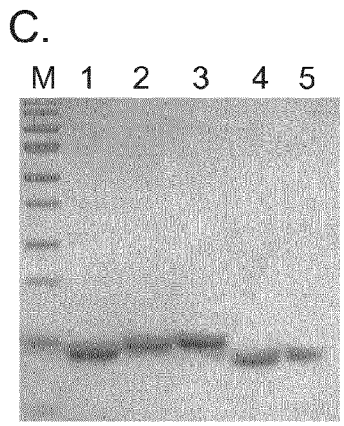
Figure 4:
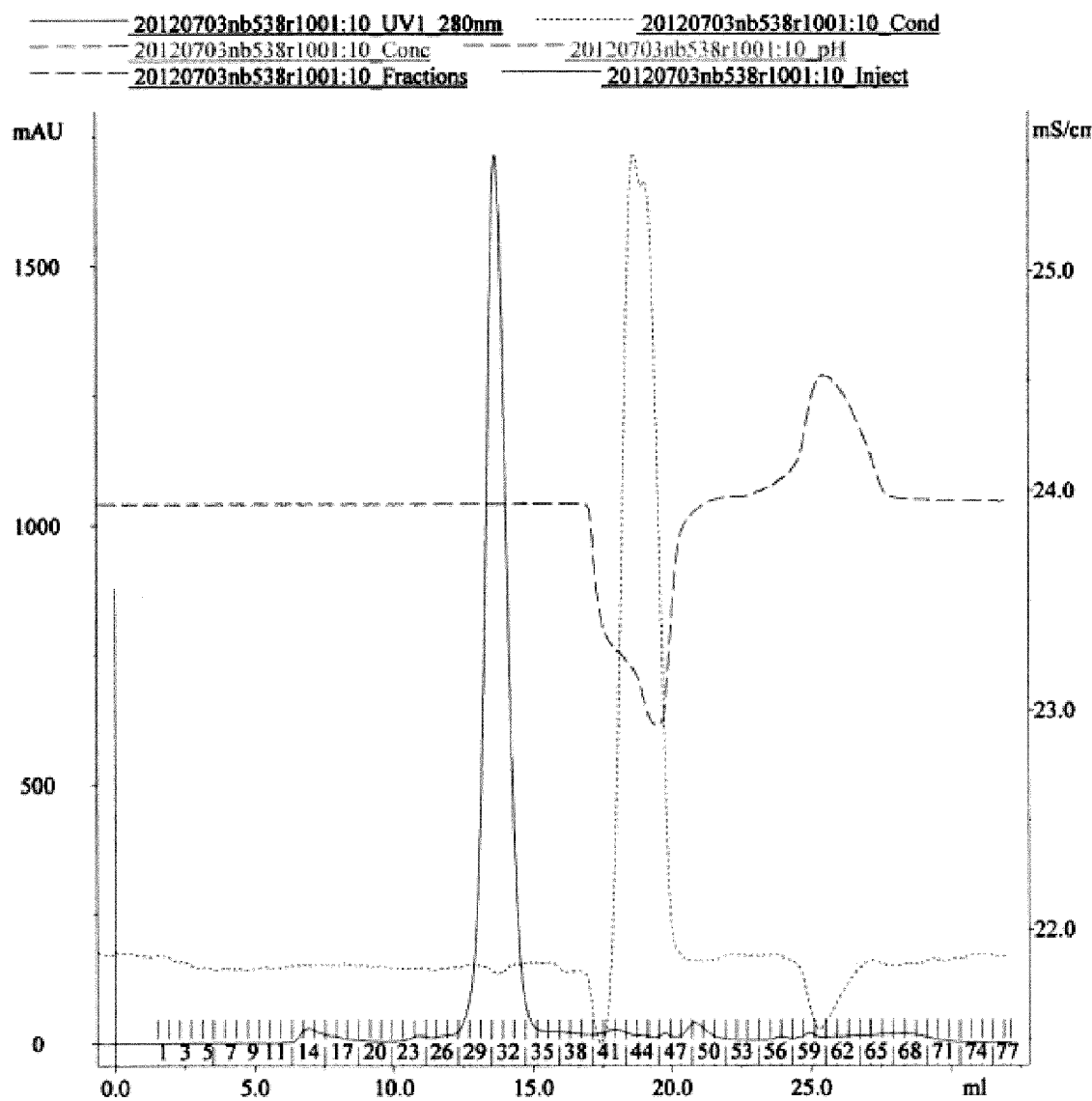

A HA tag is useful for detection of sdAbs via flow cytometry, but has been shown to interfere with 99mTc labeling on adjacent His tags. Therefore, for experimental tests involving 99mTc labeling, the sdAbs were recloned to the pHEN6c vector. This removes the HA tag and only fuses a 6×His tag at the C-terminus of the sdAb. In addition, after periplasmic expression and IMAC purification, sdAbs to be used in experiments involving 99mTc labeling were subjected to an additional purification step via size exclusion chromatography (SEC) on Superdex 75 HR 10/30 (Pharmacia, Gaithersburg, Md.) in phosphate buffered saline pH 7.4 (PBS) (FIG. 4, Panels B and C).

Surface Plasmon Resonance

Affinity analysis was performed using a BIAcore™ T100 (GE Healthcare) with HEPES-buffered saline running buffer (10 mM HEPES with 0.15 M NaCl, 3.4 mM EDTA and 0.005% surfactant P20 at pH 7.4). MRR was immobilized on a CM5 chip in acetate buffer 50 mM (pH 5.0), resulting in 2100 RU MMR coated on the chip. A second channel on the same chip was activated/deactivated in a similar way and served as a negative control. The MMR sdAbs were used as analytes in eleven different concentrations, ranging from 1 to 2000 nM, at a flow rate of 10 ml/minute. Glycine-HCl 50 mM (pH 2.0) was used for elution. The kinetic and equilibrium parameters (kd, ka and $K_D$) values were calculated from the combined sensogram of all concentrations using BIAcore™ T100 evaluation software 2.02 (GE Healthcare).

Cell Preparation and Flow Cytometry

The sdAbs used for flow cytometry staining were produced from the original pMECS phage vector and, therefore, each sdAb possesses a C-terminal HA and 6×His tag.

For examining specific binding of the anti-MMR sdAbs to mouse MMR, 3LL-R tumors were induced by injecting 3E6 cancer cells subcutaneously in C57Bl/6 mice. After 15 days of tumor growth, the tumors were isolated, chopped and incubated for 25 minutes (37° C.) with 10 U/ml Collagenase type I, 400 U/ml Collagenase type IV, and 30 U/ml DNAseI (Worthington). Density gradients (Axis-Shield) were used to remove tissue debris and dead cells. sdAbs were added at 10 µg/ml to 1E6 cells per tube. After at least one hour of incubation with anti-MMR sdAb or control sdAb, cells were washed two times with ice-cold Hank's Buffered Salt Solution (HBSS) buffer (containing 0.74 g/l EDTA and 0.5% (v/v) heat inactivated fetal calf serum) and incubated with 0.5 µg/ml ALEXA FLUOR®-488 conjugated anti-HA tag monoclonal antibody (clone 16B12, Invitrogen). Commercial antibodies used for cell surface stainings were ALEXA FLUOR®-647 conjugated anti-mouse Ly6C monoclonal antibody (clone ER-MP20, AbD Serotec), PerCPCy5.5 conjugated anti-mouse MHCII monoclonal antibody (clone M5/114.15.2, Biolegend), Phycoerythrin conjugated anti-mouse Ly6G monoclonal antibody (clone 1A8, BD Biosciences). For flow cytometry measurements, CD11b+Ly6G tumor-associated macrophages were further gated on MHCII expression, as the MHCII$^{low}$ TAMs express MMR to a high degree. Binding profiles of anti-MMR sdAbs were recorded.

In order to examine binding of the sdAbs to human MMR, human immature dendritic cells were used. Cryopreserved immature dendritic cells derived from healthy human donor monocytes were a kind gift of Dr. Karine Breckpot (Vrije Universiteit Brussel, Jette, Belgium). To prepare the immature dendritic cells, peripheral blood mononuclear cells were removed from the blood via leukapheresis and monocytes were separated by adherence to plastic NUNCLON® dishes (NUNC®, Biotech Line, Slangerup, Denmark). After removal of the non-adherent cells, immature dendritic cells were in vitro generated during a six days differentiation from monocytes in RPMI 1640 medium supplemented with 500 U/ml IL-4 (Invitrogen) and 1000 U/ml GM-CSF (Gentaur). Cells were harvested at day 6, counted and aliquoted at 1E7 cells/vial. The cells were cryopreserved in 85% autologous serum, 10% DMSO (Sigma-Aldrich) and 5% Glucosteril 40% (Fresenius, Albertslund, Denmark). For flow cytometry analysis, cells were thawed on ice and incubated for more than one hour at room temperature with precooled RPMI 1640 medium supplemented with 500 U/ml IL-4 (Invitrogen) and 1000 U/ml GM-CSF (Gentaur). Next, 10% normal rabbit serum was added to prevent aspecific Fc-mediated binding of antibodies. After half an hour, the sdAbs were added at 10 µg/ml to 2E5 cells per tube. After at least one hour of incubation with anti-MMR sdAb or control sdAb, cells were washed two times with ice-cold HBSS buffer supplemented with 1% normal rabbit serum (Eppendorf 5810-R Centrifuge, 8 minutes, 1400 rpm, 4° C.) and incubated with 0.5 µg/ml ALEXA FLUOR®-488 conjugated anti-HA tag monoclonal antibody (clone 16B12, Invitrogen). Allophycocyanin conjugate (APC) conjugated anti-human CD11c monoclonal antibody (clone B-ly6, BD Biosciences) was used for CD11c staining. Stained cells were washed once more with ice-cold HBSS buffer supplemented with 1% normal rabbit serum (EPPENDORF® 5810-R Centrifuge, 8 minutes, 1400 rpm, 4° C.) and analyzed by flow cytometry.

sdAb Labeling and In Vitro Characterization of $^{99m}$Tc-Labeled sdAbs sdAbs were labeled with $^{99m}$Tc at their hexahistidine tail. For the labeling, $[^{99m}Tc(H_2O)_3(CO)_3]^+$ was synthesized by adding 1 mL of $^{99m}TcO_4^-$ (0.74-3.7 GBq) to an Isolink kit (Mallinckrodt Medical BV) containing 4.5 mg of sodium boranocarbonate, 2.85 mg of sodium tetraborate, $10H_2O$, 8.5 mg of sodium tartrate, $2H_2O$, and 7.15 mg of sodium carbonate, pH 10.5. The vial was incubated at 100° C. in a boiling bath for 20 minutes. The freshly prepared $[^{99m}Tc(H_2O)_3(CO)_3]^+$ was allowed to cool at room temperature for 5 minutes and neutralized with 125 µL of 1 M HCl to pH 7-8. $[^{99m}Tc(H_2O)_3(CO)_3]^+$ was added to 50 µL of 1 mg/mL monovalent sdAb or 2 mg/ml bivalent sdAb, together with 50 µL of carbonate buffer, pH 8. The mixture was incubated for 90 minutes at 52° C. in a water bath. The labeling efficiency was determined by instant thin-layer chromatography in acetone as mobile phase and analyzed using a radiometric chromatogram scanner (VCS-201; Veenstra). When the labeling yield was less than 90%, the $^{99m}$Tc-sdAb solution was purified on a NAP-5 column (GE Healthcare) pre-equilibrated with phosphate-buffered saline (PBS) and passed through a 0.22 µMillipore filter to eliminate possible aggregates.

Pinhole SPECT-microCT Imaging Procedure

Mice were intravenously injected with 100-200 µl 45-155 MBq (about 5-10 µg) of $^{99m}$Tc-sdAb, with or without an excess of concentrated monovalent or bivalent unlabeled sdAb. Mice were anesthetized with a mixture of 18.75 mg/kg ketamine hydrochloride (Ketamine 1000®, CEVA, Brussels, Belgium) and 0.5 mg/kg medetomidin hydrochloride (DOMITOR®, Pfizer, Brussels, Belgium) 10-15 minutes before pinhole SPECT acquisition.

MicroCT imaging was followed by pinhole SPECT on separate imaging systems. MicroCT was performed using a dual source CT scanner (SKYSCAN® 1178, Skyscan, Aartselaar, Belgium) with 60 kV and 615 mA at a resolution of 83 µm. The total body scan time was 2 minutes. Image reconstruction was performed using filtered backprojection (Nrecon, SKYSCAN®, Aartselaar, Belgium). Total body pinhole SPECT was performed at 60 minutes or 180 minutes post-injection (p.i.) using a dual headed gamma camera (e.cam$^{180}$ Siemens Medical Solutions, IL, USA), mounted with two multi-pinhole collimators (3 pinholes of 1.5 mm in each collimator, 200 mm focal length, 80 mm radius of rotation). Images were acquired over 360 degrees in 64 projections of 10 s into 128×128 matrices resulting in a total imaging time of 14 minutes. The SPECT images were reconstructed using an iterative reconstruction algorithm (OSEM) modified for the three pinhole geometry and automatically reoriented for fusion with CT based on six $^{57}$Co landmarks.

Image Analysis

Image viewing and quantification was performed using AMIDE Medical Image Data Examiner software. Ellipsoid regions of interest (ROIs) were drawn around the tumor and major organs. Uptake was calculated as the counts in the tissue divided by the injected activity counts and normalized for the ROI size (% IA/cm$^3$). High-resolution image 3D-reconstructions were generated using OsiriX Imaging Software.

Biodistribution Analysis 30 minutes after microCT/SPECT acquisition, mice were sacrificed with a lethal dose of pentobarbital (NEMBUTAL®; CEVA). Tumor, kidneys, liver, lungs, muscle, spleen, lymph nodes, bone, heart, and blood were removed and weighed, and the radioactivity was measured using an automated γ-counter (Cobra II Inspector 5003; Canberra-Packard). Tissue and organ uptake was calculated as percentage of injected activity per gram of tissue (% IA/g), corrected for decay.

Statistics

Statistical significance was determined by the Student's t test, using Microsoft EXCEL® or GRAPHPAD Prism™ 4.0 software. Differences were considered significant when $P \leq 0.05$. Geometric means and confidence intervals were determined using Microsoft EXCEL®.

Where multiple comparisons are made (9-10 different organs), the p-values of the student's t test were adjusted by Holm's procedure (Holm 1979, *Scand. J. Stat.* 6:65-70). The R environment (Ihaka and Gentleman 1996, *J. Comput. Graph. Stat.* 5:299-314) and the multitest package (Pollard et al. 2011, available from World Wide Web CRAN.Rprojectorg/package=multtest) were used for statistical analyses and figures. The significance of the student t tests and corrections for multiple testing was set to 0.05.

Example 1

Relevance of MMR as a Marker for Tumor-Promoting TAMs in Human Tumors

In order to test the relevancy of MMR as a marker for tumor-promoting TAMs in human tumors, MMR and CD68 (as human macrophage marker) expression in paraffin-embedded sections of human breast cancer samples (VUB-UZ Brussel) was assessed. Using immunohistochemistry on consecutive slides of the same specimen and one double staining on a single slide, the presence of CD68-positive macrophages in both tumor and fibrotic foci within the tumor region was demonstrated. Immunostaining for MMR clearly shows that the macrophages found in fibrotic foci do co-express MMR (data not shown). Since fibrotic foci within the tumor region is known to be a marker of hypoxia and worse prognosis (Colpaert et al. 2003, *Breast Cancer Res. Treat.* 81:137-47), the presence of MMR$^+$ macrophages could function as an indicator of severe hypoxia in human tumors as well, similar to what was shown before for mouse tumors (US2011/0262348). In conclusion, these studies shows that in human breast cancer samples, MMR$^+$ TAMS are clearly detected and are enriched in fibrotic foci which are known to be a marker for intratumoral hypoxia and correlate with a poor prognosis.

Example 2

Selection of Anti-Human MMR Nbs

Anti-human MMR sdAbs were generated (see Material and Method section). After four panning rounds of an anti-human/anti mouse MMR phage bank on human MMR, up to 100-fold enrichments for hMMR reactive phages were observed per panning round. Therefore, 188 colonies from all rounds were selected for PE-expression. These PE-extracts were used in PE-ELISAs to determine which clones react effectively to hMMR. In total 100 clones were selected based on these results (FIG. 1). Additionally, the DNA and protein sequence of the selected clones was determined (Table 1) and double clones or premature stopping clones were discarded.

Example 3

Selection of Anti-Human/Mouse MMR Cross-Reactive Nbs

Figure 2:
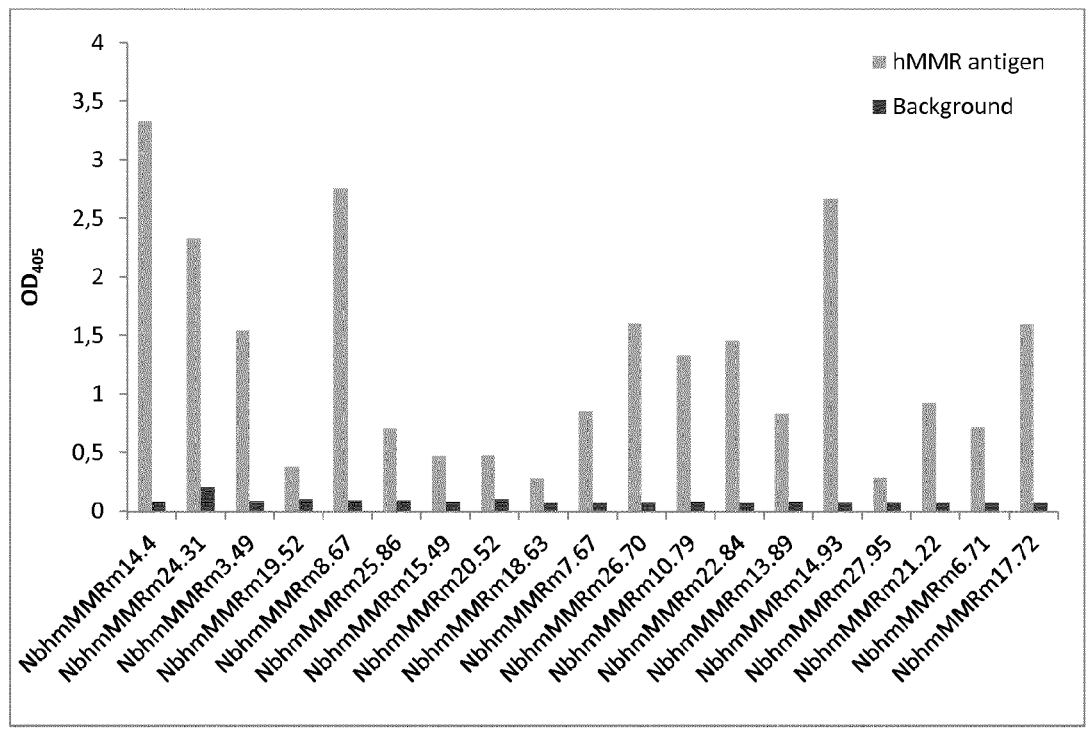
FIG. 2: PE-ELISA on human MMR. Summary of the selected anti-human/mouse MMR cross-reactive Nb clones. A clone was selected when the OD 405 nm was at least three times higher on specific antigen as compared to irrelevant milk-blocking proteins.
Figure 3:
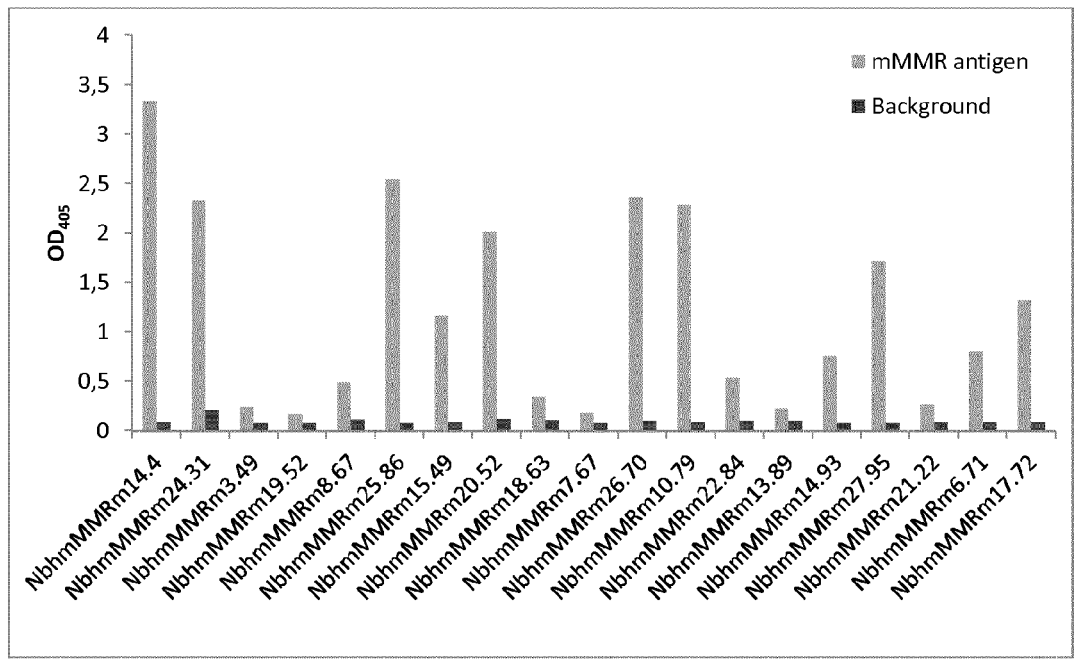
FIG. 3: PE-ELISA on mouse MMR. Summary of the selected anti-human/mouse MMR cross-reactive Nb clones. A clone was selected when the OD 405 nm was at least two times higher on specific antigen as compared to irrelevant milk-blocking proteins.

Next, anti-human/mouse MMR cross-reactive sdAbs were generated (see also Material and Method section). The anti-human/anti mouse MMR phage bank was alternatingly screened on human and mouse MMR for a total of four rounds, resulting in up to 100-fold enrichments for hMMR/mMMR reactive phages from the second panning round. Therefore, 188 colonies from the second and third rounds were selected for PE-expression. These PE-extracts were used in PE-ELISAs to determine which clones react effectively to MMR, clones were selected after the ELISA on hMMR (FIG. 2). These clones were then screened for binding on mouse MMR (FIG. 3). Only clones (42) that reacted to both antigens were withheld as true cross-reactive Nbs. These clones were sequenced (Table 2) and divided into families based on their CDR3 regions.

Example 4

Production of Representative Set of Anti-Human or Anti-Human/Mouse MMR Nbs

A set of representative clones was selected for Nb production in E. Coli: (1) anti-human Nbs: NbhMMRm1.33, NbhMMRm10.19, NbhMMRm23.30, NbhMMRm2.15, NbhMMRm3.1, NbhMMRm5.38, NbhMMRm12.6, NbhMMRm11.5, NbhMMRm15.43, NbhMMRm16.95; (2) anti-human/mouse Nbs: NbhMMRm14.4, NbhMMRm6.71, NbhMMRm24.31, NbhMMRm20.52, NbhMMRm3.49, NbhMMRm22.84, NbhMMRm19.52, NbhMMRm21.22, NbhMMRm14.93, NbhMMRm15.49, NbhMMRm17.72, NbhMMRm10.79, NbhMMRm7.67, NbhMMRm4.83. Each clone was grown in a two liter culture. After expression and osmotic shock, the resulting extract was purified on 1 ml of Ni-NTA resin. The resulting 5 ml of eluted Nb was dialyzed to PBS after which the concentration was determined using a Nanodrop device and purity was assessed on Coomassie stained SDS-PAGE gels. The sdAbs all produced between 0.7 and 9 mg Nb/l E. coli culture (Table 3).

Example 5

Determination of Kinetic Rate Constants of a Representative Set of Anti-Human or Anti-Human/Mouse MMR Nbs Via Surface Plasmon Resonance (SPR)

Figure 5:
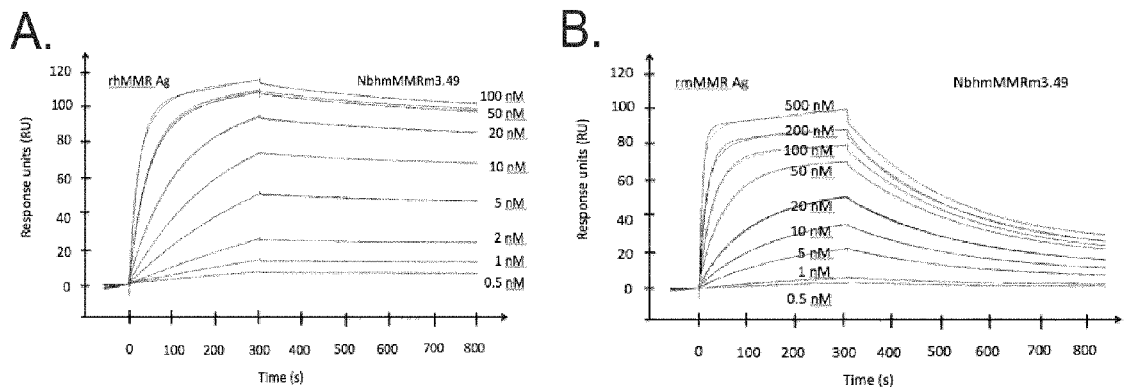
FIG. 5: Surface Plasmon resonance sensograms of NbhmMMRm3.49 binding to recombinant human and mouse MMR. NbhmMMRm3.49 was injected in multiple concentrations at 30 µl/minute over a CM5 sensor chip coated with 3500 RU of recombinant human (Panel A) or mouse (Panel B) MMR. The sonograms depict the association and dissociation phase over a period of 800 seconds.

The binding characteristics and affinity of selected Nbs towards the recombinant hMMR and recombinant mMMR antigen was examined in further detail using surface plasmon resonance. A combined sensogram was recorded for each Nb (example for NbhmMMRm3.49 in FIG. 5) and the kinetic and equilibrium parameters (kd, ka and KD) values were calculated (Table 4 and Table 5). Most but not all results on binding to mouse or human rMMR obtained via this SPR analysis are in agreement with the results obtained by PE-ELISA.

Based on the kinetic and equilibrium parameters (kd, ka and KD) values five among the cross-reactive anti-hmMMR Nbs were selected for further analysis (indicated in bold in Table 4 and Table 5). These five Nbs (NbhmMMRm3.1, NbhmMMRm14.4, NbhmMMRm5.38, NbhmMMRm26.70 and NbhmMMRm3.49) displayed rather low dissociation rate constants, which makes them suitable for in vivo imaging. The corresponding KD values for these sdAbs ranged from 68 nM to 2 nM. It can clearly be seen from the data in Tables 4 and 5 that the Nbs have a preferred MMR antigen: NbhmMMRm3.1, NbhmMMRm14.4, NbhmMMRm5.38 and NbhmMMRm3.49 have a higher affinity for the hMMR Ag compared to the mMMR Ag. In contrast, NbhmMMRm26.70 binds better to mMMR Ag as compared to hMMR Ag, even though the first rounds of immunization and panning were performed using the hMMR antigen.

Example 6

Determination of Binding of a Representative Set of Anti-Human or Anti-Human/Mouse MMR Nbs on MMR Expressed on Cells Via Flow Cytometry In order to confirm the binding specificity of the five selected Nbs to MMR expressed on cells, flow cytometric analysis was performed.

Figure 6:
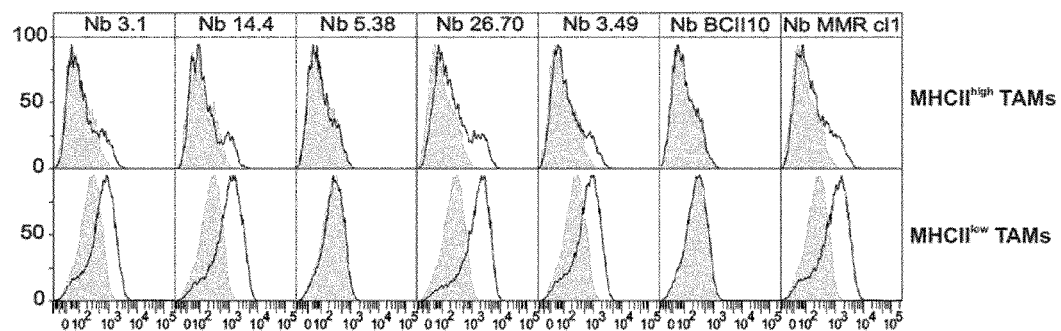
FIG. 6: MMR-specific Nbs bind to mouse MMR expressed on ex vivo isolated macrophages. 3LL-R tumors were induced by injecting 3×10$^6$ cancer cells subcutaneously in C57Bl/6 mice. After 15 days of tumor growth, the tumors were isolated and single cell suspensions were prepared to be analyzed by flow cytometry. The CD11b+ Ly6G tumor-associated macrophages (TAM) were further gated on MHCII expression. The histograms depict MMR expression as defined by Nb binding on MHCII$^{low}$ and MHCII$^{high}$ TAMs. Shaded histograms depict binding of the negative control Nb BCII10. The anti-mouse MMR sdAb clone 1 (SEQ ID NO: 247) was used as a positive control.

Binding to cell-expressed mouse MMR was determined on tumor-associated macrophages derived from a preclinical mouse tumor model, making use of the previously documented finding that TAMs contain molecularly and functionally distinct subsets differing in expression of MMR: MMR is highly expressed on MHC $II^{low}$ TAMs, whereas MMR expression is lower on MHC $II^{high}$ TAMs (Movahedi et al. 2010). As shown in FIG. 6, clear shifts in fluorescence intensity, comparable to the shift of the anti-mMMR Nb clone 1, could be detected on TAMs for NbhmMMRm3.1, NbhmMMRm14.4, NbhmMMRm26.70 and NbhMMRm3.49. Remarkably, binding of NbhmMMRm5.38 to TAMs could not be detected.

Figure 7:
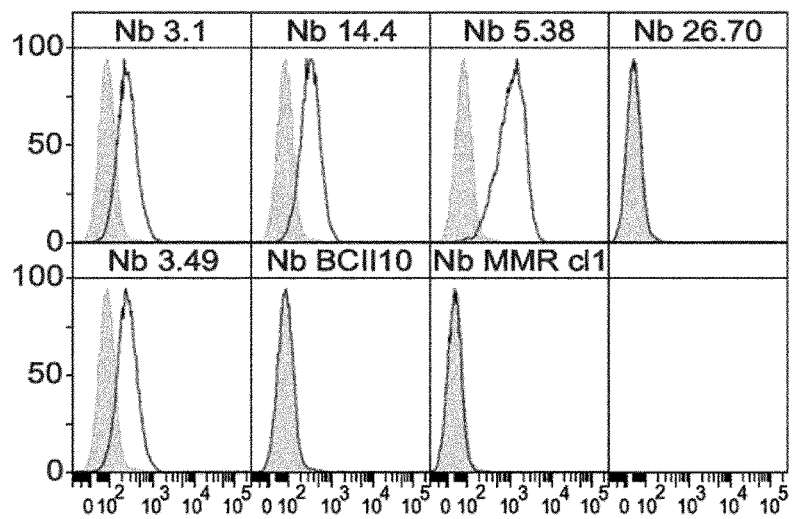
FIG. 7: MMR-specific Nbs bind to human MMR expressed on induced dendritic cells. Anti-hMMR Nbs bind to CD11c+ subsets in human iDC single-cell suspensions. Shaded histograms depict binding of the negative control Nb BCII10. As expected, the anti-mouse MMR sdAb clone 1 (SEQ ID NO: 247) does not bind to human MMR.

In order to investigate the binding specificity of the selected Nbs to human MMR, human immature monocyte-derived dendritic cells were generated and gated on $CD11c^+$ cells. As shown in FIG. 7, binding of NbhMMRm3.1, NbhmMMRm14.4, NbhmMMRm5.38 and NbhMMRm3.49 to hMMR expressed on immature dendritic cells was clearly detected, whereas no significant shift in fluorescence intensity could be detected for NbhmMMRm26.70.

Overall, the flow cytometry analysis indicates that NbhmMMRm5.38 binds on cell expressed human MMR, but not mouse MMR. In contrast, NbhmMMRm26.70 has a similar binding pattern to the original anti-mouse MMR clone 1 and binds to mouse but not human MMR. NbhMMRm3.1, NbhmMMRm14.4 and NbhmMMRm3.49 bind to both mouse and human MMR expressed on cells.

Example 7

Tissue Distribution Experiments with a Representative Set of Anti-Human or Anti-Human/Mouse MMR sdAbs in 3LL Tumor-Bearing Mice In a next step, assessing whether selected anti-human MMR Nbs could be used for in vivo targeting of MMR-expressing cells was desired. Since the flow cytometry analysis on human immature dendritic cells had revealed that NbhmMMRm26.70 does not bind to human MMR, it was not analyzed at this time. Since NbhmMMRm3.1 and NbhmMMRm3.49 share the same CDR3 loop, but Nbhm-MMRm3.49 has a better affinity for recombinant MMR as compared to NbhmMMRm3.1, among those two sdAbs, NbhmMMRm3.49 was selected for the in vivo targeting. Also NbhmMMRm14.4 and NbhmMMRm5.38 were included in the selection to be used for this example. Since the latter did not bind to mouse MMR according to the flow cytometric analysis, it could be used to exclude aspecific binding and accumulation in tissues.

Figure 8:
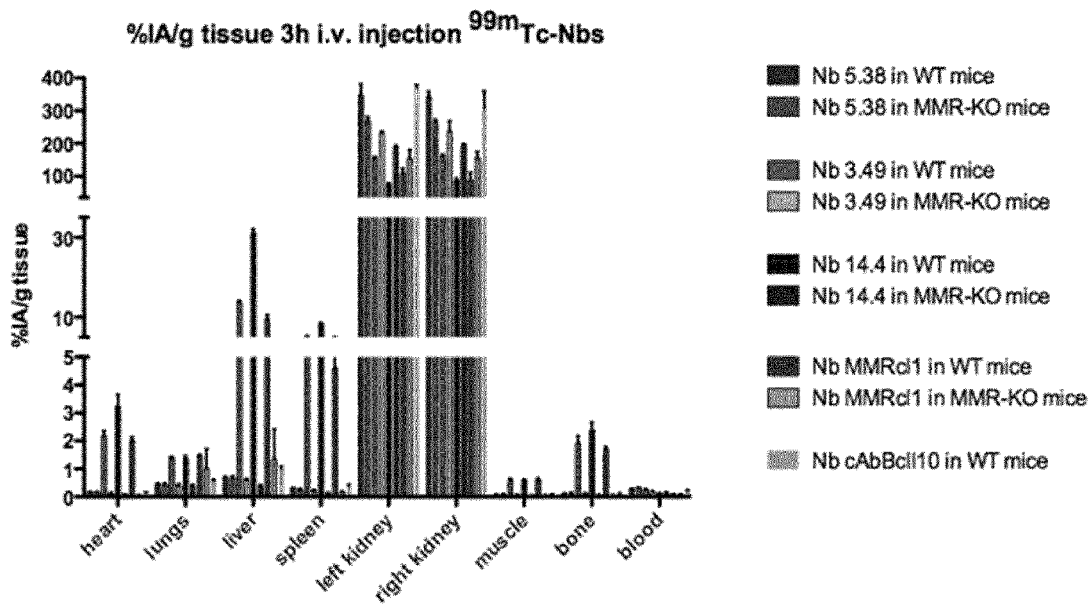
FIG. 8: Tissue distribution of MMR Nbs in WT versus MMR Knock-out C57/lb6 mice. Anti-MMR Nbs were labeled with $^{99m}$Tc and injected in the tail vein of C57/lb6 mice (n=3). After three hours, the mice were dissected and radioactivity was measured in the major organs. The uptake values for the negative control Nb cAbBcII10 served as a measure for general aspecific Nb distribution. The anti-mouse MMR sdAb clone 1 (SEQ ID NO: 247) was used as a positive control.

The selected sdAbs were labeled with $^{99m}$Tc and injected intravenously in 3LL tumor-bearing C57BL/6 mice. Three hours post-injection, the mice were dissected and radioactivity was measured in the major organs. As shown in FIG. 8, NbhmMMRm14.4 and NbhmMMRm3.49 exhibited a similar pattern of tissue distribution as the positive control anti-mouse MMR sdAb clone 1 (SEQ ID NO: 247), with high uptake in organs such as lungs, spleen and liver. Hereby, NbhmMMRm14.4 exhibited an even higher uptake in these organs as compared to NbhmMMRm3.49 and the anti-mouse MMR sdAb clone 1. In contrast, the negative controls NbhmMMRm5.38 and Nb cAbBcII10 mainly showed high tracer uptake in the kidneys, indicative of renal clearance. The MMR sdAbs were also inoculated in MMR knock-out mice where the uptake in liver and spleen dropped below 1% IA/g (FIG. 8). These data indicate that the accumulation of NbhmMMRm14.4, NbhmMMRm3.49 and the anti-mouse MMR sdAb clone 1 in organs such as liver and spleen is related to MMR expression and, therefore, reflects specific targeting to endogenous MMR expressed in these organs.

Figure 9:
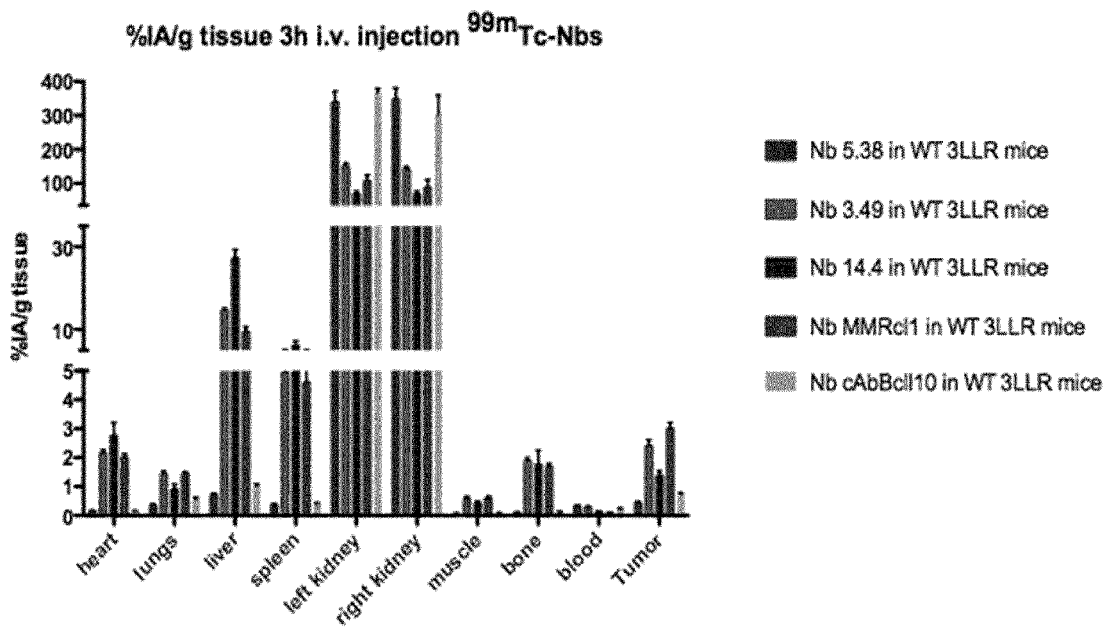
FIG. 9: Tissue distribution of MMR Nbs in 3LL tumor-bearing C57/lb6 mice. 3LL-R tumors were induced by injecting 3×10$^6$ cancer cells subcutaneously in C57Bl/6 mice. Anti-MMR Nbs were labeled with $^{99m}$Tc and injected in the tail vein of the mice (n=3). After three hours, the mice were dissected and radioactivity was measured in the major organs. The uptake values for the negative control Nb cAbBcII10 served as a measure for general aspecific Nb distribution. The anti-mouse MMR sdAb clone 1 (SEQ ID NO: 247) was used as a positive control.
Figure 10:
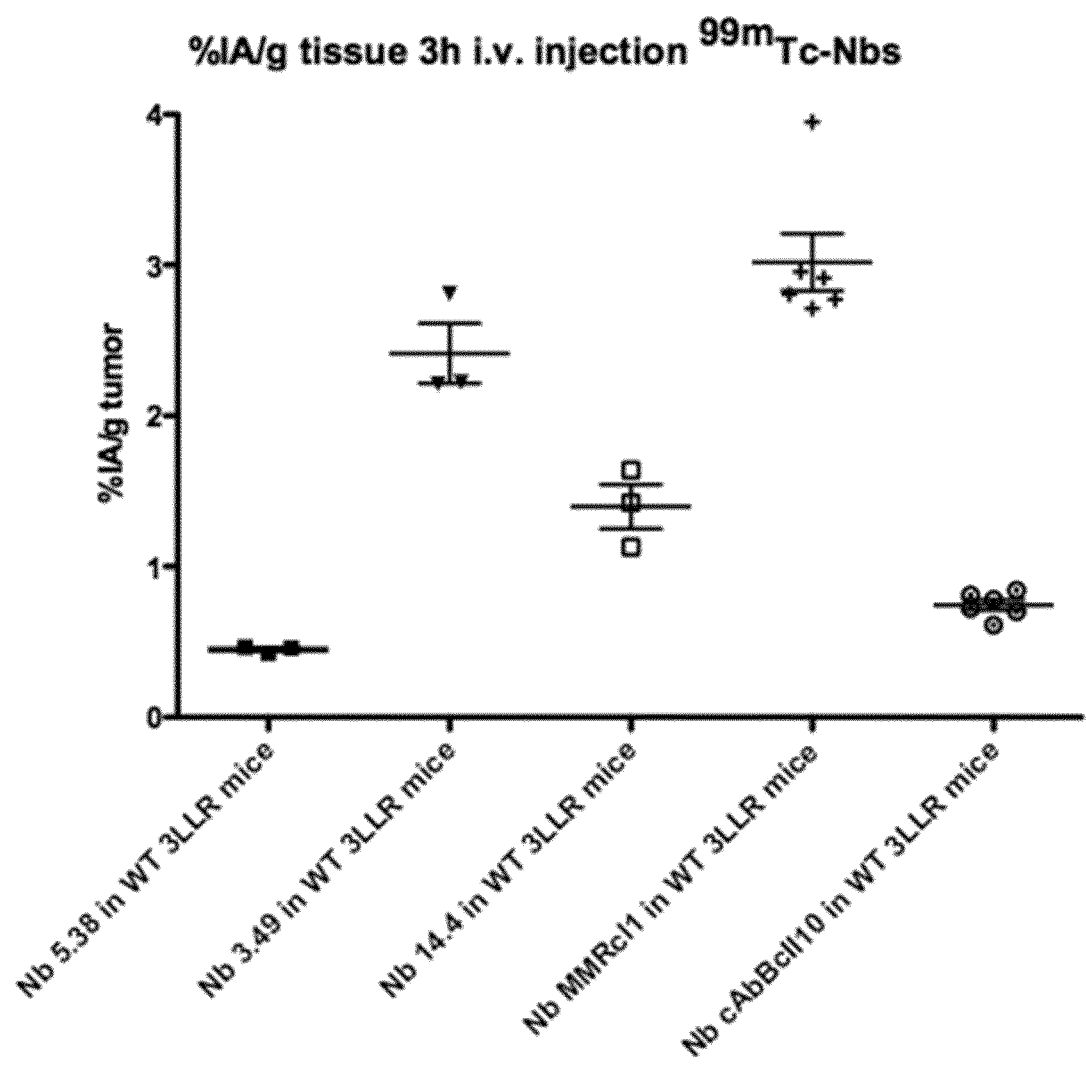
FIG. 10: Tumor targeting of MMR Nbs in 3LL tumor-bearing C57/lb6 mice. 3LL-R tumors were induced by injecting 3×10$^6$ cancer cells subcutaneously in C57Bl/6 mice. Anti-MMR Nbs were labeled with $^{99m}$Tc and injected in the tail vein of the mice (n=3). After three hours, the mice were dissected and radioactivity of the dissected tumor was measured. The uptake values for the negative control Nb cAbBcII10 served as a measure for general aspecific Nb distribution. The anti-mouse MMR sdAb clone 1 (SEQ ID NO: 247) was used as a positive control.

As shown in FIGS. 9 and 10, NbhmMMRm3.49 has similar tumor targeting potential as the positive control anti-mouse MMR sdAb clone 1 (SEQ ID NO: 247). Remarkably, the tumor-targeting potential of Nbhm-MMRm14.4, which showed enhanced targeting to endogenous MMR in organs such as liver and spleen, was lower as compared to NbhmMMRm3.49 or the anti-mouse MMR sdAb clone 1.

TABLE 1

Anti-human MMR Nbs selected after ELISA on human MMR of PE-extracts from single Nb clones isolated from phage display. In addition to the Nb sequence sensu strictu depicted here, all clones also carry a C-terminal extension containing a HA and 6xHis tag(AAAYPYDVPDYGSHHHHHH; SEQ ID NO: 262). FRs and CDRs are listed separately in Table 6.

| Name | SEQ ID NO: | Sequence |
|---|---|---|
| NbhMMRm3.1 | 8 | QVQLQESGGGLVQPGGSLRLSCAASGFTLDYYAIGWFRQAPGKEREGISCISYKGGSTTYADSVKGRFTISKDNAKNTAYLQMNNLKPEDTGIYYCAAGFVCYNYDYWGPGTQVTVSS |
| NbhMMRm5.38 | 10 | QVQLQESGGGLVQAGGSLRLSCAASGFTDDDYDIGWFRQAPGKEREGVSCISSSDGSTYYADSVKGRFTISSDNAKNTVYLQMNSLKPEDTAVYYCAADFFRWDSGSYYVRGCRHATYDYWGQGTQVTVSS |
| NbhMMRm1.33 | 11 | QVQLQESGGGLVQPGGSLRLSCAASGFTLDNYTVAWFRQAPGKEREGVSCISSSGGSTNYADSVKGRFTISRDNSKKSVYLQMNSLKPEDTAIYTCAAERAPPYYSGYYFFDSTCVAASYDYWGQGTQVTVSS |

TABLE 1-continued

Anti-human MMR Nbs selected after ELISA on human MMR of PE-extracts from single Nb clones isolated from phage display. In addition to the Nb sequence sensu strictu depicted here, all clones also carry a C-terminal extension containing a HA and 6xHis tag(AAAYPYDVPDYGSHHHHHH; SEQ ID NO: 262). FRs and CDRs are listed separately in Table 6.

| Name | SEQ ID NO: | Sequence |
|---|---|---|
| NbhMMRm10.19 | 12 | QVQLQESGGGLVQPGGSLKLSCAASGSIFSIKTMGWYRQAPGKQRELVAAITSGGSTNYADSVKGRFTISRDNAKNTVYLQMNSLKPEDTAVYYCNADGVVAWDQPYDNYWGQGTQVTVSS |
| NbhMMRm23.30 | 13 | QVQLQESGGGLVQAGDSLSISCAASGDTFNHYSWGWFRQAPGKAREFVAAISWNGGSKYADSVKGRFAISRDIAKNTVSLQMNSLEPEDTAVYYCAADRRPYNDWWDDWSWWVYWGQGTQVTVSS |
| NbhMMRm2.15 | 14 | QVQLQESGGGLVQPGESLRLSCKLSGFTLDYYDIGWFRQAPGKEREGVSCISSIGGSANYADSVKGRFTISRDNVKNTVYLQMNSLKPEDTAIYYCAAEAQTPYNDGDCTRASYDYWGQGIQVTVSS |
| NbhMMRm12.6 | 15 | QVQLQESGGGLVQPGGSLRLSCVVSGSFLSINHMGWYRQVSGEQRELVAAITSGGSTNYADSVKGRFTISRDSAKNTVYLQMNSLKPEDTAVYYCNADALTMLPPFDFWGQGTQVTVSS |
| NbhMMRm11.5 | 16 | QVQLQESGGGLVQPGGSLMLSCAASGNIFTINRMGWYRQAPGKQRELVAAITSGGNTNYADSVKGRFTISRDNAKNTVYLQMNSLKPEDTAVYYCNAAIVTMTSPYSDYWGQGTQVTVSS |
| NbhMMRm15.43 | 17 | QVQLQESGGTLVQPGGSLRLSCAASGSTFSINNMGWYRQAPGKQRELVAGITGGNTHYADSVKGRFTISRDNAKNTMYLQMNGLKPEDTAVYYCNANWGAYWGQGTQVTVSS |
| NbhMMRm16.95 | 18 | QVQLQESGGGLVQPGGSLGLSCAASGRIASISAMGWYRQAPGKQRELVAAITGSGRTNYADSVKGRFTISRDNAKNTVYLQMNSLKPEDTAVYYCNLLMVDYGLGLGTDYWGQGTQVTVSS |
| NbhMMRm4.83 | 19 | QVQLQESGGGLVQPGGSLRLSCAASGPGFKLDYYAIAWFRQAPGKEREGVSCIGGSGSGLTTYVENSVKDRFTISRDNAQNTVYLHMNSLKPEDTGIYYCAADTYYYCSKRVWRNDYGSWGQGTQVTVSS |

TABLE 2

Anti-human/mouse MMR cross-reactive Nbs selected after ELISA on human MMR and mouse MMR of PE-extracts from single Nb clones isolated from phage display.In addition to the Nb sequence sensu strictu depicted here, all clones also carry a C-terminalextension containing a HA and 6xHis tag(AAAYPYDVPDYGSHHHHHH; SEQ ID NO: 262). FRs and CDRs are listed separately in Table 6.

| Name | SEQ ID NO: | Sequence |
|---|---|---|
| NbhmMMRm3.49 | 7 | QVQLQESGGGLVQPGGSLRLSCAASGFSLDYYAIGWFRQAPGKEREGISCISYKGGSTTYADSVKGRFTISKDNAKNTAYLQMNSLKPEDTGIYSCAAGFVCYKYDYWGQGTQVTVSS |
| NbhmMMRm14.4 | 9 | QVQLQESGGGLVQAGDSLRLSCAASGRTFSINYMGWYRQAPGKQRELVAAITSGSGSINYADSVKGRFTISRTDNAKNMYLQMNSLKPEDTAVYYCNADMDSSLSGGYVDVWGQGTQVTVSS |

TABLE 2-continued

Anti-human/mouse MMR cross-reactive Nbs selected after ELISA on human MMR and mouse MMR of PE-extracts from single Nb clones isolated from phage display. In addition to the Nb sequence sensu strictu depicted here, all clones also carry a C-terminalextension containing a HA and 6xHis tag(AAAYPYDVPDYGSHHHHHH; SEQ ID NO: 262). FRs and CDRs are listed separately in Table 6.

| Name | SEQ ID NO: | Sequence |
|---|---|---|
| NbhmMM Rm6.71 | 20 | QVQEQESGGGLVQAGGSLRLSCAASGGTFDDSVIGWFRQAPGKEREGVSCISSNDGTTHYASPVKGRFTISSDNAKNTVYLQMNSLKPEDTAVYYCAAETPSIGSPCTSASYDYWGQGTQVTVSS |
| NbhmMM Rm24.31 | 21 | QVQLQESGGGLVQPGGSLRLSCTATGFTLKNHHIGWLRQAPGKEREGVASINSSGSTNYADSVQGRFTISRDNAKNTVFLQMNSLKSEDTAVYYCARLRRYYGLNLDPGSYDYWGQGTQVTVSS |
| NbhmMM Rm20.52 | 22 | QVQLQESGGGLVQAGGSLRLSCAASGRIFSAYAMGWFRQAPGKEREFVAAISRSGDSIDYADSVKGRFTISRDSAKNMVYLQMNSLKPEDTALYHCAARTVSAPPSAAWGYGYWGQGTQVTVSS |
| NbhmMM Rm22.84 | 23 | QVQLQESGGGLVQPGGSLRLSCAASGRTFSNYVNYAMGWFRQPPGKEREFVASISWSSVTTYYADSVKGRFTISRDNAKNTVYLQMNSLKPEDTAVYYCAAHLAQYSDYAYRDPHQFGAWGQGTQVTVSS |
| NbhmMM Rm19.52 | 24 | QVQLQESGGGLVQAGGSLRLSCLASGDTFSNYVMAWFRQAPGKEREIVAAIRLSGARYVPDSVKGRFTISRDNAKNAMYLQMTSLKPEDTARYYCAAGHTWGQYAYWGQGTQVTVSS |
| NbhmMM Rm21.22 | 25 | QVQLQESGGGLVQAGGSLRLSCAASGRTFSSAAMGWFRQAPGKHREPVALINLDDGETYYADIAKGRFTLSKDNAKNSVYLQMNSLKPEDTAVYYCAVRGRFDDNYEYWGQGTQVTVSS |
| NbhmMM Rm14.93 | 26 | QVQLQESGGGLVQAGDSLRLSCAASGRTFSINYMGWYRQAPGKQRELVAAITSGSGSTNYADSVKGRFTISRDNAKKTMYLQMNSLKPEDTAVYYCNADMDSSLSGGYVDVWGQGTQVTVSS |
| NbhmMM Rm15.49 | 27 | QVQLQESGGGLVQAGGSLRLSCAASGSTFSINNMGWYRQAPGKQRELVAGITGGNTHYADSVKGRFTISRDNAKNTMYLQMNSLKPEDTAVYYCNANWGAYWGQGTQVTVSS |
| NbhmMM Rm17.72 | 28 | QVQLQESGGGLVQPGGSLRLSCAASGSIVSINAMGWYRQAPGKQRELVALVTGSGRTNLADSVKGRFTISRDNAKNTVYLQMNSLKPEDTAVYYCNVLVIGPLEGYDYWGQGTQVTVSS |
| NbhmMM Rm10.79 | 29 | QVQLQESGGGLVQPGGSLKLSCAASGSIFSIKTMGWYRQAPGKQRELVAAVSSGGSTNYADSVKGRFTISRDNAKNAVYLQMNSLKPEDTAVYYCNADGVVAWDQPYDNYWGQGTQVTVSS |
| NbhmMM Rm7.67 | 30 | QVQLQESGGGLVQAGGSLRLSCVDQGRTFSVNAMAWYRQAPGKQRELVASITSSGLDTQYAEGMKGRFTISKGNDKFSTYLQMNNLKPDDTAVYYCNAERWDNGMVYWGKGTQVTVSS |
| NbhmMM Rm8.67 | 31 | QVQLQESGGGLVQAGDSLRLSCLATGSMFSINAWGWYRQAPGKQRELVASITSGGGSTEYAESVKGRFTISRDSAKNMLYLQMNSLRPEDTAVYYCNAERWDGYALGYSPNHGSGHRPYNYWGQGTQVTVSS |
| NbhmMM Rm13.89 | 32 | QVQLQESGGGLVQPGGSLRLSCAASGSIFSINAWGWYRQAPGKQRELVAEITSSGGSTNYADSVKGRFTISGDNAKNSVYLHMNNLEPEDTAVYYCKAVAVTFTTPRSDYWGRGTQVTVSS |
| NbhmMM Rm18.63 | 33 | QVQLQESGGGLVQPGGSLRLSCAPSGSIISINAMAWYRQAPGKERELVAAISSGGSTYYADSVKGRFTISGDIAKNLLWLQMNSLKPEDTAMYYCAPGGGWRPGAWGQGTQVTVSS |
| NbhmMM Rm25.86 | 34 | QVQLQESGGGLVQPGGSLRLSCAGSGFTVSTSMINWARQVPGKELEWLVDVLPSGSTYYADPVKGRFTISRDNAQNTIYLQMNYLKPEDTAIYYCAINRETMPPFRGQGTQVTVSS |
| NbhmMM Rm26.70 | 35 | QVQLQESGGGLVQPGGSLRLSCTASGFPFSSAPMSWVRQAPGKELEWVSYIGYTGTIITDYANSVKGRFTISRDNAKNRLYLQMNSLKPEDTAVYFCAQGYARIADSDLVRGQGTQVTVSS |
| NbhmMM Rm27.95 | 36 | QVQLQESGGRLGAAGGSLRLSCTASGFPFNIYPMSWVRQAPGKGFEWVSYISHGGTTTDYSDAVKGRFTISRDNAKNRLYLQMDSLKPEDTAVYFCAQGYARLMTDSELVRGQGTQVTVSS |

TABLE 3

Production yields and physico-chemical characteristics of the anti-human MMR and anti-human/mouse MMR cross-reactive Nbs. All Nbs produce between 0.7 and 9 mg/l *E. coli* culture. T.B.D.: to be determined. The number of amino acids (A.A.) and molecular weight (MW) indicated in the table include the HA and 6xHis tag.

| Name | number of A.A. | MW (dalton) | Theoretical pi | Extinction coefficient (assuming all Cys form cystines) | Estimated production capacity (g/l *E. Coli*) |
|---|---|---|---|---|---|
| anti-human MMR Nbs | | | | | |
| NbhMMRm1.33 | 152 | 16545 | 6.30 | 30620 | 0.7 |
| NbhMMRm10.19 | 140 | 15188 | 6.63 | 31525 | 3.7 |
| NbhMMRm23.30 | 144 | 16150 | 5.71 | 63035 | 2.3 |
| NbhMMRm2.15 | 146 | 16095 | 5.58 | 29130 | 1.6 |
| NbhMMRm3.1 | 137 | 14961 | 6.63 | 30620 | 1.1 |
| NbhMMRm5.38 | 150 | 16535 | 5.51 | 36120 | 1.2 |
| NbhMMRm12.6 | 138 | 15011 | 6.13 | 23045 | 1.7 |

TABLE 3-continued

Production yields and physico-chemical characteristics of the anti-human MMR and anti-human/mouse MMR cross-reactive Nbs. All Nbs produce between 0.7 and 9 mg/l E. coli culture. T.B.D.: to be determined. The number of amino acids (A.A.) and molecular weight (MW) indicated in the table include the HA and 6xHis tag.

| Name | number of A.A. | MW (dalton) | Theoretical pi | Extinction coefficient (assuming all Cys form cystines) | Estimated production capacity (g/l E. Coli) |
|---|---|---|---|---|---|
| NbhMMRm11.5 | 139 | 15106 | 7.17 | 26025 | 6.8 |
| NbhMMRm15.43 | 131 | 14266 | 8.00 | 30035 | 6.2 |
| NbhMMRm16.95 | 140 | 15025 | 7.17 | 26025 | 5.6 |
| NbhMMRm4.83 | 149 | 16395 | 6.70 | 36120 | 3.0 |
| anti-human/anti-mouse MMR Nbs | | | | | |
| NbhmMMRm14.4 | 141 | 15275 | 6.29 | 26025 | 1.6 |
| NbhmMMRm6.71 | 144 | 15295 | 5.70 | 24660 | 2.4 |
| NbhmMMRm24.31 | 144 | 15793 | 8.00 | 26025 | 1.0 |
| NbhmMMRm20.52 | 143 | 15431 | 8.00 | 30035 | 5.4 |
| NbhmMMRm3.49 | 137 | 14875 | 6.63 | 29130 | 1.6 |
| NbhmMMRm22.84 | 149 | 16628 | 7.25 | 35995 | 4.2 |
| NbhmMMRm19.52 | 136 | 14986 | 8.59 | 31525 | 4.1 |
| NbhmMMRm21.22 | 137 | 15045 | 5.91 | 26025 | 2.1 |
| NbhmMMRm14.93 | 141 | 15289 | 6.63 | 26025 | 2.6 |
| NbhmMMRm15.49 | 131 | 14226 | 8.00 | 30035 | 4.0 |
| NbhmMMRm17.72 | 138 | 14896 | 7.18 | 24535 | 3.4 |
| NbhmMMRm10.79 | 140 | 15130 | 6.63 | 31525 | T.B.D |
| NbhmMMRm7.67 | 137 | 15153 | 7.18 | 30035 | 4.0 |
| NbhmMMRm8.67 | 151 | 16635 | 6.76 | 40005 | 2.0 |
| NbhmMMRm13.89 | 139 | 15096 | 6.70 | 30035 | 5.4 |
| NbhmMMRm18.63 | 135 | 14393 | 7.18 | 34045 | 9.0 |
| NbhmMMRm25.86 | 135 | 14891 | 6.29 | 24535 | 3.9 |
| NbhmMMRm26.70 | 140 | 15299 | 7.18 | 24535 | 6.0 |
| NbhmMMRm27.95 | 140 | 15392 | 7.22 | 24535 | 1.0 |

TABLE 4

SPR kinetic and equilibrium parameters for anti-MMR sdAbs on mouse MMR. Nb: Nanobody; SE: standard error; NB: no binding.

| Sample | $k_a$ (1/Ms) | $k_d$ (1/s) | $K_D$ | Chi$^2$ |
|---|---|---|---|---|
| NbMMRm1.33 | NB | NB | NB | |
| NbhMMRm2.15 | NB | NB | NB | |
| NbhMMRm5.38 | 1.3E+5 | 3.3E−3 | 2.5E−8 | 0.216 |
| NbhMMRm10.19 | 8.4E+5 | 2.1E−1 | 2.5E−7 | 0.280 |
| NbhMMRm11.5 | 1.5E+5 | 1.9E−2 | 1.2E−7 | 0.211 |
| NbhMMRm12.6 | NB | NB | NB | |
| NbhMMRm15.43 | 2.9E+4 | 1.3E−3 | 4.4E−8 | 0.299 |
| NbhMMRm16.95 | NB | NB | NB | |
| NbhMMRm23.30 | NB | NB | NB | |
| NbhmMMRm3.1 | 2.1E+5 | 4.0E−3 | 1.9E−8 | 0.459 |
| NbhmMMRm3.49 | 2.9E+5 | 3.6E−3 | 1.2E−8 | 0.451 |
| NbhmMMRm6.71 | NB | NB | NB | |
| NbhmMMRm7.67 | NB | NB | NB | |
| NbhmMMRm10.79 | 1.1E+5 | 4.2E−3 | 3.9E−8 | 0.441 |
| NbhmMMRm14.4 | 3.3E+4 | 2.3E−3 | 6.8E−8 | 0.0343 |
| NbhmMMRm14.93 | 2.9E+4 | 2.1E−3 | 7.4E−8 | 0.0389 |
| NbhmMMRm15.49 | 2.9E+4 | 1.3E−3 | 4.4E−8 | 0.258 |
| NbhmMMRm17.72 | NB | NB | NB | |
| NbhmMMRm19.52 | 3.7E+3 | 3.2E−3 | 8.5E−6 | 0.204 |
| NbhmMMRm20.52 | 1.6E+6 | 2.0E−3 | 1.3E−9 | 1.10 |
| NbhmMMRm21.22 | NB | NB | NB | |
| NbhmMMRm22.84 | 3.0E+4 | 4.0E−3 | 1.3E−7 | 0.0634 |
| NbhmMMRm24.31 | 2.8E+4 | 2.1E−3 | 7.4E−8 | 0.0389 |
| NbhmMMRm26.70 | 6.9E+5 | 1.3E−3 | 1.9E−9 | 0.653 |

TABLE 5

SPR kinetic and equilibrium parameters for anti-MMR sdAbs on human MMR. Nb: Nanobody; SE: standard error; NB: no binding.

| Sample | $k_a$ (1/Ms) | $k_d$ (1/s) | $K_D$ | Chi$^2$ |
|---|---|---|---|---|
| NbMMRm1.33 | 2.0E+5 | 1.5E−3 | 7.7E−9 | 0.394 |
| NbhMMRm2.15 | 1.5E+5 | 1.3E−3 | 8.6E−9 | 0.209 |
| NbhMMRm5.38 | 2.0E+5 | 6.6E−4 | 3.3E−9 | 0.144 |
| NbhMMRm10.19 | 7.5E+5 | 3.1E−2 | 5.0E−8 | 0.240 |
| NbhMMRm11.5 | 4.0E+5 | 2.2E−2 | 5.5E−8 | 0.246 |
| NbhMMRm12.6 | 1.5E+5 | 1.2E−3 | 8.2E−9 | 0.132 |
| NbhMMRm15.43 | 2.2E+4 | 5.9E−3 | 2.7E−7 | 0.201 |
| NbhMMRm16.95 | 6.6E+4 | 1.4E−3 | 2.1E−8 | 0.496 |
| NbhMMRm23.30 | NB | NB | NB | |
| NbhmMMRm3.1 | 2.2E+5 | 7.4E−4 | 3.4E−9 | 0.157 |
| NbhmMMRm3.49 | 4.4E+5 | 8.0E−4 | 1.8E−9 | 0.271 |
| NbhmMMRm6.71 | 1.9E+5 | 1.1E−3 | 5.6E−9 | 0.185 |
| NbhmMMRm7.67 | NB | NB | NB | |
| NbhmMMRm10.79 | 1.6E+4 | 6.6E−3 | 4.2E−7 | 0.122 |
| NbhmMMRm14.4 | 1.4E+5 | 1.4E−3 | 1.0E−8 | 0.136 |
| NbhmMMRm14.93 | 9.5E+4 | 1.2E−3 | 1.3E−8 | 0.135 |
| NbhmMMRm15.49 | 2.1E+4 | 6.1E−3 | 2.9E−7 | 0.196 |
| NbhmMMRm17.72 | 6.2E+4 | 1.2E−3 | 1.9E−8 | 0.442 |
| NbhmMMRm19.52 | 6.0E+3 | 1.0E−2 | 1.7E−6 | 0.107 |
| NbhmMMRm20.52 | 5.1E+5 | 1.3E−1 | 2.6E−7 | 0.392 |
| NbhmMMRm21.22 | 3.4E+5 | 1.2E−3 | 3.6E−9 | 1.72 |
| NbhmMMRm22.84 | 4.9E+4 | 1.9E−3 | 3.8E−8 | 0.262 |
| NbhmMMRm24.31 | 2.6E+5 | 6.9E−4 | 2.7E−9 | 0.386 |
| NbhmMMRm26.70 | 5.8E+5 | 7.3E−3 | 1.3E−8 | 1.03 |

TABLE 6

CDRs of MMR-specific sdAbs

| Nanobody reference number | SEQ ID NO [1] | FR1 | CDR1 | FR2 | CDR2 | FR3 | CDR3 | FR4 |
|---|---|---|---|---|---|---|---|---|
| NbhmMMRm3.49 | 7 | QVQLQESGGGLVQPGGSLRLSCAAS (SEQ ID NO: 37) | GFSLDYYAIG (SEQ ID NO: 67) | WFRQAPGKEREGIS (SEQ ID NO: 97) | CISYKGGST (SEQ ID NO: 127) | TYADSVKGRFTISKDNAKNTAYLQMNSLKPEDTGIYSCAA (SEQ ID NO: 157) | GFVCYNYDY (SEQ ID NO: 187) | WGQGTQVTVSS (SEQ ID NO: 217) |
| NbhMMRm3.1 | 8 | QVQLQESGGGLVQPGGSLRLSCAAS (SEQ ID NO: 38) | GFTLDYYAIG (SEQ ID NO: 68) | WFRQAPGKEREGIS (SEQ ID NO: 98) | CISYKGGST (SEQ ID NO: 128) | TYADSVKGRFTISKDNAKNTAYLQMNNLKPEDTGIYYCAA (SEQ ID NO: 158) | GFVCYNYDY (SEQ ID NO: 188) | WGPGTQVTVSS (SEQ ID NO: 218) |
| NbhmMMRm14.4 | 9 | QVQLQESGGGLVQAGDSLRLSCAAS (SEQ ID NO: 39) | GRTFSINYMG (SEQ ID NO: 69) | WYRQAPGKQRELVA (SEQ ID NO: 99) | AITSGSGST (SEQ ID NO: 129) | NYADSVKGRFTISRDNAKNTMYLQMNSLKPEDTAVYYCNA (SEQ ID NO: 159) | DMDSSLSGGYVDV (SEQ ID NO: 189) | WGQGTQVTVSS (SEQ ID NO: 219) |
| NbhMMRm5.38 | 10 | QVQLQESGGGLVQAGGSLRLSCAAS (SEQ ID NO: 40) | GFTDDDYDIG (SEQ ID NO: 70) | WFRQAPGKEREGVS (SEQ ID NO: 100) | CISSDGST (SEQ ID NO: 130) | YYADSVKGRFTISSDNAKNTVYLQMNSLKPEDTAVYYCAA (SEQ ID NO: 160) | DFFRWDSGSYYVRGCRHATYDY (SEQ ID NO: 190) | WGQGTQVTVSS (SEQ ID NO: 220) |
| NbhMMRm1.33 | 11 | QVQLQESGGGLVQPGGSLRLSCAAS (SEQ ID NO: 41) | GFTLDNYTVA (SEQ ID NO: 71) | WFRQAPGKEREGVS (SEQ ID NO: 101) | CISSSGGST (SEQ ID NO: 131) | NYADSVKGRFTISRDNSKKSVYLQMNSLKPEDTAIYTCAA (SEQ ID NO: 161) | ERAPPYYSGYYFFDSTCVAASYDY (SEQ ID NO: 191) | WGQGTQVTVSS (SEQ ID NO: 221) |
| NbhMMRm10.19 | 12 | QVQLQESGGGLVQPGGSKLSCAAS (SEQ ID NO: 42) | GSIFSIKTMG (SEQ ID NO: 72) | WYRQAPGKQRELVA (SEQ ID NO: 102) | AITSGGST (SEQ ID NO: 132) | NYADSVKGRFTISRDNAKNTVYLQMNSLKPEDTAVYYCNA (SEQ ID NO: 162) | DGVVAWDQPYDNY (SEQ ID NO: 192) | WGQGTQVTVSS (SEQ ID NO: 222) |
| NbhMMRm23.30 | 13 | QVQLQESGGGLVQAGDSLSISCAAS (SEQ ID NO: 43) | GDTFNHYSWG (SEQ ID NO: 73) | WFRQAPGKAREFVA (SEQ ID NO: 103) | AISWNGGS (SEQ ID NO: 133) | KYADSVKGRFAISRDIAKNTVSLQMNSLEPEDTAVYYCAA (SEQ ID NO: 163) | DRRPYNDWWDDWSWWVY (SEQ ID NO: 193) | WGQGTQVTVSS (SEQ ID NO: 223) |
| NbhMMRm2.15 | 14 | QVQLQESGGGLV | GFTLDYYDIG | WFRQAPGKEREG | CISSIGGSA (SEQ | NYADSVKGRFTIS | EAQTPYNDGDCT | WGQGIQVTVSS |

TABLE 6-continued

CDRs of MMR-specific sdAbs

| Nanobody reference number | SEQ ID NO [1] | FR1 | CDR1 | FR2 | CDR2 | FR3 | CDR3 | FR4 |
|---|---|---|---|---|---|---|---|---|
| | | QPGESL RLSCKL S (SEQ ID NO: 44) | (SEQ ID NO: 74) | VS (SEQ ID NO: 104) | ID NO: 134) | RDNVKN TVYLQM NSLKPE DTAIYY CAA (SEQ ID NO: 164) | RASYDY (SEQ ID NO: 194) | (SEQ ID NO: 224) |
| NbhMM Rm12.6 | 15 | QVQLQE SGGGLV QPGGSL RLSCVV S (SEQ ID NO: 45) | GSFLSIN HMG (SEQ ID NO: 75) | WYRQV SGEQRE LVA (SEQ ID NO: 105) | AITSGGS T (SEQ ID NO: 135) | NYADSV KGRFTIS RDSAKN TVYLQM NSLKPE DTAVYY CNA (SEQ ID NO: 165) | DALTML PPFDF (SEQ ID NO: 195) | WGQGT QVTVSS (SEQ ID NO: 225) |
| NbhMM Rm11.5 | 16 | QVQLQE SGGGLV QPGGSL MLSCAA S (SEQ ID NO: 46) | GNIFTIN RMG (SEQ ID NO: 76) | WYRQA PGKQRE LVA (SEQ ID NO: 106) | AITSGG NT (SEQ ID NO: 136) | NYADSV KGRFTIS RDNAKN TVYLQM NSLKPE DTAVYY CNA (SEQ ID NO: 166) | AIVTMT SPYSDY (SEQ ID NO: 196) | WGQGT QVTVSS (SEQ ID NO: 226) |
| NbhMM Rm15.43 | 17 | QVQLQE SGGTLV QPGGSL RLSCAA S (SEQ ID NO: 47) | GSTFSIN NMG (SEQ ID NO: 77) | WYRQA PGKQRE LVA (SEQ ID NO: 107) | GITGGN T (SEQ ID NO: 137) | HYADSV KGRFTIS RDNAKN TMYLQ MNGLKP EDTAVY YCNA (SEQ ID NO: 167) | NWGAY (SEQ ID NO: 197) | WGQGT QVTVSS (SEQ ID NO: 227) |
| NbhMM Rm16.95 | 18 | QVQLQE SGGGLV QPGGSL GLSCAA S (SEQ ID NO: 48) | GRIASIS AMG (SEQ ID NO: 78) | WYRQA PGKQRE LVA (SEQ ID NO: 108) | AITGSG RT (SEQ ID NO: 138) | NYADSV KGRFTIS RDNAKN TVYLQM NSLKPE DTAVYY CNL (SEQ ID NO: 168) | LMVDY GLGLGT DY (SEQ ID NO: 198) | WGQGT QVTVSS (SEQ ID NO: 228) |
| NbhMM Rm4.83 | 19 | QVQLQE SGGGLV QPGGSL RLSCAA SG (SEQ ID NO: 49) | PGFKLD YYAIA (SEQ ID NO: 79) | WFRQAP GKEREG VS (SEQ ID NO: 109) | CIGGSGS GLT (SEQ ID NO: 139) | TYVENS VKDRFT ISRDNA QNTVYL HMNSLK PEDTGIY YCAA (SEQ ID NO: 169) | DTYYYC SKRVWR NDYGS (SEQ ID NO: 199) | WGQGT QVTVSS (SEQ ID NO: 229) |
| NbhmMM Rm6.71 | 20 | QVQLQE SGGGLV QAGGSL RLSCAA S (SEQ ID NO: 50) | GGTFDD SVIG (SEQ ID NO: 80) | WFRQAP GKEREG VS (SEQ ID NO: 110) | CISSNDG TT (SEQ ID NO: 140) | HYASPV KGRFTIS SDNAKN TVYLQM NSLKPE DTAVYY CAA (SEQ ID NO: 170) | ETPSIGS PCTSAS YDY (SEQ ID NO: 200) | WGQGT QVTVSS (SEQ ID NO: 230) |
| NbhmMM Rm24.31 | 21 | QVQLQE SGGGLV | GFTLKN HHIG | WLRQAP GKEREG | SINSSGG ST (SEQ | NYADSV QGRFTIS | LRRYYG LNLDPG | WGQGT QVTVSS |

TABLE 6-continued

CDRs of MMR-specific sdAbs

| Nanobody reference number | SEQ ID NO[1] | FR1 | CDR1 | FR2 | CDR2 | FR3 | CDR3 | FR4 |
|---|---|---|---|---|---|---|---|---|
| | | QPGGSL RLSCTA T (SEQ ID NO: 51) | (SEQ ID NO: 81) | VA (SEQ ID NO: 111) | ID NO: 141) | RDNAKN TVFLQM NSLKSE DTAVYY CAR (SEQ ID NO: 171) | SYDY (SEQ ID NO: 201) | (SEQ ID NO: 231) |
| NbhmMM Rm20.52 | 22 | QVQLQE SGGGLV QAGGSL RLSCAA S (SEQ ID NO: 52) | GRIFSAY AMG (SEQ ID NO: 82) | WFRQAP GKEREF VA (SEQ ID NO: 112) | AISRSGD ST (SEQ ID NO: 142) | DYADSV KGRFTIS RDSAKN MVYLQ MNSLKP EDTALY HCAA (SEQ ID NO: 172) | RTVSAP PSAAWG YGY (SEQ ID NO: 202) | WGQGT QVTVSS (SEQ ID NO: 232) |
| NbhmMM Rm22.84 | 23 | QVQLQE SGGGLV QPGGSL RLSCAA S (SEQ ID NO: 53) | GRTFSN YVNYA MG (SEQ ID NO: 83) | WFRQFP GKEREF VA (SEQ ID NO: 113) | SISWSSV TT (SEQ ID NO: 143) | YYADSV KGRFTIS RDNAKN TVYLQM NSLKPE DTAVYY CAA (SEQ ID NO: 173) | HLAQYS DYAYRD PHQFGA (SEQ ID NO: 203) | WGQGT QVTVSS (SEQ ID NO: 233) |
| NbhmMM Rm19.52 | 24 | QVQLQE SGGGLV QAGGSL RLSCLA S (SEQ ID NO: 54) | GDTFSN YVMA (SEQ ID NO: 84) | WFRQAP GKEREI VA (SEQ ID NO: 114) | AIRLSG AR (SEQ ID NO: 144) | YVPDSV KGRFTIS RDNAKN AMYLQ MTSLKP EDTARY CAA (SEQ ID NO: 174) | GHTWG QYAY (SEQ ID NO: 204) | WGQGT QVTVSS (SEQ ID NO: 234) |
| NbhmMM Rm21.22 | 25 | QVQLQE SGGGLV QAGGSL RLSCAA S (SEQ ID NO: 55) | GRTFSS AAMG (SEQ ID NO: 85) | WFRQAP GKEREP VA (SEQ ID NO: 115) | LINLDD GET (SEQ ID NO: 145) | YYADIA KGRFTL SKDNAK NSVYLQ MNSLKP EDTAVY YCAV (SEQ ID NO: 175) | RGRFDD NYEY (SEQ ID NO: 205) | WGQGT QVTVSS (SEQ ID NO: 235) |
| NbhmMM Rm14.93 | 26 | QVQLQE SGGGLV QAGDSL RLSCAA S (SEQ ID NO: 56) | GRTFSIN YMG (SEQ ID NO: 86) | WYRQA PGKQRE LVA (SEQ ID NO: 116) | AITSGSG ST (SEQ ID NO: 146) | NYADSV KGRFTIS RDNAKK TMYLQ MNSLKP EDTAVY YCNA (SEQ ID NO: 176) | DMDSSL SGGYVD V (SEQ ID NO: 206) | WGQGT QVTVSS (SEQ ID NO: 236) |
| NbhmMM Rm15.49 | 27 | QVQLQE SGGGLV QAGGSL RLSCAA S (SEQ ID NO: 57) | GSTFSIN NMG (SEQ ID NO: 87) | WYRQA PGKQRE LVA (SEQ ID NO: 117) | GITGGN T (SEQ ID NO: 147) | HYADSV KGRFTIS RDNAKN TMYLQ MNSLKP EDTAVY YCNA (SEQ ID NO: 177) | NWGAY (SEQ ID NO: 207) | WGQGT QVTVSS (SEQ ID NO: 237) |
| NbhmMM Rm17.72 | 28 | QVQLQE SGGGLV | GSIVSIN AMG | WYRQA PGKQRE | LVTGSG RT (SEQ | NLADSV KGRFTIS | LVIGPLE GYDY | WGQGT QVTVSS |

TABLE 6-continued

CDRs of MMR-specific sdAbs

| Nanobody reference number | SEQ ID NO [1] | FR1 | CDR1 | FR2 | CDR2 | FR3 | CDR3 | FR4 |
|---|---|---|---|---|---|---|---|---|
| | | QPGGSL RLSCAA S (SEQ ID NO: 58) | (SEQ ID NO: 88) | LVA (SEQ ID NO: 118) | ID NO: 148) | RDNAKN TVYLQM NSLKPE DTAVYY CNV (SEQ ID NO: 178) | (SEQ ID NO: 208) | (SEQ ID NO: 238) |
| NbhmMM Rm10.79 | 29 | QVQLQE SGGGLV QPGGSL KLSCAA S (SEQ ID NO: 59) | GSIFSIK TMG (SEQ ID NO: 89) | WYRQA PGKQRE LVA (SEQ ID NO: 119) | AVSSGG ST (SEQ ID NO: 149) | NYADSV KGRFTIS RDNAKN AVYLQ MNSLKP EDTAVY YCNA (SEQ ID NO: 179) | DGVVA WDQPY DNY (SEQ ID NO: 209) | WGQGT QVTVSS (SEQ ID NO: 239) |
| NbhmMM Rm7.67 | 30 | QVQLQE SGGGLV QAGGSL RLSCVD Q (SEQ ID NO: 60) | GRTFSV NAMA (SEQ ID NO: 90) | WYRQA PGKQRE LVA (SEQ ID NO: 120) | SITSSGL DT (SEQ ID NO: 150) | QYAEG MKGRFT ISKGND KFSTYL QMNNL KPDDTA VYYCNA (SEQ ID NO: 180) | ERWDN GMVY (SEQ ID NO: 210) | WGKGT QVTVSS (SEQ ID NO: 240) |
| NbhmMM Rm8.67 | 31 | QVQLQE SGGGLV QAGDSL RLSCLA T (SEQ ID NO: 61) | GSMFSI NAWG (SEQ ID NO: 91) | WYRQA PGKQRE LVA (SEQ ID NO: 121) | SITSGGG ST (SEQ ID NO: 151) | EYAESV KGRFTIS RDSAKN MLYLQ MNSLRP EDTAVY YCNA (SEQ ID NO: 181) | ERWDG YALGYS PNHGSG HRPYNY (SEQ ID NO: 211) | WGQGT QVTVSS (SEQ ID NO: 241) |
| NbhmMM Rm13.89 | 32 | QVQLQE SGGGLV QPGGSL RLSCAA S (SEQ ID NO: 62) | GSIFSIN AWG (SEQ ID NO: 92) | WYRQA PGKQRE LVA (SEQ ID NO: 122) | EITSSGS T (SEQ ID NO: 152) | NYADSV KGRFTIS GDNAK NSVYLH MNNLEP EDTAVY YCKA (SEQ ID NO: 182) | VAVTFT TPRSDY (SEQ ID NO: 212) | WGRGT QVTVSS (SEQ ID NO: 242) |
| NbhmMM Rm18.63 | 33 | QVQLQE SGGGLV QPGGSL RLSCAP S (SEQ ID NO: 63) | GSIISINA MA (SEQ ID NO: 93) | WYRQA PGKERE LVA (SEQ ID NO: 123) | AISSGGS T (SEQ ID NO: 153) | YYADSV KGRFTIS GDIAKN LLWLQ MNSLKP EDTAMY YCAP (SEQ ID NO: 183) | GGGWR PGA (SEQ ID NO: 213) | WGQGT QVTVSS (SEQ ID NO: 243) |
| NbhmMM Rm25.86 | 34 | QVQLQE SGGGLV QPGGSL RLSCAG S (SEQ ID NO: 64) | GFTVST SMIN (SEQ ID NO: 94) | WARQV PGKELE WLV (SEQ ID NO: 124) | DVLPSG ST (SEQ ID NO: 154) | YYADPV KGRFTIS RDNAQN TIYLQM NYLKPE DTAIYY CAI (SEQ ID NO: 184) | NRETMP PF (SEQ ID NO: 214) | RGQGTQ VTVSS (SEQ ID NO: 244) |
| NbhmMM Rm26.70 | 35 | QVQLQE SGGGLV | GFPFSSA PMS | WVRQA PGKELE | YIGYTG TIT (SEQ | DYANSV KGRFTIS | GYARLI ADSDLV | RGQGTQ VTVSS |

TABLE 6-continued

CDRs of MMR-specific sdAbs

| Nanobody reference number | SEQ ID NO [1] | FR1 | CDR1 | FR2 | CDR2 | FR3 | CDR3 | FR4 |
|---|---|---|---|---|---|---|---|---|
| | | QPGGSL RLSCTA S (SEQ ID NO: 65) | (SEQ ID NO: 95) | WVS (SEQ ID NO: 125) | ID NO: 155) | RDNAKN RLYLQM NSLKPE DTAVYF CAQ (SEQ ID NO: 185) | (SEQ ID NO: 215) | (SEQ ID NO: 245) |
| NbhmMM Rm27.95 | 36 | QVQLQE SGGRLG AAGGSL RLSCTA S (SEQ ID NO: 66) | GFPFNIY PMS (SEQ ID NO: 96) | WVRQA PGKGFE WVS (SEQ ID NO: 126) | YISHGG TTT (SEQ ID NO: 156) | DYSDAV KGRFTIS RDNAKN RLYLQM DSLKPE DTAVYF CAQ (SEQ ID NO: 186) | GYARL MTDSEL V (SEQ ID NO: 216) | RGQGTQ VTVSS (SEQ ID NO: 246) |

[1] Nanobody sequences without His tag

TABLE 7

Amino acid sequences of human and mouse macrophage mannose receptor

| Name | SEQ ID NO | Amino acid sequence |
|---|---|---|
| Human MMR (MRC1) | 1 | MRLPLLLVFASVIPGAVLLLDTRQFLIYNEDHKRC VDAVSPSAVQTAACNQDAESQKFRWVSESQIMSVA FKLCLGVPSKTDWVAITLYACDSKSEFQKWECKND TLLGIKGEDLFFNYGNRQEKNIMLYKGSGLWSRWK IYGTTDNLCSRGYEAMYTLLGNANGATCAFPPKFE NKWYADCTSAGRSDGWLWCGTTTDYDTDKLFGYCP LKFEGSESLWNKDPLTSVSYQINSKSALTWHQARK SCQQQNAELLSITEIHEQTYLTGLTSSLTSGLWIG LNSLSFNSGWQWSDRSPFRYLNWLPGSPSAEPGKS CVSLNPGKNAKWENLECVQKLGYICKKGNTTLNSF VIPSESDVPTHCPSQWWPYAGHCYKIHRDEKKIQR DALTTCRKEGGDLTSIHTIEELDFIISQLGYEPND ELWIGLNDIKIQMYFEWSDGTPVTFTKWLRGEPSH ENNRQEDCVVMKGKDGYWADRGCEWPLGYICKMKS RSQGPEIVEVEKGCRKGWKKHHFYCYMIGHTLSTF AEANQTCNNENAYLTTIEDRYEQAFLTSFVGLRPE KYFWTGLSDIQTKGTFQWTIEEEVRFTHWNSDMPG RKPGCVAMRTGIAGGLWDVLKCDEKAKFVCKHWAE GVTHPPKPTTTPEPKCPEDWGASSRTSLCFKLYAK GKHEKKTWFESRDFCRALGGDLASINNKEEQQTIW RLITASGSYHRLFWLGLTYGSPSEGFTWSDGSPVS YENWAYGEPNNYQNVEYCGELKGDPTMSWNDINCE HLNNWICQIQKGQTPKPEPTPAPQDNPPVTEDGWV IYKDYQYYFSKEKETMDNARAFCKRNFGDLVSIQS ESEKKFLWKYVNRNDAQSAYFIGLLISLDKKFAWM DGSKVDYVSWATGEPNFANEDENCVTMYSNSGFWN DINCGYPNAFICQRHNSSINATTVMPTMPSVPSGC KEGWNFYSNKCFKIFGFMEEERKNWQEARKACIGF GGNLVSIQNEKEQAFLTYHMKDSTFSAWTGLNDVN SEHTFLWTDGRGVHYTNWGKGYPGGRRSSLSYEDA DCVVIIGGASNEAGKWMDDTCDSKRGYICQTRSDP SLTNPPATIQTDGFVKYGKSSYSLMRQKFQWHEAE TYCKLHNSLIASILDPYSNAFAWLQMETSNERVWI ALNSNLTDNQYTWTDKWRVRYTNWAADEPKLKSAC VYLDLDGYWKTAHCNESFYFLCKRSDEIPATEPPQ LPGRCPESDHTAWIPFHGHCYYIESSYTRNWGQAS LECLRMGSSLVSIESAAESSFLSYRVEPLKSKTNF WIGLFRNVEGTWLWINNSPVSFVNWNTGDPSGERN DCVALHASSGFWSNIHCSSYKGYICKRPKIIDAKP THELLTTKADTRKMDPSKPSSNVAGVVIIVILLIL TGAGLAAYFFYKKRRVHLPQEGAFENTLYFNSQSS PGTSDMKDLVGNIEQNEHSVI |
| Recombinant human MMR (R&D systems) | 2 | LLDTRQFLIYNEDHKRCVDAVSPSAVQTAACNQDA ESQKFRWVSESQIMSVAFKLCLGVPSKTDWVAITL YACDSKSEFQKWECKNDTLLGIKGEDLFFNYGNRQ EKNIMLYKGSGLWSRWKIYGTTDNLCSRGYEAMYT LLGNANGATCAFPPKFENKWYADCTSAGRSDGWLW CGTTTDYDTDKLFGYCPLKFEGSESLWNKDPLTSV SYQINSKSALTWHQARKSCQQQNAELLSITEIHEQ TYLTGLTSSLTSGLWIGLNSLSFNSGWQWSDRSPF RYLNWLPGSPSAEPGKSCVSLNPGKNAKWENLECV QKLGYICKKGNTTLNSFVIPSESDVPTHCPSQWWP YAGHCYKIHRDEKKIQRDALTTCRKEGGDLASIHT IEEFDFIISQLGYEPNDELWIGLNDIKIQMYFEWS DGTPVTFTKWLRGEPSHENNRQEDCVVMKGKDGYW ADRGCEWPLGYICKMKSRSQGPEIVEVEKGCRKGW KKHHFYCYMIGHTLSTFAEANQTCNNENAYLTTIE DRYEQAFLTSFVGLRPEKYFWTGLSDIQTKGTFQW TIEEEVRFTHWNSDMPGRKPGCVAMRTGIAGGLWD VLKCDEKAKFVCKHWAEGVTHPPKPTTTPEPKCPE DWGASSRTSLCFKLYAKGKHEKKTWFESRDFCRAL GGDLASINNKEEQQTIWRLITASGSYHKLFWLGLT YGSPSEGFTWSDGSPVSYENWAYGEPNNYQNVEYC GELKGDPTMSWNDINCEHLNNWICQIQKGQTPKPE PTPAPQDNPPVTEDGWVIYKDYQYYFSKEKETMDN ARAFCKRNFGDLVSIQSESEKKFLWKYVNRNDAQS AYFIGLLISLDKKFAWMDGSKVDYVSWATGEPNFA NEDENCVTMYSNSGFWNDINCGYPNAFICQRHNSS INATTVMPTMPSVPSGCKEGWNFYSNKCFKIFGFM EEERKNWQEARKACIGFGGNLVSIQNEKEQAFLTY HMKDSTFSAWTGLNDVNSEHTFLWTDGRGVHYTNW GKGYPGGRRSSLSYEDADCVVIIGGASNEAGKWMD DTCDSKRGYICQTRSDPSLTNPPATIQTDGFVKYG KSSYSLMRQKFQWHEAETYCKLHNSLIASILDPYS NAFAWLQMETSNERVWIALNSNLTDNQYTWTDKWR VRYTNWAADEPKLKSACVYLDLDGYWKTAHCNESF YFLCKRSDEIPATEPPQLPGRCPESDHTAWIPFHG HCYYIESSYTRNWGQASLECLRMGSSLVSIESAAE SSFLSYRVEPLKSKTNFWIGLFRNVEGTWLWINNS PVSFVNWNTGDPSGERNDCVALHASSGFWSNIHCS SYKGYICKRPKIIDAKPTHELLTTKADTRKMDPSK HHHHHH |

TABLE 7-continued

Amino acid sequences of human and mouse macrophage mannose receptor

| Name | SEQ ID NO | Amino acid sequence |
|---|---|---|
| Mouse MMR (Mrc1) | 3 | MRLLLLLAFISVIPVSVQLLDARQFLIYNEDHKRC VDALSAISVQTATCNPEAESQKFRWVSDSQIMSVA FKLCLGVPSKTDWASVTLYACDSKSEYQKWECKND TLFGIKGTELYFNYGNRQEKNIKLYKGSGLWSRWK VYGTTDDLCSRGYEAMYSLLGNANGAVCAFPPKFE NKWYADCTSAGRSDGWLWCGTTTDYDKDKLFGFCP LHFEGSERLWNKDPLTGILYQINSKSALTWHQARA SCKQQNADLLSVTEIHEQMYLTGLTSSLSSGLWIG LNSLSVRSGWQWAGGSPFRYLNWLPGSPSSEPGKS CVSLNPGKNAKWENLECVQKLGYICKKGNNTLNPF IIPSASDVPTGCPNQWWPYAGHCYRIHREEKKIQK YALQACRKEGGDLASIHSIEEFDFIFSQLGYEPND ELWIGLNDIKIQMYFEWSDGTPVTFTKWLPGEPSH ENNRQEDCVVMKGKDGYWADRACEQPLGYICKMVS QSHAVVPEGADKGCRKGWKRHGFYCYLIGSTLSTF TDANHTCTNEKAYLTTVEDRYEQAFLTSLVGLRPE KYFWTGLSDVQNKGTFRWTVDEQVQFTHWNADMPG RKAGCVAMKTGVAGGLWDVLSCEEKAKFVCKHWAE GVTRPPEPTTTPEPKCPENWGTTSKTSMCFKLYAK GKHEKKTWFESRDFCKAIGGELASIKSKDEQQVIW RLITSSGSYHELFWLGLTYGSPSEGFTWSDGSPVS YENWAYGEPNNYQNVEYCGELKGDPGMSWNDINCE HLNNWICIQKGKTLLPEPTPAPQDNPPVTADGWVI IYKDYQYYFSKEKETMDNARAFCKKNFGDLATIKS ESEKKFLWKYINKNGGQSPYFIGMLISMDKKFIWM DGSKVDFVAWATGEPNFANDDENCVTMYTNSGFWN DINCGYPNNFICQRHNSSINATAMPTTPTTPGGCK EGWHLYKNKCFKIFGFANEEKKSWQDARQACKGLK GNLVSIENAQEQAFVTYHMRDSTFNAWTGLNDINA EHMFLWTAGQGVHYTNWGKGYPGGRRSSLSYEDAD CVVVIGGNSREAGTWMDDTCDSKQGYICQTQTDPS LPVSPTTTPKDGFVTYGKSSYSLMKLKLPWHEAET YCKDHTSLLASILDPYSNAFAWMKMHPFNVPIWIA LNSNLTNNEYTWTDRWRVYTNWGADEPKLKSACV YMDVDGYWRTSYCNESFYFLCKKSDEIPATEPPQL PGKCPESEQTAWIPFYGHCYYFESSFTRSWGQASL ECLRMGASLVSIETAAESSFLSYRVEPLKSKTNFW IGMFRNVEGKWLWLNDNPVSFVNWKTGDPSGERND CVVLASSSGLWNNIHCSSYKGFICKMPKIIDPVTT HSSITTKADQRKMDPQPKGSSKAAGVVTTVVLLIVI GAGVAAYFFYKKRHALHIPQEATFENTLYFNSNLS PGTSDTKDLMGNIEQNEHAII |
| Recombinant mouse MMR (R&D systems) | 4 | LLDARQFLIYNEDHKRCVDALSAISVQTATCNPEA ESQKFRWVSDSQIMSVAFKLCLGVPSKTDWASVTL YACDSKSEYQKWECKNDTLFGIKGTELYFNYGNRQ EKNIKLYKGSGLWSRWKVYGTTDDLCSRGYEAMYS LLGNANGAVCAFPPKFENKWYADCTSAGRSDGWLW CGTTTDYDKDKLFGFCPLHFEGSERLWNKDPLTGI LYQINSKSALTWHQARASCKQQNADLLSVTEIHEQ MYLTGLTSSLSSGLWIGLNSLSVRSGWQWAGGSPF RYLNWLPGSPSSEPGKSCVSLNPGKNAKWENLECV QKLGYICKKGNNTLNPFIIPSASDVPTGCPNQWWP YAGHCYRIHREEKKIQKYALQACRKEGGDLASIHS IEEFDFIFSQLGYEPNDELWIGLNDIKIQMYFEWS DGTPVTFTKWLPGEPSHENNRQEDCVVMKGKDGYW ADRACEQPLGYICKMVSQSHAVVPEGADKGCRKGW KRHGFYCYLIGSTLSTFTDANHTCTNEKAYLTTVE DRYEQAFLTSLVGLRPEKYFWTGLSDVQNKGTFRW TVDEQVQFTHWNADMPGRKAGCVAMKTGVAGGLWD VLSCEEKAKFVCKHWAEGVTRPPEPTTTPEPKCPE NWGTTSKTSMCFKLYAKGKHEKKTWFESRDFCKAI GGELASIKSKDEQQVIWRLITSSGSYHELFWLGLT YGSPSEGFTWSDGSPVSYENWAYGEPNNYQNVEYC GELKGDPGMSWNDINCEHLNNWICIQKGKTLLPE PTPAPQDNPPVTADGWVIYKDYQYYFSKEKETMDN ARAFCKKNFGDLATIKSESEKKFLWKYINKNGGQS PYFIGMLISMDKKFIWMDGSKVDFVAWATGEPNFA NDDENCVTMYTNSGFWNDINCGYPNNFICQRHNSS INATAMPTTPTTPGGCKEGWHLYKNKCFKIFGFAN EEKKSWQDARQACKGLKGNLVSIENAQEQAFVTYH MRDSTFNAWTGLNDINAEHMFLWTAGQGVHYTNWG KGYPGGRRSSLSYEDADCVVVIGGNSREAGTWMDD TCDSKQGYICQTQTDPSLPVSPTTTPKDGFVTYGK SSYSLMKLKLPWHEAETYCKDHTSLLASILDPYSN AFAWMKMHPFNVPIWIALNSNLTNNEYTWTDRWRV RYTNWGADEPKLKSACVYMDVDGYWRTSYCNESFY FLCKKSDEIPATEPPQLPGKCPESEQTAWIPFYGH CYYFESSFTRSWGQASLECLRMGASLVSIETAAES SFLSYRVEPLKSKTNFWIGMFRNVEGKWLWLNDNP VSFVNWKTGDPSGERNDCVVLASSSGLWNNIHCSS YKGFICKMPKIIDPVTTHSSITTKADQRKMDPQPK GSSKAHHHHHH |
| Human MMR (MRC1) - ectodomain | 5 | LLDTRQFLIYNEDHKRCVDAVSPSAVQTAACNQDA ESQKFRWVSESQIMSVAFKLCLGVPSKTDWVAITL YACDSKSEFQKWECKNDTLLGIKGEDLFFNYGNRQ EKNIMLYKGSGLWSRWKIYGTTDNLCSRGYEAMYT LLGNANGATCAFPFKFENKWYADCTSAGRSDGWLW CGTTTDYDTDKLFGYCPLKFEGSESLWNKDPLTSV SYQINSKSALTWHQARKSCQQQNAELLSITEIHEQ TYLTGLTSSLTSGLWIGLNSLSFNSGWQWSDRSPF RYLNWLPGSSPSAEPGKSCVSLNPGKNAKWENLECV QKLGYICKKGNTTLNSFVIPSESDVPTHCPSQWWP YAGHCYKIHRDEKKIQRDALTTCRKEGGDLTSIHT IEELDFIISQLGYEPNDELWIGLNDIKIQMYFEWS DGTPVTFTKWLRGEPSHENNRQEDCVVMKGKDGYW ADRGCEWPLGYICKMKSRSQGPEIVEVEKGCRKGW KKHHFYCYMIGHTLSTFAEANQTCNNENAYLTTIE DRYEQAFLTSFVGLRPEKYFWTGLSDIQTKGTFQW TIEEEVRFTHWNSDMPGRKPGCVAMRTGIAGGLWD VLKCDEKAKFVCKHWAEGVTHPPKPTTTPEPKCPE DWGASSRTSLCFKLYAKGKEIEKKTWFESRDFCRA LGGDLASINNKEEQQTIWRLITASGSYHKLFWLGL TYGSPSEGFTWSDGSPVSYENWAYGEPNNYQNVEY CGELKGDPTMSWNDINCEHLNNWICQIQKGQTPKP EPTPAPQDNPPVTEDGWVIYKDYQYYFSKEKETMD NARAFCKRNFGDLVSIQSESEKKFLWKYVNRNDAQ SAYFIGLLISLDKKFAWMDGSKVDYVSWATGEPNF ANEDENCVTMYSNSGFWNDINCGYPNAFICRHNS SINATTVMPTMPSVPSGCKEGWNFYSNKCFKIFGF MEEERKNWQEARKACIGFGGNLVSIQNEKEQAFLT YHMKDSTFSAWTGLNDVNSEHTFLWTDGRGVHYTN WGKGYPGGRRSSLSYEDADCVVIIGGASNEAGKWM DDTCDSKRGYICQTRSDPSLTNPPATIQTDGFVKY GKSSYSLMRQKFQWHEAETYCKLHNSLIASILDPY SNAFAWLQMETSNERVWIALNSNLTDNQYTWTDKW RVRYTNWAADEPKLKSACVYLDLDGYWKTAHCNES FYFLCKRSDEIPATEPPQLPGRCPESDHTAWIPFH GHCYYIESSYTRNWGQASLECLRMGSSLVSIESAA ESSFLSYRVEPLKSKTNFWIGLFRNVEGTWLWINN SPVSFVNWNTGDPSGERNDCVALHASSGFWSNIHC SSYKGYICKRPKIIDAKPTHELLTTKADTRKMDPS K |
| Mouse MMR (Mrc1) - ectodomain | 6 | LLDARQFLIYNEDHKRCVDALSAISVQTATCNPEA ESQKFRWVSDSQIMSVAFKLCLGVPSKTDWASVTL YACDSKSEYQKWECKNDTLFGIKGTELYFNYGNRQ EKNIKLYKGSGLWSRWKVYGTTDDLCSRGYEAMYS LLGNANGAVCAFPPKFENKWYADCTSAGRSDGWLW CGTTTDYDKDKLFGFCPLHFEGSERLWNKDPLTGI LYQINSKSALTWHQARASCKQQNADLLSVTEIHEQ MYLTGLTSSLSSGLWIGLNSLSVRSGWQWAGGSPF RYLNWLPGSPSSEPGKSCVSLNPGKNAKWENLECV QKLGYICKKGNNTLNPFIIPSASDVPTGCPNQWWP YAGHCYRIHREEKKIQKYALQACRKEGGDLASIHS IEEFDFIFSQLGYEPNDELWIGLNDIKIQMYFEWS DGTPVTFTKWLPGEPSHENNRQEDCVVMKGKDGYW ADRACEQPLGYICKMVSQSHAVVPEGADKGCRKGW KRHGFYCYLIGSTLSTFTDANHTCTNEKAYLTTVE DRYEQAFLTSLVGLRPEKYFWTGLSDVQNKGTFRW TVDEQVQFTHWNADMPGRKAGCVAMKTGVAGGLWD VLSCEEKAKFVCKHWAEGVTRPPEPTTTPEPKCPE NWGTTSKTSMCFKLYAKGKHEKKTWFESRDFCKAI GGELASIKSKDEQQVIWRLITSSGSYHELFWLGLT YGSPSEGFTWSDGSPVSYENWAYGEPNNYQNVEYC GELKGDPGMSWNDINCEHLNNWICIQKGKTLLPE |

TABLE 7-continued

Amino acid sequences of human and mouse macrophage mannose receptor

| Name | SEQ ID NO | Amino acid sequence |
|---|---|---|
| | | PTPAPQDNPPVTADGWVIYKDYQYYFSKEKETMDN ARAFCKKNFGDLATIKSESEKKFLWKYINKNGGQS PYFIGMLISMDKKFIWMDGSKVDFVAWATGEPNFA NDDENCVTMYTNSGFWNDINCGYPNNFICQRHNSS INATAMPTTPTTPPGGCKEGWHLYKNKCFKIFGFAN EEKKSWQDARQACKGLKGNLVSIENAQEQAFVTYH MRDSTFNAWTGLNDINAEHMFLWTAGQGVHYTNWG KGYPGGRRSSLSYEDADCVVVIGGNSREAGTWMDD TCDSKQGYICQTQTDPSLPVSPTTTPKDGFVTYGK SSYSLMKLKLPWHEAETYCKDHTSLLASILDPYSN AFAWMKMHPFNVPIWIALNSNLTNNEYTWTDRWRV RYTNWGADEPKLKSACVYMDVDGYWRTSYCNESFY FLCKKSDEIPATEPPQLPGKCPESEQTAWIPFYGH CYYFESSFTRSWGQASLECLRMGASLVSIETAAES SFLSYRVEPLKSKTNFWIGMFRNVEGKWLWLNDNP VSFVNWKTGDPSGERNDCVVLASSSGLWNNIHCSS YKGFICKMPKIIDPVTTHSSITTKADQRKMDPQPK GSSKA |

The invention claimed is:

1. An immunoglobulin single variable domain that is directed against human macrophage mannose receptor (SEQ ID NO: 1), wherein the immunoglobulin single variable domain comprises a peptide that comprises four framework regions (FRs) and three complementarity-determining regions (CDRs) according to the following formula (1):

FR1-CDR1-FR2-CDR2-FR3-CDR3-FR4     (1);

wherein the peptide is selected from the group consisting of peptides, in which:
CDR1 is SEQ ID NO: 67, CDR2 is SEQ ID NO: 127, and CDR3 is SEQ ID NO: 187;
CDR1 is SEQ ID NO: 68, CDR2 is SEQ ID NO: 128, and CDR3 is SEQ ID NO: 188;
CDR1 is SEQ ID NO: 69, CDR2 is SEQ ID NO: 129, and CDR3 is SEQ ID NO: 189;
CDR1 is SEQ ID NO: 70, CDR2 is SEQ ID NO: 130, and CDR3 is SEQ ID NO: 190;
CDR1 is SEQ ID NO: 71, CDR2 is SEQ ID NO: 131, and CDR3 is SEQ ID NO: 191;
CDR1 is SEQ ID NO: 72, CDR2 is SEQ ID NO: 132, and CDR3 is SEQ ID NO: 192;
CDR1 is SEQ ID NO: 73, CDR2 is SEQ ID NO: 133, and CDR3 is SEQ ID NO: 193;
CDR1 is SEQ ID NO: 74, CDR2 is SEQ ID NO: 134, and CDR3 is SEQ ID NO: 194;
CDR1 is SEQ ID NO: 75, CDR2 is SEQ ID NO: 135, and CDR3 is SEQ ID NO: 195;
CDR1 is SEQ ID NO: 76, CDR2 is SEQ ID NO: 136, and CDR3 is SEQ ID NO: 196;
CDR1 is SEQ ID NO: 77, CDR2 is SEQ ID NO: 137, and CDR3 is SEQ ID NO: 197;
CDR1 is SEQ ID NO: 78, CDR2 is SEQ ID NO: 138, and CDR3 is SEQ ID NO: 198;
CDR1 is SEQ ID NO: 79, CDR2 is SEQ ID NO: 139, and CDR3 is SEQ ID NO: 199;
CDR1 is SEQ ID NO: 80, CDR2 is SEQ ID NO: 140, and CDR3 is SEQ ID NO: 200;
CDR1 is SEQ ID NO: 81, CDR2 is SEQ ID NO: 141, and CDR3 is SEQ ID NO: 201;
CDR1 is SEQ ID NO: 82, CDR2 is SEQ ID NO: 142, and CDR3 is SEQ ID NO: 202;
CDR1 is SEQ ID NO: 83, CDR2 is SEQ ID NO: 143, and CDR3 is SEQ ID NO: 203;
CDR1 is SEQ ID NO: 84, CDR2 is SEQ ID NO: 144, and CDR3 is SEQ ID NO: 204;
CDR1 is SEQ ID NO: 85, CDR2 is SEQ ID NO: 145, and CDR3 is SEQ ID NO: 205;
CDR1 is SEQ ID NO: 86, CDR2 is SEQ ID NO: 146, and CDR3 is SEQ ID NO: 206;
CDR1 is SEQ ID NO: 87, CDR2 is SEQ ID NO: 147, and CDR3 is SEQ ID NO: 207;
CDR1 is SEQ ID NO: 88, CDR2 is SEQ ID NO: 148, and CDR3 is SEQ ID NO: 208;
CDR1 is SEQ ID NO: 89, CDR2 is SEQ ID NO: 149, and CDR3 is SEQ ID NO: 209;
CDR1 is SEQ ID NO: 90, CDR2 is SEQ ID NO: 150, and CDR3 is SEQ ID NO: 210;
CDR1 is SEQ ID NO: 91, CDR2 is SEQ ID NO: 151, and CDR3 is SEQ ID NO: 211;
CDR1 is SEQ ID NO: 92, CDR2 is SEQ ID NO: 152, and CDR3 is SEQ ID NO: 212;
CDR1 is SEQ ID NO: 93, CDR2 is SEQ ID NO: 153, and CDR3 is SEQ ID NO: 213;
CDR1 is SEQ ID NO: 94, CDR2 is SEQ ID NO: 154, and CDR3 is SEQ ID NO: 214;
CDR1 is SEQ ID NO: 95, CDR2 is SEQ ID NO: 155, and CDR3 is SEQ ID NO: 215; and
CDR1 is SEQ ID NO: 96, CDR2 is SEQ ID NO: 156, and CDR3 is SEQ ID NO: 216.

2. The immunoglobulin single variable domain according to claim 1, wherein the framework regions (FRs) have a sequence identity of more than 80% with the FRs of SEQ ID NOs: 37-66 (FR1), SEQ ID NOs: 97-126 (FR2), SEQ ID NOs: 157-186 (FR3), and SEQ ID NOs: 217-246 (FR4).

3. The immunoglobulin single variable domain of claim 1, wherein the immunoglobulin single variable domain comprises a peptide selected from the group consisting of SEQ ID NOs: 7-36 or a peptide that has at least 80% sequence identity with a peptide selected from the group consisting of SEQ ID NOs: 7-36.

4. An immunoglobulin single variable domain that is directed against human macrophage mannose receptor (SEQ ID NO: 1), wherein the immunoglobulin single variable domain comprises a peptide that comprises four framework regions (FRs) and three complementarity-determining regions (CDRs), wherein the immunoglobulin single variable domain is selected from the group consisting of SEQ ID NOs: 7, 8, 9 and 10.

5. The immunoglobulin single variable domain of claim 1, wherein said immunoglobulin single variable domain is fused to a detectable label.

6. The immunoglobulin single variable domain according to claim 5, wherein said detectable label is a radionuclide.

7. The immunoglobulin single variable domain of claim 1, wherein said immunoglobulin single variable domain is fused to a functional moiety.

8. The immunoglobulin single variable domain according to claim 7, wherein said functional moiety is a therapeutically active agent.

9. A polypeptide comprising the immunoglobulin single variable domain of claim 1.

10. A polynucleotide encoding the immunoglobulin single variable domain of claim 1.

11. A pharmaceutical composition comprising the immunoglobulin single variable domain of claim 1, and at least one of a pharmaceutically acceptable carrier, adjuvant or diluent.

12. A method of non-invasive in vivo medical imaging, the method comprising:
administering to a subject suspected of having cancer the immunoglobulin single variable domain of claim 1 as a contrast agent in non-invasive in vivo medical imaging of the subject.

13. The immunoglobulin single variable domain of claim 1, wherein the immunoglobulin single variable domain specifically targets MMR-positive tumor-associated macrophages (TAMs) inside a tumor.

14. A method for producing a immunoglobulin single variable domain, said method comprising the steps of:
expressing, in a suitable host cell or a suitable expression system, the polynucleotide of claim 10; and
isolating and/or purifying the immunoglobulin single variable domain therefrom.

15. An immunoglobulin single variable domain that is directed against human macrophage mannose receptor (SEQ ID NO: 1), which immunoglobulin single variable domain comprises a peptide selected from the group consisting of SEQ ID NOs: 7-36.

16. The immunoglobulin single variable domain of claim 2, which is fused to a detectable label or functional moiety.

17. The immunoglobulin single variable domain of claim 3, which is fused to a detectable label or functional moiety.

18. The immunoglobulin single variable domain of claim 4, wherein the immunoglobulin single variable domain is SEQ ID NO: 7.

19. The immunoglobulin single variable domain of claim 4, wherein the immunoglobulin single variable domain is SEQ ID NO: 8.

20. The immunoglobulin single variable domain of claim 4, wherein the immunoglobulin single variable domain is SEQ ID NO: 9.

21. The immunoglobulin single variable domain of claim 4, wherein the immunoglobulin single variable domain is SEQ ID NO: 10.

* * * * *

UNITED STATES PATENT AND TRADEMARK OFFICE
CERTIFICATE OF CORRECTION

PATENT NO. : 9,556,273 B2
APPLICATION NO. : 14/402301
DATED : January 31, 2017
INVENTOR(S) : Van Ginderachter et al.

Page 1 of 1

It is certified that error appears in the above-identified patent and that said Letters Patent is hereby corrected as shown below:

In the Specification

In Column 36, Line 61, please replace:
"DNAKNTAYLQMNSLKPEDTGIYSCAAGFVCYKYDYW"
With:
--DNAKNTAYLQMNSLKPEDTGIYSCAAGFVCYNYDYW--

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 262

<210> SEQ ID NO 1
<211> LENGTH: 1456
<212> TYPE: PRT
<213> ORGANISM: Homo sapiens

<400> SEQUENCE: 1
```

Met Arg Leu Pro Leu Leu Leu Val Phe Ala Ser Val Ile Pro Gly Ala
1               5                   10                  15

Val Leu Leu Leu Asp Thr Arg Gln Phe Leu Ile Tyr Asn Glu Asp His
            20                  25                  30

Lys Arg Cys Val Asp Ala Val Ser Pro Ser Ala Val Gln Thr Ala Ala
        35                  40                  45

Cys Asn Gln Asp Ala Glu Ser Gln Lys Phe Arg Trp Val Ser Glu Ser
    50                  55                  60

Gln Ile Met Ser Val Ala Phe Lys Leu Cys Leu Gly Val Pro Ser Lys
65                  70                  75                  80

Thr Asp Trp Val Ala Ile Thr Leu Tyr Ala Cys Asp Ser Lys Ser Glu
                85                  90                  95

Phe Gln Lys Trp Glu Cys Lys Asn Asp Thr Leu Leu Gly Ile Lys Gly
            100                 105                 110

Glu Asp Leu Phe Phe Asn Tyr Gly Asn Arg Gln Glu Lys Asn Ile Met
        115                 120                 125

Leu Tyr Lys Gly Ser Gly Leu Trp Ser Arg Trp Lys Ile Tyr Gly Thr
    130                 135                 140

Thr Asp Asn Leu Cys Ser Arg Gly Tyr Glu Ala Met Tyr Thr Leu Leu
145                 150                 155                 160

Gly Asn Ala Asn Gly Ala Thr Cys Ala Phe Pro Phe Lys Phe Glu Asn
                165                 170                 175

Lys Trp Tyr Ala Asp Cys Thr Ser Ala Gly Arg Ser Asp Gly Trp Leu
            180                 185                 190

Trp Cys Gly Thr Thr Thr Asp Tyr Asp Thr Asp Lys Leu Phe Gly Tyr
        195                 200                 205

Cys Pro Leu Lys Phe Glu Gly Ser Glu Ser Leu Trp Asn Lys Asp Pro
    210                 215                 220

Leu Thr Ser Val Ser Tyr Gln Ile Asn Ser Lys Ser Ala Leu Thr Trp
225                 230                 235                 240

His Gln Ala Arg Lys Ser Cys Gln Gln Gln Asn Ala Glu Leu Leu Ser
                245                 250                 255

```
Ile Thr Glu Ile His Glu Gln Thr Tyr Leu Thr Gly Leu Thr Ser Ser
            260                 265                 270

Leu Thr Ser Gly Leu Trp Ile Gly Leu Asn Ser Leu Ser Phe Asn Ser
        275                 280                 285

Gly Trp Gln Trp Ser Asp Arg Ser Pro Phe Arg Tyr Leu Asn Trp Leu
    290                 295                 300

Pro Gly Ser Pro Ser Ala Glu Pro Gly Lys Ser Cys Val Ser Leu Asn
305                 310                 315                 320

Pro Gly Lys Asn Ala Lys Trp Glu Asn Leu Glu Cys Val Gln Lys Leu
                325                 330                 335

Gly Tyr Ile Cys Lys Lys Gly Asn Thr Thr Leu Asn Ser Phe Val Ile
            340                 345                 350

Pro Ser Glu Ser Asp Val Pro Thr His Cys Pro Ser Gln Trp Trp Pro
        355                 360                 365

Tyr Ala Gly His Cys Tyr Lys Ile His Arg Asp Glu Lys Lys Ile Gln
    370                 375                 380

Arg Asp Ala Leu Thr Thr Cys Arg Lys Glu Gly Gly Asp Leu Thr Ser
385                 390                 395                 400

Ile His Thr Ile Glu Glu Leu Asp Phe Ile Ile Ser Gln Leu Gly Tyr
                405                 410                 415

Glu Pro Asn Asp Glu Leu Trp Ile Gly Leu Asn Asp Ile Lys Ile Gln
            420                 425                 430

Met Tyr Phe Glu Trp Ser Asp Gly Thr Pro Val Thr Phe Thr Lys Trp
        435                 440                 445

Leu Arg Gly Glu Pro Ser His Glu Asn Asn Arg Gln Glu Asp Cys Val
450                 455                 460

Val Met Lys Gly Lys Asp Gly Tyr Trp Ala Asp Arg Gly Cys Glu Trp
465                 470                 475                 480

Pro Leu Gly Tyr Ile Cys Lys Met Lys Ser Arg Ser Gln Gly Pro Glu
                485                 490                 495

Ile Val Glu Val Glu Lys Gly Cys Arg Lys Gly Trp Lys Lys His His
            500                 505                 510

Phe Tyr Cys Tyr Met Ile Gly His Thr Leu Ser Thr Phe Ala Glu Ala
        515                 520                 525

Asn Gln Thr Cys Asn Asn Glu Asn Ala Tyr Leu Thr Thr Ile Glu Asp
530                 535                 540

Arg Tyr Glu Gln Ala Phe Leu Thr Ser Phe Val Gly Leu Arg Pro Glu
545                 550                 555                 560

Lys Tyr Phe Trp Thr Gly Leu Ser Asp Ile Gln Thr Lys Gly Thr Phe
                565                 570                 575

Gln Trp Thr Ile Glu Glu Val Arg Phe Thr His Trp Asn Ser Asp
            580                 585                 590

Met Pro Gly Arg Lys Pro Gly Cys Val Ala Met Arg Thr Gly Ile Ala
        595                 600                 605

Gly Gly Leu Trp Asp Val Leu Lys Cys Asp Glu Lys Ala Lys Phe Val
    610                 615                 620

Cys Lys His Trp Ala Glu Gly Val Thr His Pro Pro Lys Pro Thr Thr
625                 630                 635                 640

Thr Pro Glu Pro Lys Cys Pro Glu Asp Trp Gly Ala Ser Ser Arg Thr
                645                 650                 655

Ser Leu Cys Phe Lys Leu Tyr Ala Lys Gly Lys His Glu Lys Lys Thr
            660                 665                 670

Trp Phe Glu Ser Arg Asp Phe Cys Arg Ala Leu Gly Gly Asp Leu Ala
```

-continued

```
            675                 680                 685
Ser Ile Asn Asn Lys Glu Glu Gln Gln Thr Ile Trp Arg Leu Ile Thr
        690                 695                 700
Ala Ser Gly Ser Tyr His Lys Leu Phe Trp Leu Gly Leu Thr Tyr Gly
705                 710                 715                 720
Ser Pro Ser Glu Gly Phe Thr Trp Ser Asp Gly Ser Pro Val Ser Tyr
                725                 730                 735
Glu Asn Trp Ala Tyr Gly Glu Pro Asn Asn Tyr Gln Asn Val Glu Tyr
            740                 745                 750
Cys Gly Glu Leu Lys Gly Asp Pro Thr Met Ser Trp Asn Asp Ile Asn
        755                 760                 765
Cys Glu His Leu Asn Asn Trp Ile Cys Gln Ile Gln Lys Gly Gln Thr
    770                 775                 780
Pro Lys Pro Glu Pro Thr Pro Ala Pro Gln Asp Asn Pro Pro Val Thr
785                 790                 795                 800
Glu Asp Gly Trp Val Ile Tyr Lys Asp Tyr Gln Tyr Tyr Phe Ser Lys
                805                 810                 815
Glu Lys Glu Thr Met Asp Asn Ala Arg Ala Phe Cys Lys Arg Asn Phe
            820                 825                 830
Gly Asp Leu Val Ser Ile Gln Ser Glu Ser Glu Lys Lys Phe Leu Trp
        835                 840                 845
Lys Tyr Val Asn Arg Asn Asp Ala Gln Ser Ala Tyr Phe Ile Gly Leu
    850                 855                 860
Leu Ile Ser Leu Asp Lys Lys Phe Ala Trp Met Asp Gly Ser Lys Val
865                 870                 875                 880
Asp Tyr Val Ser Trp Ala Thr Gly Glu Pro Asn Phe Ala Asn Glu Asp
                885                 890                 895
Glu Asn Cys Val Thr Met Tyr Ser Asn Ser Gly Phe Trp Asn Asp Ile
            900                 905                 910
Asn Cys Gly Tyr Pro Asn Ala Phe Ile Cys Gln Arg His Asn Ser Ser
        915                 920                 925
Ile Asn Ala Thr Thr Val Met Pro Thr Met Pro Ser Val Pro Ser Gly
    930                 935                 940
Cys Lys Glu Gly Trp Asn Phe Tyr Ser Asn Lys Cys Phe Lys Ile Phe
945                 950                 955                 960
Gly Phe Met Glu Glu Glu Arg Lys Asn Trp Gln Glu Ala Arg Lys Ala
                965                 970                 975
Cys Ile Gly Phe Gly Gly Asn Leu Val Ser Ile Gln Asn Glu Lys Glu
            980                 985                 990
Gln Ala Phe Leu Thr Tyr His Met Lys Asp Ser Thr Phe Ser Ala Trp
        995                 1000                1005
Thr Gly Leu Asn Asp Val Asn Ser Glu His Thr Phe Leu Trp Thr
    1010                1015                1020
Asp Gly Arg Gly Val His Tyr Thr Asn Trp Gly Lys Gly Tyr Pro
    1025                1030                1035
Gly Gly Arg Arg Ser Ser Leu Ser Tyr Glu Asp Ala Asp Cys Val
    1040                1045                1050
Val Ile Ile Gly Gly Ala Ser Asn Glu Ala Gly Lys Trp Met Asp
    1055                1060                1065
Asp Thr Cys Asp Ser Lys Arg Gly Tyr Ile Cys Gln Thr Arg Ser
    1070                1075                1080
Asp Pro Ser Leu Thr Asn Pro Pro Ala Thr Ile Gln Thr Asp Gly
    1085                1090                1095
```

Phe Val Lys Tyr Gly Lys Ser Ser Tyr Ser Leu Met Arg Gln Lys
1100                1105                1110

Phe Gln Trp His Glu Ala Glu Thr Tyr Cys Lys Leu His Asn Ser
1115                1120                1125

Leu Ile Ala Ser Ile Leu Asp Pro Tyr Ser Asn Ala Phe Ala Trp
1130                1135                1140

Leu Gln Met Glu Thr Ser Asn Glu Arg Val Trp Ile Ala Leu Asn
1145                1150                1155

Ser Asn Leu Thr Asp Asn Gln Tyr Thr Trp Thr Asp Lys Trp Arg
1160                1165                1170

Val Arg Tyr Thr Asn Trp Ala Ala Asp Glu Pro Lys Leu Lys Ser
1175                1180                1185

Ala Cys Val Tyr Leu Asp Leu Asp Gly Tyr Trp Lys Thr Ala His
1190                1195                1200

Cys Asn Glu Ser Phe Tyr Phe Leu Cys Lys Arg Ser Asp Glu Ile
1205                1210                1215

Pro Ala Thr Glu Pro Pro Gln Leu Pro Gly Arg Cys Pro Glu Ser
1220                1225                1230

Asp His Thr Ala Trp Ile Pro Phe His Gly His Cys Tyr Tyr Ile
1235                1240                1245

Glu Ser Ser Tyr Thr Arg Asn Trp Gly Gln Ala Ser Leu Glu Cys
1250                1255                1260

Leu Arg Met Gly Ser Ser Leu Val Ser Ile Glu Ser Ala Ala Glu
1265                1270                1275

Ser Ser Phe Leu Ser Tyr Arg Val Glu Pro Leu Lys Ser Lys Thr
1280                1285                1290

Asn Phe Trp Ile Gly Leu Phe Arg Asn Val Glu Gly Thr Trp Leu
1295                1300                1305

Trp Ile Asn Asn Ser Pro Val Ser Phe Val Asn Trp Asn Thr Gly
1310                1315                1320

Asp Pro Ser Gly Glu Arg Asn Asp Cys Val Ala Leu His Ala Ser
1325                1330                1335

Ser Gly Phe Trp Ser Asn Ile His Cys Ser Ser Tyr Lys Gly Tyr
1340                1345                1350

Ile Cys Lys Arg Pro Lys Ile Ile Asp Ala Lys Pro Thr His Glu
1355                1360                1365

Leu Leu Thr Thr Lys Ala Asp Thr Arg Lys Met Asp Pro Ser Lys
1370                1375                1380

Pro Ser Ser Asn Val Ala Gly Val Val Ile Val Ile Leu Leu
1385                1390                1395

Ile Leu Thr Gly Ala Gly Leu Ala Ala Tyr Phe Phe Tyr Lys Lys
1400                1405                1410

Arg Arg Val His Leu Pro Gln Glu Gly Ala Phe Glu Asn Thr Leu
1415                1420                1425

Tyr Phe Asn Ser Gln Ser Ser Pro Gly Thr Ser Asp Met Lys Asp
1430                1435                1440

Leu Val Gly Asn Ile Glu Gln Asn Glu His Ser Val Ile
1445                1450                1455

<210> SEQ ID NO 2
<211> LENGTH: 1371
<212> TYPE: PRT
<213> ORGANISM: Homo sapiens

<400> SEQUENCE: 2

```
Leu Leu Asp Thr Arg Gln Phe Leu Ile Tyr Asn Glu Asp His Lys Arg
1               5                   10                  15

Cys Val Asp Ala Val Ser Pro Ser Ala Val Gln Thr Ala Ala Cys Asn
            20                  25                  30

Gln Asp Ala Glu Ser Gln Lys Phe Arg Trp Val Ser Glu Ser Gln Ile
            35                  40                  45

Met Ser Val Ala Phe Lys Leu Cys Leu Gly Val Pro Ser Lys Thr Asp
    50                  55                  60

Trp Val Ala Ile Thr Leu Tyr Ala Cys Asp Ser Lys Ser Glu Phe Gln
65                  70                  75                  80

Lys Trp Glu Cys Lys Asn Asp Thr Leu Leu Gly Ile Lys Gly Glu Asp
                85                  90                  95

Leu Phe Phe Asn Tyr Gly Asn Arg Gln Glu Lys Asn Ile Met Leu Tyr
            100                 105                 110

Lys Gly Ser Gly Leu Trp Ser Arg Trp Lys Ile Tyr Gly Thr Thr Asp
            115                 120                 125

Asn Leu Cys Ser Arg Gly Tyr Glu Ala Met Tyr Thr Leu Leu Gly Asn
130                 135                 140

Ala Asn Gly Ala Thr Cys Ala Phe Pro Phe Lys Phe Glu Asn Lys Trp
145                 150                 155                 160

Tyr Ala Asp Cys Thr Ser Ala Gly Arg Ser Asp Gly Trp Leu Trp Cys
                165                 170                 175

Gly Thr Thr Thr Asp Tyr Asp Thr Asp Lys Leu Phe Gly Tyr Cys Pro
            180                 185                 190

Leu Lys Phe Glu Gly Ser Glu Ser Leu Trp Asn Lys Asp Pro Leu Thr
            195                 200                 205

Ser Val Ser Tyr Gln Ile Asn Ser Lys Ser Ala Leu Thr Trp His Gln
210                 215                 220

Ala Arg Lys Ser Cys Gln Gln Asn Ala Glu Leu Leu Ser Ile Thr
225                 230                 235                 240

Glu Ile His Glu Gln Thr Tyr Leu Thr Gly Leu Thr Ser Ser Leu Thr
                245                 250                 255

Ser Gly Leu Trp Ile Gly Leu Asn Ser Leu Ser Phe Asn Ser Gly Trp
            260                 265                 270

Gln Trp Ser Asp Arg Ser Pro Phe Arg Tyr Leu Asn Trp Leu Pro Gly
            275                 280                 285

Ser Pro Ser Ala Glu Pro Gly Lys Ser Cys Val Ser Leu Asn Pro Gly
290                 295                 300

Lys Asn Ala Lys Trp Glu Asn Leu Glu Cys Val Gln Lys Leu Gly Tyr
305                 310                 315                 320

Ile Cys Lys Lys Gly Asn Thr Thr Leu Asn Ser Phe Val Ile Pro Ser
                325                 330                 335

Glu Ser Asp Val Pro Thr His Cys Pro Ser Gln Trp Trp Pro Tyr Ala
            340                 345                 350

Gly His Cys Tyr Lys Ile His Arg Asp Glu Lys Lys Ile Gln Arg Asp
            355                 360                 365

Ala Leu Thr Thr Cys Arg Lys Glu Gly Gly Asp Leu Ala Ser Ile His
370                 375                 380

Thr Ile Glu Glu Phe Asp Phe Ile Ile Ser Gln Leu Gly Tyr Glu Pro
385                 390                 395                 400

Asn Asp Glu Leu Trp Ile Gly Leu Asn Asp Ile Lys Ile Gln Met Tyr
            405                 410                 415
```

```
Phe Glu Trp Ser Asp Gly Thr Pro Val Thr Phe Thr Lys Trp Leu Arg
            420                 425                 430

Gly Glu Pro Ser His Glu Asn Asn Arg Gln Glu Asp Cys Val Val Met
            435                 440                 445

Lys Gly Lys Asp Gly Tyr Trp Ala Asp Arg Gly Cys Glu Trp Pro Leu
450                 455                 460

Gly Tyr Ile Cys Lys Met Lys Ser Arg Ser Gln Gly Pro Glu Ile Val
465                 470                 475                 480

Glu Val Glu Lys Gly Cys Arg Lys Gly Trp Lys His His Phe Tyr
                485                 490                 495

Cys Tyr Met Ile Gly His Thr Leu Ser Thr Phe Ala Glu Ala Asn Gln
            500                 505                 510

Thr Cys Asn Asn Glu Asn Ala Tyr Leu Thr Thr Ile Glu Asp Arg Tyr
            515                 520                 525

Glu Gln Ala Phe Leu Thr Ser Phe Val Gly Leu Arg Pro Glu Lys Tyr
            530                 535                 540

Phe Trp Thr Gly Leu Ser Asp Ile Gln Thr Lys Gly Thr Phe Gln Trp
545                 550                 555                 560

Thr Ile Glu Glu Glu Val Arg Phe Thr His Trp Asn Ser Asp Met Pro
                565                 570                 575

Gly Arg Lys Pro Gly Cys Val Ala Met Arg Thr Gly Ile Ala Gly Gly
            580                 585                 590

Leu Trp Asp Val Leu Lys Cys Asp Glu Lys Ala Lys Phe Val Cys Lys
            595                 600                 605

His Trp Ala Glu Gly Val Thr His Pro Pro Lys Pro Thr Thr Thr Pro
            610                 615                 620

Glu Pro Lys Cys Pro Glu Asp Trp Gly Ala Ser Ser Arg Thr Ser Leu
625                 630                 635                 640

Cys Phe Lys Leu Tyr Ala Lys Gly Lys His Glu Lys Lys Thr Trp Phe
                645                 650                 655

Glu Ser Arg Asp Phe Cys Arg Ala Leu Gly Gly Asp Leu Ala Ser Ile
            660                 665                 670

Asn Asn Lys Glu Glu Gln Gln Thr Ile Trp Arg Leu Ile Thr Ala Ser
            675                 680                 685

Gly Ser Tyr His Lys Leu Phe Trp Leu Gly Leu Thr Tyr Gly Ser Pro
            690                 695                 700

Ser Glu Gly Phe Thr Trp Ser Asp Gly Ser Pro Val Ser Tyr Glu Asn
705                 710                 715                 720

Trp Ala Tyr Gly Glu Pro Asn Asn Tyr Gln Asn Val Glu Tyr Cys Gly
                725                 730                 735

Glu Leu Lys Gly Asp Pro Thr Met Ser Trp Asn Asp Ile Asn Cys Glu
            740                 745                 750

His Leu Asn Asn Trp Ile Cys Gln Ile Gln Lys Gly Gln Thr Pro Lys
            755                 760                 765

Pro Glu Pro Thr Pro Ala Pro Gln Asp Asn Pro Pro Val Thr Glu Asp
            770                 775                 780

Gly Trp Val Ile Tyr Lys Asp Tyr Gln Tyr Tyr Phe Ser Lys Glu Lys
785                 790                 795                 800

Glu Thr Met Asp Asn Ala Arg Ala Phe Cys Lys Arg Asn Phe Gly Asp
                805                 810                 815

Leu Val Ser Ile Gln Ser Glu Ser Glu Lys Lys Phe Leu Trp Lys Tyr
            820                 825                 830
```

```
Val Asn Arg Asn Asp Ala Gln Ser Ala Tyr Phe Ile Gly Leu Leu Ile
            835                 840                 845

Ser Leu Asp Lys Lys Phe Ala Trp Met Asp Gly Ser Lys Val Asp Tyr
        850                 855                 860

Val Ser Trp Ala Thr Gly Glu Pro Asn Phe Ala Asn Glu Asp Glu Asn
865                 870                 875                 880

Cys Val Thr Met Tyr Ser Asn Ser Gly Phe Trp Asn Asp Ile Asn Cys
                885                 890                 895

Gly Tyr Pro Asn Ala Phe Ile Cys Gln Arg His Asn Ser Ile Asn
            900                 905                 910

Ala Thr Thr Val Met Pro Thr Met Pro Ser Val Pro Ser Gly Cys Lys
        915                 920                 925

Glu Gly Trp Asn Phe Tyr Ser Asn Lys Cys Phe Lys Ile Phe Gly Phe
    930                 935                 940

Met Glu Glu Glu Arg Lys Asn Trp Gln Glu Ala Arg Lys Ala Cys Ile
945                 950                 955                 960

Gly Phe Gly Gly Asn Leu Val Ser Ile Gln Asn Glu Lys Glu Gln Ala
                965                 970                 975

Phe Leu Thr Tyr His Met Lys Asp Ser Thr Phe Ser Ala Trp Thr Gly
            980                 985                 990

Leu Asn Asp Val Asn Ser Glu His  Thr Phe Leu Trp Thr  Asp Gly Arg
            995                 1000                 1005

Gly Val  His Tyr Thr Asn Trp  Gly Lys Gly Tyr Pro  Gly Gly Arg
     1010                 1015                 1020

Arg Ser  Ser Leu Ser Tyr Glu  Asp Ala Asp Cys Val  Val Ile Ile
     1025                 1030                 1035

Gly Gly  Ala Ser Asn Glu Ala  Gly Lys Trp Met Asp  Asp Thr Cys
     1040                 1045                 1050

Asp Ser  Lys Arg Gly Tyr Ile  Cys Gln Thr Arg Ser  Asp Pro Ser
     1055                 1060                 1065

Leu Thr  Asn Pro Pro Ala Thr  Ile Gln Thr Asp Gly  Phe Val Lys
     1070                 1075                 1080

Tyr Gly  Lys Ser Ser Tyr Ser  Leu Met Arg Gln Lys  Phe Gln Trp
     1085                 1090                 1095

His Glu  Ala Glu Thr Tyr Cys  Lys Leu His Asn Ser  Leu Ile Ala
     1100                 1105                 1110

Ser Ile  Leu Asp Pro Tyr Ser  Asn Ala Phe Ala Trp  Leu Gln Met
     1115                 1120                 1125

Glu Thr  Ser Asn Glu Arg Val  Trp Ile Ala Leu Asn  Ser Asn Leu
     1130                 1135                 1140

Thr Asp  Asn Gln Tyr Thr Trp  Thr Asp Lys Trp Arg  Val Arg Tyr
     1145                 1150                 1155

Thr Asn  Trp Ala Ala Asp Glu  Pro Lys Leu Lys Ser  Ala Cys Val
     1160                 1165                 1170

Tyr Leu  Asp Leu Asp Gly Tyr  Trp Lys Thr Ala His  Cys Asn Glu
     1175                 1180                 1185

Ser Phe  Tyr Phe Leu Cys Lys  Arg Ser Asp Glu Ile  Pro Ala Thr
     1190                 1195                 1200

Glu Pro  Pro Gln Leu Pro Gly  Arg Cys Pro Glu Ser  Asp His Thr
     1205                 1210                 1215

Ala Trp  Ile Pro Phe His Gly  His Cys Tyr Tyr Ile  Glu Ser Ser
     1220                 1225                 1230

Tyr Thr  Arg Asn Trp Gly Gln  Ala Ser Leu Glu Cys  Leu Arg Met
```

```
            1235                1240                1245

Gly Ser Ser Leu Val Ser Ile Glu Ser Ala Ala Glu Ser Ser Phe
        1250                1255                1260

Leu Ser Tyr Arg Val Glu Pro Leu Lys Ser Lys Thr Asn Phe Trp
        1265                1270                1275

Ile Gly Leu Phe Arg Asn Val Glu Gly Thr Trp Leu Trp Ile Asn
        1280                1285                1290

Asn Ser Pro Val Ser Phe Val Asn Trp Asn Thr Gly Asp Pro Ser
        1295                1300                1305

Gly Glu Arg Asn Asp Cys Val Ala Leu His Ala Ser Ser Gly Phe
        1310                1315                1320

Trp Ser Asn Ile His Cys Ser Ser Tyr Lys Gly Tyr Ile Cys Lys
        1325                1330                1335

Arg Pro Lys Ile Ile Asp Ala Lys Pro Thr His Glu Leu Leu Thr
        1340                1345                1350

Thr Lys Ala Asp Thr Arg Lys Met Asp Pro Ser Lys His His His
        1355                1360                1365

His His His
        1370

<210> SEQ ID NO 3
<211> LENGTH: 1456
<212> TYPE: PRT
<213> ORGANISM: Mus musculus

<400> SEQUENCE: 3

Met Arg Leu Leu Leu Leu Ala Phe Ile Ser Val Ile Pro Val Ser
1                   5                   10                  15

Val Gln Leu Leu Asp Ala Arg Gln Phe Leu Ile Tyr Asn Glu Asp His
                20                  25                  30

Lys Arg Cys Val Asp Ala Leu Ser Ala Ile Ser Val Gln Thr Ala Thr
            35                  40                  45

Cys Asn Pro Glu Ala Glu Ser Gln Lys Phe Arg Trp Val Ser Asp Ser
    50                  55                  60

Gln Ile Met Ser Val Ala Phe Lys Leu Cys Leu Gly Val Pro Ser Lys
65                  70                  75                  80

Thr Asp Trp Ala Ser Val Thr Leu Tyr Ala Cys Asp Ser Lys Ser Glu
                85                  90                  95

Tyr Gln Lys Trp Glu Cys Lys Asn Asp Thr Leu Phe Gly Ile Lys Gly
            100                 105                 110

Thr Glu Leu Tyr Phe Asn Tyr Gly Asn Arg Gln Glu Lys Asn Ile Lys
        115                 120                 125

Leu Tyr Lys Gly Ser Gly Leu Trp Ser Arg Trp Lys Val Tyr Gly Thr
    130                 135                 140

Thr Asp Asp Leu Cys Ser Arg Gly Tyr Glu Ala Met Tyr Ser Leu Leu
145                 150                 155                 160

Gly Asn Ala Asn Gly Ala Val Cys Ala Phe Pro Phe Lys Phe Glu Asn
                165                 170                 175

Lys Trp Tyr Ala Asp Cys Thr Ser Ala Gly Arg Ser Asp Gly Trp Leu
            180                 185                 190

Trp Cys Gly Thr Thr Thr Asp Tyr Asp Lys Asp Lys Leu Phe Gly Phe
        195                 200                 205

Cys Pro Leu His Phe Glu Gly Ser Glu Arg Leu Trp Asn Lys Asp Pro
    210                 215                 220
```

```
Leu Thr Gly Ile Leu Tyr Gln Ile Asn Ser Lys Ser Ala Leu Thr Trp
225                 230                 235                 240

His Gln Ala Arg Ala Ser Cys Lys Gln Gln Asn Ala Asp Leu Leu Ser
                245                 250                 255

Val Thr Glu Ile His Glu Gln Met Tyr Leu Thr Gly Leu Thr Ser Ser
            260                 265                 270

Leu Ser Ser Gly Leu Trp Ile Gly Leu Asn Ser Leu Ser Val Arg Ser
        275                 280                 285

Gly Trp Gln Trp Ala Gly Gly Ser Pro Phe Arg Tyr Leu Asn Trp Leu
    290                 295                 300

Pro Gly Ser Pro Ser Ser Glu Pro Gly Lys Ser Cys Val Ser Leu Asn
305                 310                 315                 320

Pro Gly Lys Asn Ala Lys Trp Glu Asn Leu Glu Cys Val Gln Lys Leu
                325                 330                 335

Gly Tyr Ile Cys Lys Lys Gly Asn Asn Thr Leu Asn Pro Phe Ile Ile
                340                 345                 350

Pro Ser Ala Ser Asp Val Pro Thr Gly Cys Pro Asn Gln Trp Trp Pro
            355                 360                 365

Tyr Ala Gly His Cys Tyr Arg Ile His Arg Glu Glu Lys Lys Ile Gln
    370                 375                 380

Lys Tyr Ala Leu Gln Ala Cys Arg Lys Glu Gly Gly Asp Leu Ala Ser
385                 390                 395                 400

Ile His Ser Ile Glu Glu Phe Asp Phe Ile Phe Ser Gln Leu Gly Tyr
                405                 410                 415

Glu Pro Asn Asp Glu Leu Trp Ile Gly Leu Asn Asp Ile Lys Ile Gln
            420                 425                 430

Met Tyr Phe Glu Trp Ser Asp Gly Thr Pro Val Thr Phe Thr Lys Trp
    435                 440                 445

Leu Pro Gly Glu Pro Ser His Glu Asn Asn Arg Gln Glu Asp Cys Val
450                 455                 460

Val Met Lys Gly Lys Asp Gly Tyr Trp Ala Asp Arg Ala Cys Glu Gln
465                 470                 475                 480

Pro Leu Gly Tyr Ile Cys Lys Met Val Ser Gln Ser His Ala Val Val
                485                 490                 495

Pro Glu Gly Ala Asp Lys Gly Cys Arg Lys Gly Trp Lys Arg His Gly
            500                 505                 510

Phe Tyr Cys Tyr Leu Ile Gly Ser Thr Leu Ser Thr Phe Thr Asp Ala
    515                 520                 525

Asn His Thr Cys Thr Asn Glu Lys Ala Tyr Leu Thr Thr Val Glu Asp
530                 535                 540

Arg Tyr Glu Gln Ala Phe Leu Thr Ser Leu Val Gly Leu Arg Pro Glu
545                 550                 555                 560

Lys Tyr Phe Trp Thr Gly Leu Ser Asp Val Gln Asn Lys Gly Thr Phe
                565                 570                 575

Arg Trp Thr Val Asp Glu Gln Val Gln Phe Thr His Trp Asn Ala Asp
            580                 585                 590

Met Pro Gly Arg Lys Ala Gly Cys Val Ala Met Lys Thr Gly Val Ala
    595                 600                 605

Gly Gly Leu Trp Asp Val Leu Ser Cys Glu Glu Lys Ala Lys Phe Val
        610                 615                 620

Cys Lys His Trp Ala Glu Gly Val Thr Arg Pro Pro Glu Pro Thr Thr
625                 630                 635                 640

Thr Pro Glu Pro Lys Cys Pro Glu Asn Trp Gly Thr Thr Ser Lys Thr
```

```
            645                 650                 655
Ser Met Cys Phe Lys Leu Tyr Ala Lys Gly Lys His Glu Lys Lys Thr
            660                 665                 670

Trp Phe Glu Ser Arg Asp Phe Cys Lys Ala Ile Gly Gly Glu Leu Ala
            675                 680                 685

Ser Ile Lys Ser Lys Asp Glu Gln Gln Val Ile Trp Arg Leu Ile Thr
            690                 695                 700

Ser Ser Gly Ser Tyr His Glu Leu Phe Trp Leu Gly Leu Thr Tyr Gly
705                 710                 715                 720

Ser Pro Ser Glu Gly Phe Thr Trp Ser Asp Gly Ser Pro Val Ser Tyr
            725                 730                 735

Glu Asn Trp Ala Tyr Gly Glu Pro Asn Asn Tyr Gln Asn Val Glu Tyr
            740                 745                 750

Cys Gly Glu Leu Lys Gly Asp Pro Gly Met Ser Trp Asn Asp Ile Asn
            755                 760                 765

Cys Glu His Leu Asn Asn Trp Ile Cys Gln Ile Gln Lys Gly Lys Thr
            770                 775                 780

Leu Leu Pro Glu Pro Thr Pro Ala Pro Gln Asp Asn Pro Pro Val Thr
785                 790                 795                 800

Ala Asp Gly Trp Val Ile Tyr Lys Asp Tyr Gln Tyr Tyr Phe Ser Lys
                    805                 810                 815

Glu Lys Glu Thr Met Asp Asn Ala Arg Ala Phe Cys Lys Lys Asn Phe
            820                 825                 830

Gly Asp Leu Ala Thr Ile Lys Ser Glu Ser Glu Lys Lys Phe Leu Trp
            835                 840                 845

Lys Tyr Ile Asn Lys Asn Gly Gly Gln Ser Pro Tyr Phe Ile Gly Met
850                 855                 860

Leu Ile Ser Met Asp Lys Lys Phe Ile Trp Met Asp Gly Ser Lys Val
865                 870                 875                 880

Asp Phe Val Ala Trp Ala Thr Gly Glu Pro Asn Phe Ala Asn Asp Asp
                    885                 890                 895

Glu Asn Cys Val Thr Met Tyr Thr Asn Ser Gly Phe Trp Asn Asp Ile
                    900                 905                 910

Asn Cys Gly Tyr Pro Asn Asn Phe Ile Cys Gln Arg His Asn Ser Ser
            915                 920                 925

Ile Asn Ala Thr Ala Met Pro Thr Thr Pro Thr Thr Pro Gly Gly Cys
930                 935                 940

Lys Glu Gly Trp His Leu Tyr Lys Asn Lys Cys Phe Lys Ile Phe Gly
945                 950                 955                 960

Phe Ala Asn Glu Glu Lys Lys Ser Trp Gln Asp Ala Arg Gln Ala Cys
                    965                 970                 975

Lys Gly Leu Lys Gly Asn Leu Val Ser Ile Glu Asn Ala Gln Glu Gln
            980                 985                 990

Ala Phe Val Thr Tyr His Met Arg Asp Ser Thr Phe Asn Ala Trp Thr
            995                 1000                1005

Gly Leu Asn Asp Ile Asn Ala Glu His Met Phe Leu Trp Thr Ala
            1010                1015                1020

Gly Gln Gly Val His Tyr Thr Asn Trp Gly Lys Gly Tyr Pro Gly
            1025                1030                1035

Gly Arg Arg Ser Ser Leu Ser Tyr Glu Asp Ala Asp Cys Val Val
            1040                1045                1050

Val Ile Gly Gly Asn Ser Arg Glu Ala Gly Thr Trp Met Asp Asp
            1055                1060                1065
```

-continued

Thr Cys Asp Ser Lys Gln Gly Tyr Ile Cys Gln Thr Gln Thr Asp
1070                1075                1080

Pro Ser Leu Pro Val Ser Pro Thr Thr Thr Pro Lys Asp Gly Phe
1085                1090                1095

Val Thr Tyr Gly Lys Ser Ser Tyr Ser Leu Met Lys Leu Lys Leu
1100                1105                1110

Pro Trp His Glu Ala Glu Thr Tyr Cys Lys Asp His Thr Ser Leu
1115                1120                1125

Leu Ala Ser Ile Leu Asp Pro Tyr Ser Asn Ala Phe Ala Trp Met
1130                1135                1140

Lys Met His Pro Phe Asn Val Pro Ile Trp Ile Ala Leu Asn Ser
1145                1150                1155

Asn Leu Thr Asn Asn Glu Tyr Thr Trp Thr Asp Arg Trp Arg Val
1160                1165                1170

Arg Tyr Thr Asn Trp Gly Ala Asp Glu Pro Lys Leu Lys Ser Ala
1175                1180                1185

Cys Val Tyr Met Asp Val Asp Gly Tyr Trp Arg Thr Ser Tyr Cys
1190                1195                1200

Asn Glu Ser Phe Tyr Phe Leu Cys Lys Lys Ser Asp Glu Ile Pro
1205                1210                1215

Ala Thr Glu Pro Pro Gln Leu Pro Gly Lys Cys Pro Glu Ser Glu
1220                1225                1230

Gln Thr Ala Trp Ile Pro Phe Tyr Gly His Cys Tyr Tyr Phe Glu
1235                1240                1245

Ser Ser Phe Thr Arg Ser Trp Gly Gln Ala Ser Leu Glu Cys Leu
1250                1255                1260

Arg Met Gly Ala Ser Leu Val Ser Ile Glu Thr Ala Ala Glu Ser
1265                1270                1275

Ser Phe Leu Ser Tyr Arg Val Glu Pro Leu Lys Ser Lys Thr Asn
1280                1285                1290

Phe Trp Ile Gly Met Phe Arg Asn Val Glu Gly Lys Trp Leu Trp
1295                1300                1305

Leu Asn Asp Asn Pro Val Ser Phe Val Asn Trp Lys Thr Gly Asp
1310                1315                1320

Pro Ser Gly Glu Arg Asn Asp Cys Val Val Leu Ala Ser Ser Ser
1325                1330                1335

Gly Leu Trp Asn Asn Ile His Cys Ser Ser Tyr Lys Gly Phe Ile
1340                1345                1350

Cys Lys Met Pro Lys Ile Ile Asp Pro Val Thr Thr His Ser Ser
1355                1360                1365

Ile Thr Thr Lys Ala Asp Gln Arg Lys Met Asp Pro Gln Pro Lys
1370                1375                1380

Gly Ser Ser Lys Ala Ala Gly Val Val Thr Val Val Leu Leu Ile
1385                1390                1395

Val Ile Gly Ala Gly Val Ala Ala Tyr Phe Phe Tyr Lys Lys Arg
1400                1405                1410

His Ala Leu His Ile Pro Gln Glu Ala Thr Phe Glu Asn Thr Leu
1415                1420                1425

Tyr Phe Asn Ser Asn Leu Ser Pro Gly Thr Ser Asp Thr Lys Asp
1430                1435                1440

Leu Met Gly Asn Ile Glu Gln Asn Glu His Ala Ile Ile
1445                1450                1455

<210> SEQ ID NO 4
<211> LENGTH: 1376
<212> TYPE: PRT
<213> ORGANISM: Mus musculus

<400> SEQUENCE: 4

Leu Leu Asp Ala Arg Gln Phe Leu Ile Tyr Asn Glu Asp His Lys Arg
1               5                   10                  15

Cys Val Asp Ala Leu Ser Ala Ile Ser Val Gln Thr Ala Thr Cys Asn
                20                  25                  30

Pro Glu Ala Glu Ser Gln Lys Phe Arg Trp Val Ser Asp Ser Gln Ile
            35                  40                  45

Met Ser Val Ala Phe Lys Leu Cys Leu Gly Val Pro Ser Lys Thr Asp
    50                  55                  60

Trp Ala Ser Val Thr Leu Tyr Ala Cys Asp Ser Lys Ser Glu Tyr Gln
65                  70                  75                  80

Lys Trp Glu Cys Lys Asn Asp Thr Leu Phe Gly Ile Lys Gly Thr Glu
                85                  90                  95

Leu Tyr Phe Asn Tyr Gly Asn Arg Gln Glu Lys Asn Ile Lys Leu Tyr
            100                 105                 110

Lys Gly Ser Gly Leu Trp Ser Arg Trp Lys Val Tyr Gly Thr Thr Asp
        115                 120                 125

Asp Leu Cys Ser Arg Gly Tyr Glu Ala Met Tyr Ser Leu Leu Gly Asn
    130                 135                 140

Ala Asn Gly Ala Val Cys Ala Phe Pro Phe Lys Phe Glu Asn Lys Trp
145                 150                 155                 160

Tyr Ala Asp Cys Thr Ser Ala Gly Arg Ser Asp Gly Trp Leu Trp Cys
                165                 170                 175

Gly Thr Thr Thr Asp Tyr Asp Lys Asp Lys Leu Phe Gly Phe Cys Pro
            180                 185                 190

Leu His Phe Glu Gly Ser Glu Arg Leu Trp Asn Lys Asp Pro Leu Thr
        195                 200                 205

Gly Ile Leu Tyr Gln Ile Asn Ser Lys Ser Ala Leu Thr Trp His Gln
    210                 215                 220

Ala Arg Ala Ser Cys Lys Gln Gln Asn Ala Asp Leu Leu Ser Val Thr
225                 230                 235                 240

Glu Ile His Glu Gln Met Tyr Leu Thr Gly Leu Thr Ser Ser Leu Ser
                245                 250                 255

Ser Gly Leu Trp Ile Gly Leu Asn Ser Leu Ser Val Arg Ser Gly Trp
            260                 265                 270

Gln Trp Ala Gly Gly Ser Pro Phe Arg Tyr Leu Asn Trp Leu Pro Gly
        275                 280                 285

Ser Pro Ser Ser Glu Pro Gly Lys Ser Cys Val Ser Leu Asn Pro Gly
    290                 295                 300

Lys Asn Ala Lys Trp Glu Asn Leu Glu Cys Val Gln Lys Leu Gly Tyr
305                 310                 315                 320

Ile Cys Lys Lys Gly Asn Asn Thr Leu Asn Pro Phe Ile Ile Pro Ser
                325                 330                 335

Ala Ser Asp Val Pro Thr Gly Cys Pro Asn Gln Trp Trp Pro Tyr Ala
            340                 345                 350

Gly His Cys Tyr Arg Ile His Arg Glu Glu Lys Ile Gln Lys Tyr
        355                 360                 365

Ala Leu Gln Ala Cys Arg Lys Glu Gly Gly Asp Leu Ala Ser Ile His
    370                 375                 380

```
Ser Ile Glu Glu Phe Asp Phe Ile Phe Ser Gln Leu Gly Tyr Glu Pro
385                 390                 395                 400

Asn Asp Glu Leu Trp Ile Gly Leu Asn Asp Ile Lys Ile Gln Met Tyr
            405                 410                 415

Phe Glu Trp Ser Asp Gly Thr Pro Val Thr Phe Thr Lys Trp Leu Pro
        420                 425                 430

Gly Glu Pro Ser His Glu Asn Asn Arg Gln Glu Asp Cys Val Val Met
    435                 440                 445

Lys Gly Lys Asp Gly Tyr Trp Ala Asp Arg Ala Cys Glu Gln Pro Leu
450                 455                 460

Gly Tyr Ile Cys Lys Met Val Ser Gln Ser His Ala Val Val Pro Glu
465                 470                 475                 480

Gly Ala Asp Lys Gly Cys Arg Lys Gly Trp Lys Arg His Gly Phe Tyr
                485                 490                 495

Cys Tyr Leu Ile Gly Ser Thr Leu Ser Thr Phe Thr Asp Ala Asn His
            500                 505                 510

Thr Cys Thr Asn Glu Lys Ala Tyr Leu Thr Thr Val Glu Asp Arg Tyr
        515                 520                 525

Glu Gln Ala Phe Leu Thr Ser Leu Val Gly Leu Arg Pro Glu Lys Tyr
    530                 535                 540

Phe Trp Thr Gly Leu Ser Asp Val Gln Asn Lys Gly Thr Phe Arg Trp
545                 550                 555                 560

Thr Val Asp Glu Gln Val Gln Phe Thr His Trp Asn Ala Asp Met Pro
                565                 570                 575

Gly Arg Lys Ala Gly Cys Val Ala Met Lys Thr Gly Val Ala Gly Gly
            580                 585                 590

Leu Trp Asp Val Leu Ser Cys Glu Glu Lys Ala Lys Phe Val Cys Lys
        595                 600                 605

His Trp Ala Glu Gly Val Thr Arg Pro Pro Glu Pro Thr Thr Thr Pro
    610                 615                 620

Glu Pro Lys Cys Pro Glu Asn Trp Gly Thr Thr Ser Lys Thr Ser Met
625                 630                 635                 640

Cys Phe Lys Leu Tyr Ala Lys Gly Lys His Glu Lys Lys Thr Trp Phe
                645                 650                 655

Glu Ser Arg Asp Phe Cys Lys Ala Ile Gly Gly Glu Leu Ala Ser Ile
            660                 665                 670

Lys Ser Lys Asp Glu Gln Gln Val Ile Trp Arg Leu Ile Thr Ser Ser
        675                 680                 685

Gly Ser Tyr His Glu Leu Phe Trp Leu Gly Leu Thr Tyr Gly Ser Pro
    690                 695                 700

Ser Glu Gly Phe Thr Trp Ser Asp Gly Ser Pro Val Ser Tyr Glu Asn
705                 710                 715                 720

Trp Ala Tyr Gly Glu Pro Asn Asn Tyr Gln Asn Val Glu Tyr Cys Gly
                725                 730                 735

Glu Leu Lys Gly Asp Pro Gly Met Ser Trp Asn Asp Ile Asn Cys Glu
            740                 745                 750

His Leu Asn Asn Trp Ile Cys Gln Ile Gln Lys Gly Lys Thr Leu Leu
        755                 760                 765

Pro Glu Pro Thr Pro Ala Pro Gln Asp Asn Pro Pro Val Thr Ala Asp
    770                 775                 780

Gly Trp Val Ile Tyr Lys Asp Tyr Gln Tyr Tyr Phe Ser Lys Glu Lys
785                 790                 795                 800
```

-continued

```
Glu Thr Met Asp Asn Ala Arg Ala Phe Cys Lys Lys Asn Phe Gly Asp
                805                 810                 815

Leu Ala Thr Ile Lys Ser Glu Ser Glu Lys Lys Phe Leu Trp Lys Tyr
            820                 825                 830

Ile Asn Lys Asn Gly Gly Gln Ser Pro Tyr Phe Ile Gly Met Leu Ile
            835                 840                 845

Ser Met Asp Lys Lys Phe Ile Trp Met Asp Gly Ser Lys Val Asp Phe
850                 855                 860

Val Ala Trp Ala Thr Gly Glu Pro Asn Phe Ala Asn Asp Asp Glu Asn
865                 870                 875                 880

Cys Val Thr Met Tyr Thr Asn Ser Gly Phe Trp Asn Asp Ile Asn Cys
                885                 890                 895

Gly Tyr Pro Asn Asn Phe Ile Cys Gln Arg His Asn Ser Ser Ile Asn
                900                 905                 910

Ala Thr Ala Met Pro Thr Thr Pro Thr Thr Pro Gly Gly Cys Lys Glu
            915                 920                 925

Gly Trp His Leu Tyr Lys Asn Lys Cys Phe Lys Ile Phe Gly Phe Ala
            930                 935                 940

Asn Glu Glu Lys Lys Ser Trp Gln Asp Ala Arg Gln Ala Cys Lys Gly
945                 950                 955                 960

Leu Lys Gly Asn Leu Val Ser Ile Glu Asn Ala Gln Glu Gln Ala Phe
                965                 970                 975

Val Thr Tyr His Met Arg Asp Ser Thr Phe Asn Ala Trp Thr Gly Leu
                980                 985                 990

Asn Asp Ile Asn Ala Glu His Met  Phe Leu Trp Thr Ala Gly Gln Gly
                995                 1000                1005

Val His  Tyr Thr Asn Trp Gly  Lys Gly Tyr Pro Gly  Gly Arg Arg
    1010                1015                1020

Ser Ser  Leu Ser Tyr Glu Asp  Ala Asp Cys Val Val  Val Ile Gly
    1025                1030                1035

Gly Asn  Ser Arg Glu Ala Gly  Thr Trp Met Asp Asp  Thr Cys Asp
    1040                1045                1050

Ser Lys  Gln Gly Tyr Ile Cys  Gln Thr Gln Thr Asp  Pro Ser Leu
    1055                1060                1065

Pro Val  Ser Pro Thr Thr Thr  Pro Lys Asp Gly Phe  Val Thr Tyr
    1070                1075                1080

Gly Lys  Ser Ser Tyr Ser Leu  Met Lys Leu Lys Leu  Pro Trp His
    1085                1090                1095

Glu Ala  Glu Thr Tyr Cys Lys  Asp His Thr Ser Leu  Leu Ala Ser
    1100                1105                1110

Ile Leu  Asp Pro Tyr Ser Asn  Ala Phe Ala Trp Met  Lys Met His
    1115                1120                1125

Pro Phe  Asn Val Pro Ile Trp  Ile Ala Leu Asn Ser  Asn Leu Thr
    1130                1135                1140

Asn Asn  Glu Tyr Thr Trp Thr  Asp Arg Trp Arg Val  Arg Tyr Thr
    1145                1150                1155

Asn Trp  Gly Ala Asp Glu Pro  Lys Leu Lys Ser Ala  Cys Val Tyr
    1160                1165                1170

Met Asp  Val Asp Gly Tyr Trp  Arg Thr Ser Tyr Cys  Asn Glu Ser
    1175                1180                1185

Phe Tyr  Phe Leu Cys Lys Lys  Ser Asp Glu Ile Pro  Ala Thr Glu
    1190                1195                1200

Pro Pro  Gln Leu Pro Gly Lys  Cys Pro Glu Ser Glu  Gln Thr Ala
```

```
            1205                1210                1215
Trp Ile Pro Phe Tyr Gly His Cys Tyr Tyr Phe Glu Ser Ser Phe
    1220                1225                1230

Thr Arg Ser Trp Gly Gln Ala Ser Leu Glu Cys Leu Arg Met Gly
    1235                1240                1245

Ala Ser Leu Val Ser Ile Glu Thr Ala Ala Glu Ser Ser Phe Leu
    1250                1255                1260

Ser Tyr Arg Val Glu Pro Leu Lys Ser Lys Thr Asn Phe Trp Ile
    1265                1270                1275

Gly Met Phe Arg Asn Val Glu Gly Lys Trp Leu Trp Leu Asn Asp
    1280                1285                1290

Asn Pro Val Ser Phe Val Asn Trp Lys Thr Gly Asp Pro Ser Gly
    1295                1300                1305

Glu Arg Asn Asp Cys Val Val Leu Ala Ser Ser Ser Gly Leu Trp
    1310                1315                1320

Asn Asn Ile His Cys Ser Ser Tyr Lys Gly Phe Ile Cys Lys Met
    1325                1330                1335

Pro Lys Ile Ile Asp Pro Val Thr Thr His Ser Ser Ile Thr Thr
    1340                1345                1350

Lys Ala Asp Gln Arg Lys Met Asp Pro Gln Pro Lys Gly Ser Ser
    1355                1360                1365

Lys Ala His His His His His His
    1370                1375

<210> SEQ ID NO 5
<211> LENGTH: 1365
<212> TYPE: PRT
<213> ORGANISM: Homo sapiens

<400> SEQUENCE: 5

Leu Leu Asp Thr Arg Gln Phe Leu Ile Tyr Asn Glu Asp His Lys Arg
1               5                   10                  15

Cys Val Asp Ala Val Ser Pro Ser Ala Val Gln Thr Ala Ala Cys Asn
                20                  25                  30

Gln Asp Ala Glu Ser Gln Lys Phe Arg Trp Val Ser Glu Ser Gln Ile
            35                  40                  45

Met Ser Val Ala Phe Lys Leu Cys Leu Gly Val Pro Ser Lys Thr Asp
        50                  55                  60

Trp Val Ala Ile Thr Leu Tyr Ala Cys Asp Ser Lys Ser Glu Phe Gln
65                  70                  75                  80

Lys Trp Glu Cys Lys Asn Asp Thr Leu Leu Gly Ile Lys Gly Glu Asp
                85                  90                  95

Leu Phe Phe Asn Tyr Gly Asn Arg Gln Glu Lys Asn Ile Met Leu Tyr
                100                 105                 110

Lys Gly Ser Gly Leu Trp Ser Arg Trp Lys Ile Tyr Gly Thr Thr Asp
            115                 120                 125

Asn Leu Cys Ser Arg Gly Tyr Glu Ala Met Tyr Thr Leu Leu Gly Asn
        130                 135                 140

Ala Asn Gly Ala Thr Cys Ala Phe Pro Phe Lys Phe Glu Asn Lys Trp
145                 150                 155                 160

Tyr Ala Asp Cys Thr Ser Ala Gly Arg Ser Asp Gly Trp Leu Trp Cys
                165                 170                 175

Gly Thr Thr Thr Asp Tyr Asp Thr Asp Lys Leu Phe Gly Tyr Cys Pro
                180                 185                 190
```

-continued

Leu Lys Phe Glu Gly Ser Glu Ser Leu Trp Asn Lys Asp Pro Leu Thr
            195                 200                 205

Ser Val Ser Tyr Gln Ile Asn Ser Lys Ser Ala Leu Thr Trp His Gln
    210                 215                 220

Ala Arg Lys Ser Cys Gln Gln Asn Ala Glu Leu Leu Ser Ile Thr
225                 230                 235                 240

Glu Ile His Glu Gln Thr Tyr Leu Thr Gly Leu Thr Ser Ser Leu Thr
                245                 250                 255

Ser Gly Leu Trp Ile Gly Leu Asn Ser Leu Ser Phe Asn Ser Gly Trp
            260                 265                 270

Gln Trp Ser Asp Arg Ser Pro Phe Arg Tyr Leu Asn Trp Leu Pro Gly
        275                 280                 285

Ser Pro Ser Ala Glu Pro Gly Lys Ser Cys Val Ser Leu Asn Pro Gly
    290                 295                 300

Lys Asn Ala Lys Trp Glu Asn Leu Glu Cys Val Gln Lys Leu Gly Tyr
305                 310                 315                 320

Ile Cys Lys Lys Gly Asn Thr Thr Leu Asn Ser Phe Val Ile Pro Ser
                325                 330                 335

Glu Ser Asp Val Pro Thr His Cys Pro Ser Gln Trp Trp Pro Tyr Ala
            340                 345                 350

Gly His Cys Tyr Lys Ile His Arg Asp Glu Lys Lys Ile Gln Arg Asp
        355                 360                 365

Ala Leu Thr Thr Cys Arg Lys Glu Gly Gly Asp Leu Thr Ser Ile His
    370                 375                 380

Thr Ile Glu Glu Leu Asp Phe Ile Ile Ser Gln Leu Gly Tyr Glu Pro
385                 390                 395                 400

Asn Asp Glu Leu Trp Ile Gly Leu Asn Asp Ile Lys Ile Gln Met Tyr
                405                 410                 415

Phe Glu Trp Ser Asp Gly Thr Pro Val Thr Phe Thr Lys Trp Leu Arg
            420                 425                 430

Gly Glu Pro Ser His Glu Asn Asn Arg Gln Glu Asp Cys Val Val Met
        435                 440                 445

Lys Gly Lys Asp Gly Tyr Trp Ala Asp Arg Gly Cys Glu Trp Pro Leu
    450                 455                 460

Gly Tyr Ile Cys Lys Met Lys Ser Arg Ser Gln Gly Pro Glu Ile Val
465                 470                 475                 480

Glu Val Glu Lys Gly Cys Arg Lys Gly Trp Lys Lys His His Phe Tyr
                485                 490                 495

Cys Tyr Met Ile Gly His Thr Leu Ser Thr Phe Ala Glu Ala Asn Gln
            500                 505                 510

Thr Cys Asn Asn Glu Asn Ala Tyr Leu Thr Thr Ile Glu Asp Arg Tyr
        515                 520                 525

Glu Gln Ala Phe Leu Thr Ser Phe Val Gly Leu Arg Pro Glu Lys Tyr
    530                 535                 540

Phe Trp Thr Gly Leu Ser Asp Ile Gln Thr Lys Gly Thr Phe Gln Trp
545                 550                 555                 560

Thr Ile Glu Glu Glu Val Arg Phe Thr His Trp Asn Ser Asp Met Pro
                565                 570                 575

Gly Arg Lys Pro Gly Cys Val Ala Met Arg Thr Gly Ile Ala Gly Gly
            580                 585                 590

Leu Trp Asp Val Leu Lys Cys Asp Glu Lys Ala Lys Phe Val Cys Lys
        595                 600                 605

His Trp Ala Glu Gly Val Thr His Pro Pro Lys Pro Thr Thr Thr Pro

```
                610                615                620
Glu Pro Lys Cys Pro Glu Asp Trp Gly Ala Ser Ser Arg Thr Ser Leu
625                630                635                640

Cys Phe Lys Leu Tyr Ala Lys Gly Lys His Glu Lys Lys Thr Trp Phe
                645                650                655

Glu Ser Arg Asp Phe Cys Arg Ala Leu Gly Gly Asp Leu Ala Ser Ile
                660                665                670

Asn Asn Lys Glu Glu Gln Gln Thr Ile Trp Arg Leu Ile Thr Ala Ser
                675                680                685

Gly Ser Tyr His Lys Leu Phe Trp Leu Gly Leu Thr Tyr Gly Ser Pro
                690                695                700

Ser Glu Gly Phe Thr Trp Ser Asp Gly Ser Pro Val Ser Tyr Glu Asn
705                710                715                720

Trp Ala Tyr Gly Glu Pro Asn Asn Tyr Gln Asn Val Glu Tyr Cys Gly
                725                730                735

Glu Leu Lys Gly Asp Pro Thr Met Ser Trp Asn Asp Ile Asn Cys Glu
                740                745                750

His Leu Asn Asn Trp Ile Cys Gln Ile Gln Lys Gly Gln Thr Pro Lys
                755                760                765

Pro Glu Pro Thr Pro Ala Pro Gln Asp Asn Pro Pro Val Thr Glu Asp
                770                775                780

Gly Trp Val Ile Tyr Lys Asp Tyr Gln Tyr Tyr Phe Ser Lys Glu Lys
785                790                795                800

Glu Thr Met Asp Asn Ala Arg Ala Phe Cys Lys Arg Asn Phe Gly Asp
                805                810                815

Leu Val Ser Ile Gln Ser Glu Ser Glu Lys Lys Phe Leu Trp Lys Tyr
                820                825                830

Val Asn Arg Asn Asp Ala Gln Ser Ala Tyr Phe Ile Gly Leu Leu Ile
                835                840                845

Ser Leu Asp Lys Lys Phe Ala Trp Met Asp Gly Ser Lys Val Asp Tyr
                850                855                860

Val Ser Trp Ala Thr Gly Glu Pro Asn Phe Ala Asn Glu Asp Glu Asn
865                870                875                880

Cys Val Thr Met Tyr Ser Asn Ser Gly Phe Trp Asn Asp Ile Asn Cys
                885                890                895

Gly Tyr Pro Asn Ala Phe Ile Cys Gln Arg His Asn Ser Ser Ile Asn
                900                905                910

Ala Thr Thr Val Met Pro Thr Met Pro Ser Val Pro Ser Gly Cys Lys
                915                920                925

Glu Gly Trp Asn Phe Tyr Ser Asn Lys Cys Phe Lys Ile Phe Gly Phe
930                935                940

Met Glu Glu Glu Arg Lys Asn Trp Gln Glu Ala Arg Lys Ala Cys Ile
945                950                955                960

Gly Phe Gly Gly Asn Leu Val Ser Ile Gln Asn Glu Lys Glu Gln Ala
                965                970                975

Phe Leu Thr Tyr His Met Lys Asp Ser Thr Phe Ser Ala Trp Thr Gly
                980                985                990

Leu Asn Asp Val Asn Ser Glu His Thr Phe Leu Trp Thr Asp Gly Arg
                995                1000               1005

Gly Val His Tyr Thr Asn Trp Gly Lys Gly Tyr Pro Gly Gly Arg
                1010               1015               1020

Arg Ser Ser Leu Ser Tyr Glu Asp Ala Asp Cys Val Val Ile Ile
                1025               1030               1035
```

```
Gly Gly Ala Ser Asn Glu Ala Gly Lys Trp Met Asp Asp Thr Cys
        1040                1045                1050

Asp Ser Lys Arg Gly Tyr Ile Cys Gln Thr Arg Ser Asp Pro Ser
        1055                1060                1065

Leu Thr Asn Pro Pro Ala Thr Ile Gln Thr Asp Gly Phe Val Lys
        1070                1075                1080

Tyr Gly Lys Ser Ser Tyr Ser Leu Met Arg Gln Lys Phe Gln Trp
        1085                1090                1095

His Glu Ala Glu Thr Tyr Cys Lys Leu His Asn Ser Leu Ile Ala
        1100                1105                1110

Ser Ile Leu Asp Pro Tyr Ser Asn Ala Phe Ala Trp Leu Gln Met
        1115                1120                1125

Glu Thr Ser Asn Glu Arg Val Trp Ile Ala Leu Asn Ser Asn Leu
        1130                1135                1140

Thr Asp Asn Gln Tyr Thr Trp Thr Asp Lys Trp Arg Val Arg Tyr
        1145                1150                1155

Thr Asn Trp Ala Ala Asp Glu Pro Lys Leu Lys Ser Ala Cys Val
        1160                1165                1170

Tyr Leu Asp Leu Asp Gly Tyr Trp Lys Thr Ala His Cys Asn Glu
        1175                1180                1185

Ser Phe Tyr Phe Leu Cys Lys Arg Ser Asp Glu Ile Pro Ala Thr
        1190                1195                1200

Glu Pro Pro Gln Leu Pro Gly Arg Cys Pro Glu Ser Asp His Thr
        1205                1210                1215

Ala Trp Ile Pro Phe His Gly His Cys Tyr Tyr Ile Glu Ser Ser
        1220                1225                1230

Tyr Thr Arg Asn Trp Gly Gln Ala Ser Leu Glu Cys Leu Arg Met
        1235                1240                1245

Gly Ser Ser Leu Val Ser Ile Glu Ser Ala Ala Glu Ser Ser Phe
        1250                1255                1260

Leu Ser Tyr Arg Val Glu Pro Leu Lys Ser Lys Thr Asn Phe Trp
        1265                1270                1275

Ile Gly Leu Phe Arg Asn Val Glu Gly Thr Trp Leu Trp Ile Asn
        1280                1285                1290

Asn Ser Pro Val Ser Phe Val Asn Trp Asn Thr Gly Asp Pro Ser
        1295                1300                1305

Gly Glu Arg Asn Asp Cys Val Ala Leu His Ala Ser Ser Gly Phe
        1310                1315                1320

Trp Ser Asn Ile His Cys Ser Ser Tyr Lys Gly Tyr Ile Cys Lys
        1325                1330                1335

Arg Pro Lys Ile Ile Asp Ala Lys Pro Thr His Glu Leu Leu Thr
        1340                1345                1350

Thr Lys Ala Asp Thr Arg Lys Met Asp Pro Ser Lys
        1355                1360                1365

<210> SEQ ID NO 6
<211> LENGTH: 1370
<212> TYPE: PRT
<213> ORGANISM: Mus musculus

<400> SEQUENCE: 6

Leu Leu Asp Ala Arg Gln Phe Leu Ile Tyr Asn Glu Asp His Lys Arg
1               5                   10                  15

Cys Val Asp Ala Leu Ser Ala Ile Ser Val Gln Thr Ala Thr Cys Asn
```

-continued

```
                20                  25                  30
Pro Glu Ala Glu Ser Gln Lys Phe Arg Trp Val Ser Asp Ser Gln Ile
            35                  40                  45
Met Ser Val Ala Phe Lys Leu Cys Leu Gly Val Pro Ser Lys Thr Asp
         50                  55                  60
Trp Ala Ser Val Thr Leu Tyr Ala Cys Asp Ser Lys Ser Glu Tyr Gln
 65                  70                  75                  80
Lys Trp Glu Cys Lys Asn Asp Thr Leu Phe Gly Ile Lys Gly Thr Glu
                 85                  90                  95
Leu Tyr Phe Asn Tyr Gly Asn Arg Gln Glu Lys Asn Ile Lys Leu Tyr
            100                 105                 110
Lys Gly Ser Gly Leu Trp Ser Arg Trp Lys Val Tyr Gly Thr Thr Asp
         115                 120                 125
Asp Leu Cys Ser Arg Gly Tyr Glu Ala Met Tyr Ser Leu Leu Gly Asn
            130                 135                 140
Ala Asn Gly Ala Val Cys Ala Phe Pro Phe Lys Phe Glu Asn Lys Trp
145                 150                 155                 160
Tyr Ala Asp Cys Thr Ser Ala Gly Arg Ser Asp Gly Trp Leu Trp Cys
                165                 170                 175
Gly Thr Thr Thr Asp Tyr Asp Lys Asp Lys Leu Phe Gly Phe Cys Pro
            180                 185                 190
Leu His Phe Glu Gly Ser Glu Arg Leu Trp Asn Lys Asp Pro Leu Thr
         195                 200                 205
Gly Ile Leu Tyr Gln Ile Asn Ser Lys Ser Ala Leu Thr Trp His Gln
         210                 215                 220
Ala Arg Ala Ser Cys Lys Gln Gln Asn Ala Asp Leu Leu Ser Val Thr
225                 230                 235                 240
Glu Ile His Glu Gln Met Tyr Leu Thr Gly Leu Thr Ser Ser Leu Ser
                245                 250                 255
Ser Gly Leu Trp Ile Gly Leu Asn Ser Leu Ser Val Arg Ser Gly Trp
            260                 265                 270
Gln Trp Ala Gly Gly Ser Pro Phe Arg Tyr Leu Asn Trp Leu Pro Gly
         275                 280                 285
Ser Pro Ser Ser Glu Pro Gly Lys Ser Cys Val Ser Leu Asn Pro Gly
         290                 295                 300
Lys Asn Ala Lys Trp Glu Asn Leu Glu Cys Val Gln Lys Leu Gly Tyr
305                 310                 315                 320
Ile Cys Lys Lys Gly Asn Asn Thr Leu Asn Pro Phe Ile Ile Pro Ser
                325                 330                 335
Ala Ser Asp Val Pro Thr Gly Cys Pro Asn Gln Trp Trp Pro Tyr Ala
            340                 345                 350
Gly His Cys Tyr Arg Ile His Arg Glu Glu Lys Lys Ile Gln Lys Tyr
         355                 360                 365
Ala Leu Gln Ala Cys Arg Lys Glu Gly Gly Asp Leu Ala Ser Ile His
         370                 375                 380
Ser Ile Glu Glu Phe Asp Phe Ile Phe Ser Gln Leu Gly Tyr Glu Pro
385                 390                 395                 400
Asn Asp Glu Leu Trp Ile Gly Leu Asn Asp Ile Lys Ile Gln Met Tyr
                405                 410                 415
Phe Glu Trp Ser Asp Gly Thr Pro Val Thr Phe Thr Lys Trp Leu Pro
            420                 425                 430
Gly Glu Pro Ser His Glu Asn Asn Arg Gln Glu Asp Cys Val Val Met
         435                 440                 445
```

-continued

```
Lys Gly Lys Asp Gly Tyr Trp Ala Asp Arg Ala Cys Glu Gln Pro Leu
    450                 455                 460
Gly Tyr Ile Cys Lys Met Val Ser Gln Ser His Ala Val Val Pro Glu
465                 470                 475                 480
Gly Ala Asp Lys Gly Cys Arg Lys Gly Trp Lys Arg His Gly Phe Tyr
                485                 490                 495
Cys Tyr Leu Ile Gly Ser Thr Leu Ser Thr Phe Thr Asp Ala Asn His
            500                 505                 510
Thr Cys Thr Asn Glu Lys Ala Tyr Leu Thr Thr Val Glu Asp Arg Tyr
        515                 520                 525
Glu Gln Ala Phe Leu Thr Ser Leu Val Gly Leu Arg Pro Glu Lys Tyr
    530                 535                 540
Phe Trp Thr Gly Leu Ser Asp Val Gln Asn Lys Gly Thr Phe Arg Trp
545                 550                 555                 560
Thr Val Asp Glu Gln Val Gln Phe Thr His Trp Asn Ala Asp Met Pro
                565                 570                 575
Gly Arg Lys Ala Gly Cys Val Ala Met Lys Thr Gly Val Ala Gly Gly
            580                 585                 590
Leu Trp Asp Val Leu Ser Cys Glu Glu Lys Ala Lys Phe Val Cys Lys
        595                 600                 605
His Trp Ala Glu Gly Val Thr Arg Pro Pro Glu Pro Thr Thr Thr Pro
    610                 615                 620
Glu Pro Lys Cys Pro Glu Asn Trp Gly Thr Thr Ser Lys Thr Ser Met
625                 630                 635                 640
Cys Phe Lys Leu Tyr Ala Lys Gly Lys His Glu Lys Lys Thr Trp Phe
                645                 650                 655
Glu Ser Arg Asp Phe Cys Lys Ala Ile Gly Gly Glu Leu Ala Ser Ile
            660                 665                 670
Lys Ser Lys Asp Glu Gln Gln Val Ile Trp Arg Leu Ile Thr Ser Ser
        675                 680                 685
Gly Ser Tyr His Glu Leu Phe Trp Leu Gly Leu Thr Tyr Gly Ser Pro
    690                 695                 700
Ser Glu Gly Phe Thr Trp Ser Asp Gly Ser Pro Val Ser Tyr Glu Asn
705                 710                 715                 720
Trp Ala Tyr Gly Glu Pro Asn Asn Tyr Gln Asn Val Glu Tyr Cys Gly
                725                 730                 735
Glu Leu Lys Gly Asp Pro Gly Met Ser Trp Asn Asp Ile Asn Cys Glu
            740                 745                 750
His Leu Asn Asn Trp Ile Cys Gln Ile Gln Lys Gly Lys Thr Leu Leu
        755                 760                 765
Pro Glu Pro Thr Pro Ala Pro Gln Asp Asn Pro Pro Val Thr Ala Asp
    770                 775                 780
Gly Trp Val Ile Tyr Lys Asp Tyr Gln Tyr Tyr Phe Ser Lys Glu Lys
785                 790                 795                 800
Glu Thr Met Asp Asn Ala Arg Ala Phe Cys Lys Lys Asn Phe Gly Asp
                805                 810                 815
Leu Ala Thr Ile Lys Ser Glu Ser Glu Lys Lys Phe Leu Trp Lys Tyr
            820                 825                 830
Ile Asn Lys Asn Gly Gly Gln Ser Pro Tyr Phe Ile Gly Met Leu Ile
        835                 840                 845
Ser Met Asp Lys Lys Phe Ile Trp Met Asp Gly Ser Lys Val Asp Phe
    850                 855                 860
```

-continued

```
Val Ala Trp Ala Thr Gly Glu Pro Asn Phe Ala Asn Asp Asp Glu Asn
865                 870                 875                 880

Cys Val Thr Met Tyr Thr Asn Ser Gly Phe Trp Asn Asp Ile Asn Cys
                885                 890                 895

Gly Tyr Pro Asn Asn Phe Ile Cys Gln Arg His Asn Ser Ser Ile Asn
            900                 905                 910

Ala Thr Ala Met Pro Thr Thr Pro Thr Thr Pro Gly Gly Cys Lys Glu
            915                 920                 925

Gly Trp His Leu Tyr Lys Asn Lys Cys Phe Lys Ile Phe Gly Phe Ala
        930                 935                 940

Asn Glu Glu Lys Lys Ser Trp Gln Asp Ala Arg Gln Ala Cys Lys Gly
945                 950                 955                 960

Leu Lys Gly Asn Leu Val Ser Ile Glu Asn Ala Gln Glu Gln Ala Phe
                965                 970                 975

Val Thr Tyr His Met Arg Asp Ser Thr Phe Asn Ala Trp Thr Gly Leu
            980                 985                 990

Asn Asp Ile Asn Ala Glu His Met Phe Leu Trp Thr Ala Gly Gln Gly
            995                 1000                1005

Val His Tyr Thr Asn Trp Gly Lys Gly Tyr Pro Gly Gly Arg Arg
        1010                1015                1020

Ser Ser Leu Ser Tyr Glu Asp Ala Asp Cys Val Val Val Ile Gly
    1025                1030                1035

Gly Asn Ser Arg Glu Ala Gly Thr Trp Met Asp Asp Thr Cys Asp
    1040                1045                1050

Ser Lys Gln Gly Tyr Ile Cys Gln Thr Gln Thr Asp Pro Ser Leu
    1055                1060                1065

Pro Val Ser Pro Thr Thr Thr Pro Lys Asp Gly Phe Val Thr Tyr
    1070                1075                1080

Gly Lys Ser Ser Tyr Ser Leu Met Lys Leu Lys Leu Pro Trp His
    1085                1090                1095

Glu Ala Glu Thr Tyr Cys Lys Asp His Thr Ser Leu Leu Ala Ser
    1100                1105                1110

Ile Leu Asp Pro Tyr Ser Asn Ala Phe Ala Trp Met Lys Met His
    1115                1120                1125

Pro Phe Asn Val Pro Ile Trp Ile Ala Leu Asn Ser Asn Leu Thr
    1130                1135                1140

Asn Asn Glu Tyr Thr Trp Thr Asp Arg Trp Arg Val Arg Tyr Thr
    1145                1150                1155

Asn Trp Gly Ala Asp Glu Pro Lys Leu Lys Ser Ala Cys Val Tyr
    1160                1165                1170

Met Asp Val Asp Gly Tyr Trp Arg Thr Ser Tyr Cys Asn Glu Ser
    1175                1180                1185

Phe Tyr Phe Leu Cys Lys Lys Ser Asp Glu Ile Pro Ala Thr Glu
    1190                1195                1200

Pro Pro Gln Leu Pro Gly Lys Cys Pro Glu Ser Glu Gln Thr Ala
    1205                1210                1215

Trp Ile Pro Phe Tyr Gly His Cys Tyr Tyr Phe Glu Ser Ser Phe
    1220                1225                1230

Thr Arg Ser Trp Gly Gln Ala Ser Leu Glu Cys Leu Arg Met Gly
    1235                1240                1245

Ala Ser Leu Val Ser Ile Glu Thr Ala Ala Glu Ser Ser Phe Leu
    1250                1255                1260

Ser Tyr Arg Val Glu Pro Leu Lys Ser Lys Thr Asn Phe Trp Ile
```

```
                    1265                1270                1275
Gly Met Phe Arg Asn Val Glu Gly Lys Trp Leu Trp Leu Asn Asp
            1280                1285                1290

Asn Pro Val Ser Phe Val Asn Trp Lys Thr Gly Asp Pro Ser Gly
        1295                1300                1305

Glu Arg Asn Asp Cys Val Val Leu Ala Ser Ser Gly Leu Trp
    1310                1315                1320

Asn Asn Ile His Cys Ser Ser Tyr Lys Gly Phe Ile Cys Lys Met
    1325                1330                1335

Pro Lys Ile Ile Asp Pro Val Thr Thr His Ser Ser Ile Thr Thr
    1340                1345                1350

Lys Ala Asp Gln Arg Lys Met Asp Pro Gln Pro Lys Gly Ser Ser
    1355                1360                1365

Lys Ala
    1370

<210> SEQ ID NO 7
<211> LENGTH: 118
<212> TYPE: PRT
<213> ORGANISM: Vicugna pacos

<400> SEQUENCE: 7

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Asp Tyr Tyr
            20                  25                  30

Ala Ile Gly Trp Phe Arg Gln Ala Pro Gly Lys Glu Arg Glu Gly Ile
        35                  40                  45

Ser Cys Ile Ser Tyr Lys Gly Gly Ser Thr Thr Tyr Ala Asp Ser Val
    50                  55                  60

Lys Gly Arg Phe Thr Ile Ser Lys Asp Asn Ala Lys Asn Thr Ala Tyr
65                  70                  75                  80

Leu Gln Met Asn Ser Leu Lys Pro Glu Asp Thr Gly Ile Tyr Ser Cys
                85                  90                  95

Ala Ala Gly Phe Val Cys Tyr Asn Tyr Asp Tyr Trp Gly Gln Gly Thr
            100                 105                 110

Gln Val Thr Val Ser Ser
        115

<210> SEQ ID NO 8
<211> LENGTH: 118
<212> TYPE: PRT
<213> ORGANISM: Vicugna pacos

<400> SEQUENCE: 8

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Ile
        35                  40                  45

Ser Cys Ile Ser Tyr Lys Gly Ser Thr Thr Tyr Ala Asp Ser Val
    50                  55                  60

Lys Gly Arg Phe Thr Ile Ser Lys Asp Asn Ala Lys Asn Thr Ala Tyr
65                  70                  75                  80

Leu Gln Met Asn Asn Leu Lys Pro Glu Asp Thr Gly Ile Tyr Tyr Cys
```

85                  90                  95
Ala Ala Gly Phe Val Cys Tyr Asn Tyr Asp Tyr Trp Gly Pro Gly Thr
                100                 105                 110

Gln Val Thr Val Ser Ser
        115

<210> SEQ ID NO 9
<211> LENGTH: 122
<212> TYPE: PRT
<213> ORGANISM: Vicugna pacos

<400> SEQUENCE: 9

Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Thr Phe Ser Ile Asn
            20                  25                  30

Tyr Met Gly Trp Tyr Arg Gln Ala Pro Gly Lys Gln Arg Glu Leu Val
        35                  40                  45

Ala Ala Ile Thr Ser Gly Ser Gly Ser Thr Asn Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Asn Ala Asp Met Asp Ser Ser Leu Ser Gly Tyr Val Asp Val Trp
                100                 105                 110

Gly Gln Gly Thr Gln Val Thr Val Ser Ser
        115                 120

<210> SEQ ID NO 10
<211> LENGTH: 131
<212> TYPE: PRT
<213> ORGANISM: Vicugna pacos

<400> SEQUENCE: 10

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Asp Asp Asp Tyr
            20                  25                  30

Asp Ile Gly Trp Phe Arg Gln Ala Pro Gly Lys Glu Arg Glu Gly Val
        35                  40                  45

Ser Cys Ile Ser Ser Ser Asp Gly Ser Thr Tyr Ala Asp Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Phe Phe Arg Trp Ser Gly Ser Tyr Tyr Val Arg Gly
                100                 105                 110

Cys Arg His Ala Thr Tyr Asp Tyr Trp Gly Gln Gly Thr Gln Val Thr
        115                 120                 125

Val Ser Ser
    130

<210> SEQ ID NO 11
<211> LENGTH: 133
<212> TYPE: PRT

<213> ORGANISM: Vicugna pacos

<400> SEQUENCE: 11

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Asn Tyr
            20                  25                  30

Thr Val Ala Trp Phe Arg Gln Ala Pro Gly Lys Glu Arg Glu Gly Val
        35                  40                  45

Ser Cys Ile Ser Ser Ser Gly Ser Thr Asn Tyr Ala Asp Ser Val
    50                  55                  60

Lys Gly Arg Phe Thr Ile Ser Arg Asp Asn Ser Lys Lys Ser Val Tyr
65                  70                  75                  80

Leu Gln Met Asn Ser Leu Lys Pro Glu Asp Thr Ala Ile Tyr Thr Cys
                85                  90                  95

Ala Ala Glu Arg Ala Pro Pro Tyr Tyr Ser Gly Tyr Tyr Phe Phe Asp
            100                 105                 110

Ser Thr Cys Val Ala Ala Ser Tyr Asp Tyr Trp Gly Gln Gly Thr Gln
        115                 120                 125

Val Thr Val Ser Ser
    130

<210> SEQ ID NO 12
<211> LENGTH: 121
<212> TYPE: PRT
<213> ORGANISM: Vicugna pacos

<400> SEQUENCE: 12

Gln Val Gln Leu Gln Glu Ser Gly Gly Gly Leu Val Gln Pro Gly Gly
1               5                   10                  15

Ser Leu Lys Leu Ser Cys Ala Ala Ser Gly Ser Ile Phe Ser Ile Lys
            20                  25                  30

Thr Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Gly Val Val Ala Trp Asp Gln Pro Tyr Asp Asn Tyr Trp Gly
            100                 105                 110

Gln Gly Thr Gln Val Thr Val Ser Ser
        115                 120

<210> SEQ ID NO 13
<211> LENGTH: 125
<212> TYPE: PRT
<213> ORGANISM: Vicugna pacos

<400> SEQUENCE: 13

Gln Val Gln Leu Gln Glu Ser Gly Gly Gly Leu Val Gln Ala Gly Asp
1               5                   10                  15

Ser Leu Ser Ile Ser Cys Ala Ala Ser Gly Asp Thr Phe Asn His Tyr
            20                  25                  30

Ser Trp Gly Trp Phe Arg Gln Ala Pro Gly Lys Ala Arg Glu Phe Val
        35                  40                  45

Ala Ala Ile Ser Trp Asn Gly Gly Ser Lys Tyr Ala Asp Ser Val Lys
            50                  55                  60

Gly Arg Phe Ala Ile Ser Arg Asp Ile Ala Lys Asn Thr Val Ser Leu
65                  70                  75                  80

Gln Met Asn Ser Leu Glu Pro Glu Asp Thr Ala Val Tyr Tyr Cys Ala
                85                  90                  95

Ala Asp Arg Arg Pro Tyr Asn Asp Trp Trp Asp Asp Trp Ser Trp Trp
            100                 105                 110

Val Tyr Trp Gly Gln Gly Thr Gln Val Thr Val Ser Ser
            115                 120                 125

<210> SEQ ID NO 14
<211> LENGTH: 127
<212> TYPE: PRT
<213> ORGANISM: Vicugna pacos

<400> SEQUENCE: 14

Gln Val Gln Leu Gln Glu Ser Gly Gly Gly Leu Val Gln Pro Gly Glu
1               5                   10                  15

Ser Leu Arg Leu Ser Cys Lys Leu Ser Gly Phe Thr Leu Asp Tyr Tyr
            20                  25                  30

Asp Ile Gly Trp Phe Arg Gln Ala Pro Gly Lys Glu Arg Glu Gly Val
            35                  40                  45

Ser Cys Ile Ser Ser Ile Gly Gly Ser Ala Asn Tyr Ala Asp Ser Val
            50                  55                  60

Lys Gly Arg Phe Thr Ile Ser Arg Asp Asn Val Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Glu Ala Gln Thr Pro Tyr Asn Asp Gly Asp Cys Thr Arg Ala
            100                 105                 110

Ser Tyr Asp Tyr Trp Gly Gln Gly Ile Gln Val Thr Val Ser Ser
            115                 120                 125

<210> SEQ ID NO 15
<211> LENGTH: 119
<212> TYPE: PRT
<213> ORGANISM: Vicugna pacos

<400> SEQUENCE: 15

Gln Val Gln Leu Gln Glu Ser Gly Gly Gly Leu Val Gln Pro Gly Gly
1               5                   10                  15

Ser Leu Arg Leu Ser Cys Val Val Ser Gly Ser Phe Leu Ser Ile Asn
            20                  25                  30

His Met Gly Trp Tyr Arg Gln Val Ser Gly Glu Gln Arg Glu Leu Val
            35                  40                  45

Ala Ala Ile Thr Ser Gly Gly Ser Thr Asn Tyr Ala Asp Ser Val Lys
            50                  55                  60

Gly Arg Phe Thr Ile Ser Arg Asp Ser Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Ala Leu Thr Met Leu Pro Pro Phe Asp Phe Trp Gly Gln Gly
            100                 105                 110

Thr Gln Val Thr Val Ser Ser
            115

<210> SEQ ID NO 16
<211> LENGTH: 120
<212> TYPE: PRT
<213> ORGANISM: Vicugna pacos

<400> SEQUENCE: 16

Gln Val Gln Leu Gln Glu Ser Gly Gly Gly Leu Val Gln Pro Gly Gly
1               5                   10                  15

Ser Leu Met Leu Ser Cys Ala Ala Ser Gly Asn Ile Phe Thr Ile Asn
            20                  25                  30

Arg Met Gly Trp Tyr Arg Gln Ala Pro Gly Lys Gln Arg Glu Leu Val
        35                  40                  45

Ala Ala Ile Thr Ser Gly Gly Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Ala Ile Val Thr Met Thr Ser Pro Tyr Ser Asp Tyr Trp Gly Gln
            100                 105                 110

Gly Thr Gln Val Thr Val Ser Ser
        115                 120

<210> SEQ ID NO 17
<211> LENGTH: 112
<212> TYPE: PRT
<213> ORGANISM: Vicugna pacos

<400> SEQUENCE: 17

Gln Val Gln Leu Gln Glu Ser Gly Gly Gly Thr Leu Val Gln Pro Gly Gly
1               5                   10                  15

Ser Leu Arg Leu Ser Cys Ala Ala Ser Gly Ser Thr Phe Ser Ile Asn
            20                  25                  30

Asn Met Gly Trp Tyr Arg Gln Ala Pro Gly Lys Gln Arg Glu Leu Val
        35                  40                  45

Ala Gly Ile Thr Gly Gly Asn Thr His Tyr Ala Asp Ser Val Lys Gly
    50                  55                  60

Arg Phe Thr Ile Ser Arg Asp Asn Ala Lys Asn Thr Met Tyr Leu Gln
65                  70                  75                  80

Met Asn Gly Leu Lys Pro Glu Asp Thr Ala Val Tyr Tyr Cys Asn Ala
                85                  90                  95

Asn Trp Gly Ala Tyr Trp Gly Gln Gly Thr Gln Val Thr Val Ser Ser
            100                 105                 110

<210> SEQ ID NO 18
<211> LENGTH: 121
<212> TYPE: PRT
<213> ORGANISM: Vicugna pacos

<400> SEQUENCE: 18

Gln Val Gln Leu Gln Glu Ser Gly Gly Gly Leu Val Gln Pro Gly Gly
1               5                   10                  15

Ser Leu Gly Leu Ser Cys Ala Ala Ser Gly Arg Ile Ala Ser Ile Ser
            20                  25                  30

Ala Met Gly Trp Tyr Arg Gln Ala Pro Gly Lys Gln Arg Glu Leu Val
        35                  40                  45

```
Ala Ala Ile Thr Gly Ser Gly Arg Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Leu Leu Met Val Asp Tyr Gly Leu Gly Leu Gly Thr Asp Tyr Trp Gly
            100                 105                 110

Gln Gly Thr Gln Val Thr Val Ser Ser
            115                 120

<210> SEQ ID NO 19
<211> LENGTH: 130
<212> TYPE: PRT
<213> ORGANISM: Vicugna pacos

<400> SEQUENCE: 19

Gln Val Gln Leu Gln Glu Ser Gly Gly Gly Leu Val Gln Pro Gly Gly
 1               5                   10                  15

Ser Leu Arg Leu Ser Cys Ala Ala Ser Gly Pro Gly Phe Lys Leu Asp
             20                  25                  30

Tyr Tyr Ala Ile Ala Trp Phe Arg Gln Ala Pro Gly Lys Glu Arg Glu
         35                  40                  45

Gly Val Ser Cys Ile Gly Gly Ser Gly Ser Gly Leu Thr Thr Tyr Val
     50                  55                  60

Glu Asn Ser Val Lys Asp Arg Phe Thr Ile Ser Arg Asp Asn Ala Gln
 65                  70                  75                  80

Asn Thr Val Tyr Leu His Met Asn Ser Leu Lys Pro Glu Asp Thr Gly
                 85                  90                  95

Ile Tyr Tyr Cys Ala Ala Asp Thr Tyr Tyr Cys Ser Lys Arg Val
            100                 105                 110

Trp Arg Asn Asp Tyr Gly Ser Trp Gly Gln Gly Thr Gln Val Thr Val
            115                 120                 125

Ser Ser
130

<210> SEQ ID NO 20
<211> LENGTH: 125
<212> TYPE: PRT
<213> ORGANISM: Vicugna pacos

<400> SEQUENCE: 20

Gln Val Gln Leu Gln Glu Ser Gly Gly Gly Leu Val Gln Ala Gly Gly
 1               5                   10                  15

Ser Leu Arg Leu Ser Cys Ala Ala Ser Gly Gly Thr Phe Asp Asp Ser
             20                  25                  30

Val Ile Gly Trp Phe Arg Gln Ala Pro Gly Lys Glu Arg Glu Gly Val
         35                  40                  45

Ser Cys Ile Ser Ser Asn Asp Gly Thr Thr His Tyr Ala Ser Pro Val
     50                  55                  60

Lys Gly Arg Phe Thr Ile Ser Ser Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Glu Thr Pro Ser Ile Gly Ser Pro Cys Thr Ser Ala Ser Tyr
            100                 105                 110
```

```
Asp Tyr Trp Gly Gln Gly Thr Gln Val Thr Val Ser Ser
        115                 120                 125

<210> SEQ ID NO 21
<211> LENGTH: 125
<212> TYPE: PRT
<213> ORGANISM: Vicugna pacos

<400> SEQUENCE: 21

Gln Val Gln Leu Gln Glu Ser Gly Gly Gly Leu Val Gln Pro Gly Gly
1               5                   10                  15

Ser Leu Arg Leu Ser Cys Thr Ala Thr Gly Phe Thr Leu Lys Asn His
            20                  25                  30

His Ile Gly Trp Leu Arg Gln Ala Pro Gly Lys Glu Arg Glu Gly Val
        35                  40                  45

Ala Ser Ile Asn Ser Ser Gly Gly Ser Thr Asn Tyr Ala Asp Ser Val
    50                  55                  60

Gln Gly Arg Phe Thr Ile Ser Arg Asp Asn Ala Lys Asn Thr Val Phe
65                  70                  75                  80

Leu Gln Met Asn Ser Leu Lys Ser Glu Asp Thr Ala Val Tyr Tyr Cys
                85                  90                  95

Ala Arg Leu Arg Arg Tyr Tyr Gly Leu Asn Leu Asp Pro Gly Ser Tyr
            100                 105                 110

Asp Tyr Trp Gly Gln Gly Thr Gln Val Thr Val Ser Ser
        115                 120                 125

<210> SEQ ID NO 22
<211> LENGTH: 124
<212> TYPE: PRT
<213> ORGANISM: Vicugna pacos

<400> SEQUENCE: 22

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ile Phe Ser Ala Tyr
            20                  25                  30

Ala Met Gly Trp Phe Arg Gln Ala Pro Gly Lys Glu Arg Glu Phe Val
        35                  40                  45

Ala Ala Ile Ser Arg Ser Gly Asp Ser Thr Asp Tyr Ala Asp Ser Val
    50                  55                  60

Lys Gly Arg Phe Thr Ile Ser Arg Asp Ser Ala Lys Asn Met Val Tyr
65                  70                  75                  80

Leu Gln Met Asn Ser Leu Lys Pro Glu Asp Thr Ala Leu Tyr His Cys
                85                  90                  95

Ala Ala Arg Thr Val Ser Ala Pro Pro Ser Ala Ala Trp Gly Tyr Gly
            100                 105                 110

Tyr Trp Gly Gln Gly Thr Gln Val Thr Val Ser Ser
        115                 120

<210> SEQ ID NO 23
<211> LENGTH: 130
<212> TYPE: PRT
<213> ORGANISM: Vicugna pacos

<400> SEQUENCE: 23

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Phe Ser Asn Tyr
```

```
                    20                  25                  30
Val Asn Tyr Ala Met Gly Trp Phe Arg Gln Phe Pro Gly Lys Glu Arg
                35                  40                  45

Glu Phe Val Ala Ser Ile Ser Trp Ser Ser Val Thr Thr Tyr Tyr Ala
            50                  55                  60

Asp Ser Val Lys Gly Arg Phe Thr Ile Ser Arg Asp Asn Ala Lys Asn
 65                  70                  75                  80

Thr Val Tyr Leu Gln Met Asn Ser Leu Lys Pro Glu Asp Thr Ala Val
                85                  90                  95

Tyr Tyr Cys Ala Ala His Leu Ala Gln Tyr Ser Asp Tyr Ala Tyr Arg
            100                 105                 110

Asp Pro His Gln Phe Gly Ala Trp Gly Gln Gly Thr Gln Val Thr Val
                115                 120                 125

Ser Ser
    130
```

<210> SEQ ID NO 24
<211> LENGTH: 117
<212> TYPE: PRT
<213> ORGANISM: Vicugna pacos

<400> SEQUENCE: 24

```
Gln Val Gln Leu Gln Glu Ser Gly Gly Gly Leu Val Gln Ala Gly Gly
1               5                   10                  15

Ser Leu Arg Leu Ser Cys Leu Ala Ser Gly Asp Thr Phe Ser Asn Tyr
                20                  25                  30

Val Met Ala Trp Phe Arg Gln Ala Pro Gly Lys Glu Arg Glu Ile Val
            35                  40                  45

Ala Ala Ile Arg Leu Ser Gly Ala Arg Tyr Val Pro Asp Ser Val Lys
        50                  55                  60

Gly Arg Phe Thr Ile Ser Arg Asp Asn Ala Lys Asn Ala Met Tyr Leu
65                  70                  75                  80

Gln Met Thr Ser Leu Lys Pro Glu Asp Thr Ala Arg Tyr Tyr Cys Ala
                85                  90                  95

Ala Gly His Thr Trp Gly Gln Tyr Ala Tyr Trp Gly Gln Gly Thr Gln
            100                 105                 110

Val Thr Val Ser Ser
        115
```

<210> SEQ ID NO 25
<211> LENGTH: 119
<212> TYPE: PRT
<213> ORGANISM: Vicugna pacos

<400> SEQUENCE: 25

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Ala
                20                  25                  30

Ala Met Gly Trp Phe Arg Gln Ala Pro Gly Lys Glu Arg Glu Pro Val
            35                  40                  45

Ala Leu Ile Asn Leu Asp Asp Gly Glu Thr Tyr Tyr Ala Asp Ile Ala
        50                  55                  60

Lys Gly Arg Phe Thr Leu Ser Lys Asp Asn Ala Lys Asn Ser Val Tyr
65                  70                  75                  80

Leu Gln Met Asn Ser Leu Lys Pro Glu Asp Thr Ala Val Tyr Tyr Cys
```

```
                85                  90                  95
Ala Val Arg Gly Arg Phe Asp Asp Asn Tyr Glu Tyr Trp Gly Gln Gly
            100                 105                 110

Thr Gln Val Thr Val Ser Ser
        115
```

<210> SEQ ID NO 26
<211> LENGTH: 122
<212> TYPE: PRT
<213> ORGANISM: Vicugna pacos

<400> SEQUENCE: 26

```
Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Thr Phe Ser Ile Asn
            20                  25                  30

Tyr Met Gly Trp Tyr Arg Gln Ala Pro Gly Lys Gln Arg Glu Leu Val
            35                  40                  45

Ala Ala Ile Thr Ser Gly Ser Gly Ser Thr Asn Tyr Ala Asp Ser Val
        50                  55                  60

Lys Gly Arg Phe Thr Ile Ser Arg Asp Asn Ala Lys Lys Thr Met Tyr
65                  70                  75                  80

Leu Gln Met Asn Ser Leu Lys Pro Glu Asp Thr Ala Val Tyr Tyr Cys
                85                  90                  95

Asn Ala Asp Met Asp Ser Ser Leu Ser Gly Tyr Val Asp Val Trp
            100                 105                 110

Gly Gln Gly Thr Gln Val Thr Val Ser Ser
            115                 120
```

<210> SEQ ID NO 27
<211> LENGTH: 112
<212> TYPE: PRT
<213> ORGANISM: Vicugna pacos

<400> SEQUENCE: 27

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Ile Asn
            20                  25                  30

Asn Met Gly Trp Tyr Arg Gln Ala Pro Gly Lys Gln Arg Glu Leu Val
            35                  40                  45

Ala Gly Ile Thr Gly Gly Asn Thr His Tyr Ala Asp Ser Val Lys Gly
        50                  55                  60

Arg Phe Thr Ile Ser Arg Asp Asn Ala Lys Asn Thr Met Tyr Leu Gln
65                  70                  75                  80

Met Asn Ser Leu Lys Pro Glu Asp Thr Ala Val Tyr Tyr Cys Asn Ala
                85                  90                  95

Asn Trp Gly Ala Tyr Trp Gly Gln Gly Thr Gln Val Thr Val Ser Ser
            100                 105                 110
```

<210> SEQ ID NO 28
<211> LENGTH: 119
<212> TYPE: PRT
<213> ORGANISM: Vicugna pacos

<400> SEQUENCE: 28

```
Gln Val Gln Leu Gln Glu Ser Gly Gly Gly Leu Val Gln Pro Gly Gly
1               5                   10                  15
```

```
Ser Leu Arg Leu Ser Cys Ala Ala Ser Gly Ser Ile Val Ser Ile Asn
            20                  25                  30

Ala Met Gly Trp Tyr Arg Gln Ala Pro Gly Lys Gln Arg Glu Leu Val
        35                  40                  45

Ala Leu Val Thr Gly Ser Gly Arg Thr Asn Leu Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                85                  90                  95

Val Leu Val Ile Gly Pro Leu Glu Gly Tyr Asp Tyr Trp Gly Gln Gly
            100                 105                 110

Thr Gln Val Thr Val Ser Ser
        115

<210> SEQ ID NO 29
<211> LENGTH: 121
<212> TYPE: PRT
<213> ORGANISM: Vicugna pacos

<400> SEQUENCE: 29

Gln Val Gln Leu Gln Glu Ser Gly Gly Gly Leu Val Gln Pro Gly Gly
 1               5                   10                  15

Ser Leu Lys Leu Ser Cys Ala Ala Ser Gly Ser Ile Phe Ser Ile Lys
            20                  25                  30

Thr Met Gly Trp Tyr Arg Gln Ala Pro Gly Lys Gln Arg Glu Leu Val
        35                  40                  45

Ala Ala Val Ser Ser Gly Gly Ser Thr Asn Tyr Ala Asp Ser Val Lys
 50                  55                  60

Gly Arg Phe Thr Ile Ser Arg Asp Asn Ala Lys Asn Ala Val Tyr Leu
 65                  70                  75                  80

Gln Met Asn Ser Leu Lys Pro Glu Asp Thr Ala Val Tyr Tyr Cys Asn
                85                  90                  95

Ala Asp Gly Val Val Ala Trp Asp Gln Pro Tyr Asp Asn Tyr Trp Gly
            100                 105                 110

Gln Gly Thr Gln Val Thr Val Ser Ser
        115                 120

<210> SEQ ID NO 30
<211> LENGTH: 118
<212> TYPE: PRT
<213> ORGANISM: Vicugna pacos

<400> SEQUENCE: 30

Gln Val Gln Leu Gln Glu Ser Gly Gly Gly Leu Val Gln Ala Gly Gly
 1               5                   10                  15

Ser Leu Arg Leu Ser Cys Val Asp Gln Gly Arg Thr Phe Ser Val Asn
            20                  25                  30

Ala Met Ala Trp Tyr Arg Gln Ala Pro Gly Lys Gln Arg Glu Leu Val
        35                  40                  45

Ala Ser Ile Thr Ser Ser Gly Leu Asp Thr Gln Tyr Ala Glu Gly Met
 50                  55                  60

Lys Gly Arg Phe Thr Ile Ser Lys Gly Asn Asp Lys Phe Ser Thr Tyr
 65                  70                  75                  80

Leu Gln Met Asn Asn Leu Lys Pro Asp Asp Thr Ala Val Tyr Tyr Cys
                85                  90                  95
```

```
Asn Ala Glu Arg Trp Asp Asn Gly Met Val Tyr Trp Gly Lys Gly Thr
                100                 105                 110

Gln Val Thr Val Ser Ser
            115

<210> SEQ ID NO 31
<211> LENGTH: 132
<212> TYPE: PRT
<213> ORGANISM: Vicugna pacos

<400> SEQUENCE: 31

Gln Val Gln Leu Gln Glu Ser Gly Gly Gly Leu Val Gln Ala Gly Asp
1               5                   10                  15

Ser Leu Arg Leu Ser Cys Leu Ala Thr Gly Ser Met Phe Ser Ile Asn
            20                  25                  30

Ala Trp Gly Trp Tyr Arg Gln Ala Pro Gly Lys Gln Arg Glu Leu Val
        35                  40                  45

Ala Ser Ile Thr Ser Gly Gly Ser Thr Glu Tyr Ala Glu Ser Val
50                  55                  60

Lys Gly Arg Phe Thr Ile Ser Arg Asp Ser Ala Lys Asn Met Leu Tyr
65                  70                  75                  80

Leu Gln Met Asn Ser Leu Arg Pro Glu Asp Thr Ala Val Tyr Tyr Cys
                85                  90                  95

Asn Ala Glu Arg Trp Asp Gly Tyr Ala Leu Gly Tyr Ser Pro Asn His
                100                 105                 110

Gly Ser Gly His Arg Pro Tyr Asn Tyr Trp Gly Gln Gly Thr Gln Val
            115                 120                 125

Thr Val Ser Ser
        130

<210> SEQ ID NO 32
<211> LENGTH: 120
<212> TYPE: PRT
<213> ORGANISM: Vicugna pacos

<400> SEQUENCE: 32

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Trp Gly Trp Tyr Arg Gln Ala Pro Gly Lys Gln Arg Glu Leu Val
        35                  40                  45

Ala Glu Ile Thr Ser Ser Gly Ser Thr Asn Tyr Ala Asp Ser Val Lys
50                  55                  60

Gly Arg Phe Thr Ile Ser Gly Asp Asn Ala Lys Asn Ser Val Tyr Leu
65                  70                  75                  80

His Met Asn Asn Leu Glu Pro Glu Asp Thr Ala Val Tyr Tyr Cys Lys
                85                  90                  95

Ala Val Ala Val Thr Phe Thr Thr Pro Arg Ser Asp Tyr Trp Gly Arg
                100                 105                 110

Gly Thr Gln Val Thr Val Ser Ser
            115                 120

<210> SEQ ID NO 33
<211> LENGTH: 116
<212> TYPE: PRT
<213> ORGANISM: Vicugna pacos
```

```
<400> SEQUENCE: 33

Gln Val Gln Leu Gln Glu Ser Gly Gly Gly Leu Val Gln Pro Gly Gly
1               5                   10                  15

Ser Leu Arg Leu Ser Cys Ala Pro Ser Gly Ile Ile Ser Ile Asn
            20                  25                  30

Ala Met Ala Trp Tyr Arg Gln Ala Pro Gly Lys Glu Arg Glu Leu Val
        35                  40                  45

Ala Ala Ile Ser Ser Gly Gly Ser Thr Tyr Tyr Ala Asp Ser Val Lys
    50                  55                  60

Gly Arg Phe Thr Ile Ser Gly Asp Ile Ala Lys Asn Leu Leu Trp Leu
65                  70                  75                  80

Gln Met Asn Ser Leu Lys Pro Glu Asp Thr Ala Met Tyr Tyr Cys Ala
                85                  90                  95

Pro Gly Gly Gly Trp Arg Pro Gly Ala Trp Gly Gln Gly Thr Gln Val
            100                 105                 110

Thr Val Ser Ser
        115

<210> SEQ ID NO 34
<211> LENGTH: 116
<212> TYPE: PRT
<213> ORGANISM: Vicugna pacos

<400> SEQUENCE: 34

Gln Val Gln Leu Gln Glu Ser Gly Gly Gly Leu Val Gln Pro Gly Gly
1               5                   10                  15

Ser Leu Arg Leu Ser Cys Ala Gly Ser Gly Phe Thr Val Ser Thr Ser
            20                  25                  30

Met Ile Asn Trp Ala Arg Gln Val Pro Gly Lys Glu Leu Glu Trp Leu
        35                  40                  45

Val Asp Val Leu Pro Ser Gly Ser Thr Tyr Tyr Ala Asp Pro Val Lys
    50                  55                  60

Gly Arg Phe Thr Ile Ser Arg Asp Asn Ala Gln Asn Thr Ile Tyr Leu
65                  70                  75                  80

Gln Met Asn Tyr Leu Lys Pro Glu Asp Thr Ala Ile Tyr Tyr Cys Ala
                85                  90                  95

Ile Asn Arg Glu Thr Met Pro Pro Phe Arg Gly Gln Gly Thr Gln Val
            100                 105                 110

Thr Val Ser Ser
        115

<210> SEQ ID NO 35
<211> LENGTH: 121
<212> TYPE: PRT
<213> ORGANISM: Vicugna pacos

<400> SEQUENCE: 35

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Pro Phe Ser Ser Ala
            20                  25                  30

Pro Met Ser Trp Val Arg Gln Ala Pro Gly Lys Glu Leu Glu Trp Val
        35                  40                  45

Ser Tyr Ile Gly Tyr Thr Gly Thr Ile Thr Asp Tyr Ala Asn Ser Val
    50                  55                  60
```

```
Lys Gly Arg Phe Thr Ile Ser Arg Asp Asn Ala Lys Asn Arg Leu Tyr
 65                  70                  75                  80

Leu Gln Met Asn Ser Leu Lys Pro Glu Asp Thr Ala Val Tyr Phe Cys
                 85                  90                  95

Ala Gln Gly Tyr Ala Arg Leu Ile Ala Asp Ser Asp Leu Val Arg Gly
            100                 105                 110

Gln Gly Thr Gln Val Thr Val Ser Ser
            115                 120

<210> SEQ ID NO 36
<211> LENGTH: 121
<212> TYPE: PRT
<213> ORGANISM: Vicugna pacos

<400> SEQUENCE: 36

Gln Val Gln Leu Gln Glu Ser Gly Gly Arg Leu Gly Ala Ala Gly Gly
1               5                   10                  15

Ser Leu Arg Leu Ser Cys Thr Ala Ser Gly Phe Pro Phe Asn Ile Tyr
            20                  25                  30

Pro Met Ser Trp Val Arg Gln Ala Pro Gly Lys Gly Phe Glu Trp Val
            35                  40                  45

Ser Tyr Ile Ser His Gly Gly Thr Thr Thr Asp Tyr Ser Asp Ala Val
        50                  55                  60

Lys Gly Arg Phe Thr Ile Ser Arg Asp Asn Ala Lys Asn Arg Leu Tyr
 65                  70                  75                  80

Leu Gln Met Asn Ser Leu Lys Pro Glu Asp Thr Ala Val Tyr Phe Cys
                 85                  90                  95

Ala Gln Gly Tyr Ala Arg Leu Met Thr Asp Ser Glu Leu Val Arg Gly
            100                 105                 110

Gln Gly Thr Gln Val Thr Val Ser Ser
            115                 120

<210> SEQ ID NO 37
<211> LENGTH: 25
<212> TYPE: PRT
<213> ORGANISM: Vicugna pacos

<400> SEQUENCE: 37

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 38
<211> LENGTH: 25
<212> TYPE: PRT
<213> ORGANISM: Vicugna pacos

<400> SEQUENCE: 38

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 39
<211> LENGTH: 25
<212> TYPE: PRT
<213> ORGANISM: Vicugna pacos

<400> SEQUENCE: 39
```

-continued

Gln Val Gln Leu Gln Glu Ser Gly Gly Gly Leu Val Gln Ala Gly Asp
1               5                   10                  15

Ser Leu Arg Leu Ser Cys Ala Ala Ser
            20                  25

<210> SEQ ID NO 40
<211> LENGTH: 25
<212> TYPE: PRT
<213> ORGANISM: Vicugna pacos

<400> SEQUENCE: 40

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 41
<211> LENGTH: 25
<212> TYPE: PRT
<213> ORGANISM: Vicugna pacos

<400> SEQUENCE: 41

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 42
<211> LENGTH: 25
<212> TYPE: PRT
<213> ORGANISM: Vicugna pacos

<400> SEQUENCE: 42

Gln Val Gln Leu Gln Glu Ser Gly Gly Gly Leu Val Gln Pro Gly Gly
1               5                   10                  15

Ser Leu Lys Leu Ser Cys Ala Ala Ser
            20                  25

<210> SEQ ID NO 43
<211> LENGTH: 25
<212> TYPE: PRT
<213> ORGANISM: Vicugna pacos

<400> SEQUENCE: 43

Gln Val Gln Leu Gln Glu Ser Gly Gly Gly Leu Val Gln Ala Gly Asp
1               5                   10                  15

Ser Leu Ser Ile Ser Cys Ala Ala Ser
            20                  25

<210> SEQ ID NO 44
<211> LENGTH: 25
<212> TYPE: PRT
<213> ORGANISM: Vicugna pacos

<400> SEQUENCE: 44

Gln Val Gln Leu Gln Glu Ser Gly Gly Gly Leu Val Gln Pro Gly Glu
1               5                   10                  15

Ser Leu Arg Leu Ser Cys Lys Leu Ser
            20                  25

<210> SEQ ID NO 45

```
<211> LENGTH: 25
<212> TYPE: PRT
<213> ORGANISM: Vicugna pacos

<400> SEQUENCE: 45

Gln Val Gln Leu Gln Glu Ser Gly Gly Gly Leu Val Gln Pro Gly Gly
1               5                   10                  15

Ser Leu Arg Leu Ser Cys Val Val Ser
            20                  25

<210> SEQ ID NO 46
<211> LENGTH: 25
<212> TYPE: PRT
<213> ORGANISM: Vicugna pacos

<400> SEQUENCE: 46

Gln Val Gln Leu Gln Glu Ser Gly Gly Gly Leu Val Gln Pro Gly Gly
1               5                   10                  15

Ser Leu Met Leu Ser Cys Ala Ala Ser
            20                  25

<210> SEQ ID NO 47
<211> LENGTH: 25
<212> TYPE: PRT
<213> ORGANISM: Vicugna pacos

<400> SEQUENCE: 47

Gln Val Gln Leu Gln Glu Ser Gly Gly Thr Leu Val Gln Pro Gly Gly
1               5                   10                  15

Ser Leu Arg Leu Ser Cys Ala Ala Ser
            20                  25

<210> SEQ ID NO 48
<211> LENGTH: 25
<212> TYPE: PRT
<213> ORGANISM: Vicugna pacos

<400> SEQUENCE: 48

Gln Val Gln Leu Gln Glu Ser Gly Gly Gly Leu Val Gln Pro Gly Gly
1               5                   10                  15

Ser Leu Gly Leu Ser Cys Ala Ala Ser
            20                  25

<210> SEQ ID NO 49
<211> LENGTH: 26
<212> TYPE: PRT
<213> ORGANISM: Vicugna pacos

<400> SEQUENCE: 49

Gln Val Gln Leu Gln Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 50
<211> LENGTH: 25
<212> TYPE: PRT
<213> ORGANISM: Vicugna pacos

<400> SEQUENCE: 50

Gln Val Gln Leu Gln Glu Ser Gly Gly Gly Leu Val Gln Ala Gly Gly
1               5                   10                  15
```

```
<210> SEQ ID NO 51
<211> LENGTH: 25
<212> TYPE: PRT
<213> ORGANISM: Vicugna pacos

<400> SEQUENCE: 51

Gln Val Gln Leu Gln Glu Ser Gly Gly Gly Leu Val Gln Pro Gly Gly
1               5                   10                  15

Ser Leu Arg Leu Ser Cys Thr Ala Thr
            20                  25

<210> SEQ ID NO 52
<211> LENGTH: 25
<212> TYPE: PRT
<213> ORGANISM: Vicugna pacos

<400> SEQUENCE: 52

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 53
<211> LENGTH: 25
<212> TYPE: PRT
<213> ORGANISM: Vicugna pacos

<400> SEQUENCE: 53

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 54
<211> LENGTH: 25
<212> TYPE: PRT
<213> ORGANISM: Vicugna pacos

<400> SEQUENCE: 54

Gln Val Gln Leu Gln Glu Ser Gly Gly Gly Leu Val Gln Ala Gly Gly
1               5                   10                  15

Ser Leu Arg Leu Ser Cys Leu Ala Ser
            20                  25

<210> SEQ ID NO 55
<211> LENGTH: 25
<212> TYPE: PRT
<213> ORGANISM: Vicugna pacos

<400> SEQUENCE: 55

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 56
<211> LENGTH: 25
<212> TYPE: PRT
<213> ORGANISM: Vicugna pacos
```

-continued

```
<400> SEQUENCE: 56

Gln Val Gln Leu Gln Glu Ser Gly Gly Gly Leu Val Gln Ala Gly Asp
1               5                   10                  15

Ser Leu Arg Leu Ser Cys Ala Ala Ser
            20                  25

<210> SEQ ID NO 57
<211> LENGTH: 25
<212> TYPE: PRT
<213> ORGANISM: Vicugna pacos

<400> SEQUENCE: 57

Gln Val Gln Leu Gln Glu Ser Gly Gly Gly Leu Val Gln Ala Gly Gly
1               5                   10                  15

Ser Leu Arg Leu Ser Cys Ala Ala Ser
            20                  25

<210> SEQ ID NO 58
<211> LENGTH: 25
<212> TYPE: PRT
<213> ORGANISM: Vicugna pacos

<400> SEQUENCE: 58

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 59
<211> LENGTH: 25
<212> TYPE: PRT
<213> ORGANISM: Vicugna pacos

<400> SEQUENCE: 59

Gln Val Gln Leu Gln Glu Ser Gly Gly Gly Leu Val Gln Pro Gly Gly
1               5                   10                  15

Ser Leu Lys Leu Ser Cys Ala Ala Ser
            20                  25

<210> SEQ ID NO 60
<211> LENGTH: 25
<212> TYPE: PRT
<213> ORGANISM: Vicugna pacos

<400> SEQUENCE: 60

Gln Val Gln Leu Gln Glu Ser Gly Gly Gly Leu Val Gln Ala Gly Gly
1               5                   10                  15

Ser Leu Arg Leu Ser Cys Val Asp Gln
            20                  25

<210> SEQ ID NO 61
<211> LENGTH: 25
<212> TYPE: PRT
<213> ORGANISM: Vicugna pacos

<400> SEQUENCE: 61

Gln Val Gln Leu Gln Glu Ser Gly Gly Gly Leu Val Gln Ala Gly Asp
1               5                   10                  15

Ser Leu Arg Leu Ser Cys Leu Ala Thr
            20                  25
```

```
<210> SEQ ID NO 62
<211> LENGTH: 25
<212> TYPE: PRT
<213> ORGANISM: Vicugna pacos

<400> SEQUENCE: 62

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 63
<211> LENGTH: 25
<212> TYPE: PRT
<213> ORGANISM: Vicugna pacos

<400> SEQUENCE: 63

Gln Val Gln Leu Gln Glu Ser Gly Gly Gly Leu Val Gln Pro Gly Gly
1               5                   10                  15

Ser Leu Arg Leu Ser Cys Ala Pro Ser
            20                  25

<210> SEQ ID NO 64
<211> LENGTH: 25
<212> TYPE: PRT
<213> ORGANISM: Vicugna pacos

<400> SEQUENCE: 64

Gln Val Gln Leu Gln Glu Ser Gly Gly Gly Leu Val Gln Pro Gly Gly
1               5                   10                  15

Ser Leu Arg Leu Ser Cys Ala Gly Ser
            20                  25

<210> SEQ ID NO 65
<211> LENGTH: 25
<212> TYPE: PRT
<213> ORGANISM: Vicugna pacos

<400> SEQUENCE: 65

Gln Val Gln Leu Gln Glu Ser Gly Gly Gly Leu Val Gln Pro Gly Gly
1               5                   10                  15

Ser Leu Arg Leu Ser Cys Thr Ala Ser
            20                  25

<210> SEQ ID NO 66
<211> LENGTH: 25
<212> TYPE: PRT
<213> ORGANISM: Vicugna pacos

<400> SEQUENCE: 66

Gln Val Gln Leu Gln Glu Ser Gly Gly Arg Leu Gly Ala Ala Gly Gly
1               5                   10                  15

Ser Leu Arg Leu Ser Cys Thr Ala Ser
            20                  25

<210> SEQ ID NO 67
<211> LENGTH: 10
<212> TYPE: PRT
<213> ORGANISM: Vicugna pacos

<400> SEQUENCE: 67

Gly Phe Ser Leu Asp Tyr Tyr Ala Ile Gly
1               5                   10
```

<210> SEQ ID NO 68
<211> LENGTH: 10
<212> TYPE: PRT
<213> ORGANISM: Vicugna pacos

<400> SEQUENCE: 68

Gly Phe Thr Leu Asp Tyr Tyr Ala Ile Gly
1               5                   10

<210> SEQ ID NO 69
<211> LENGTH: 10
<212> TYPE: PRT
<213> ORGANISM: Vicugna pacos

<400> SEQUENCE: 69

Gly Arg Thr Phe Ser Ile Asn Tyr Met Gly
1               5                   10

<210> SEQ ID NO 70
<211> LENGTH: 10
<212> TYPE: PRT
<213> ORGANISM: Vicugna pacos

<400> SEQUENCE: 70

Gly Phe Thr Asp Asp Tyr Asp Ile Gly
1               5                   10

<210> SEQ ID NO 71
<211> LENGTH: 10
<212> TYPE: PRT
<213> ORGANISM: Vicugna pacos

<400> SEQUENCE: 71

Gly Phe Thr Leu Asp Asn Tyr Thr Val Ala
1               5                   10

<210> SEQ ID NO 72
<211> LENGTH: 10
<212> TYPE: PRT
<213> ORGANISM: Vicugna pacos

<400> SEQUENCE: 72

Gly Ser Ile Phe Ser Ile Lys Thr Met Gly
1               5                   10

<210> SEQ ID NO 73
<211> LENGTH: 10
<212> TYPE: PRT
<213> ORGANISM: Vicugna pacos

<400> SEQUENCE: 73

Gly Asp Thr Phe Asn His Tyr Ser Trp Gly
1               5                   10

<210> SEQ ID NO 74
<211> LENGTH: 10
<212> TYPE: PRT
<213> ORGANISM: Vicugna pacos

<400> SEQUENCE: 74

Gly Phe Thr Leu Asp Tyr Tyr Asp Ile Gly
1               5                   10

```
<210> SEQ ID NO 75
<211> LENGTH: 10
<212> TYPE: PRT
<213> ORGANISM: Vicugna pacos

<400> SEQUENCE: 75

Gly Ser Phe Leu Ser Ile Asn His Met Gly
1               5                   10

<210> SEQ ID NO 76
<211> LENGTH: 10
<212> TYPE: PRT
<213> ORGANISM: Vicugna pacos

<400> SEQUENCE: 76

Gly Asn Ile Phe Thr Ile Asn Arg Met Gly
1               5                   10

<210> SEQ ID NO 77
<211> LENGTH: 10
<212> TYPE: PRT
<213> ORGANISM: Vicugna pacos

<400> SEQUENCE: 77

Gly Ser Thr Phe Ser Ile Asn Asn Met Gly
1               5                   10

<210> SEQ ID NO 78
<211> LENGTH: 10
<212> TYPE: PRT
<213> ORGANISM: Vicugna pacos

<400> SEQUENCE: 78

Gly Arg Ile Ala Ser Ile Ser Ala Met Gly
1               5                   10

<210> SEQ ID NO 79
<211> LENGTH: 11
<212> TYPE: PRT
<213> ORGANISM: Vicugna pacos

<400> SEQUENCE: 79

Pro Gly Phe Lys Leu Asp Tyr Tyr Ala Ile Ala
1               5                   10

<210> SEQ ID NO 80
<211> LENGTH: 10
<212> TYPE: PRT
<213> ORGANISM: Vicugna pacos

<400> SEQUENCE: 80

Gly Gly Thr Phe Asp Asp Ser Val Ile Gly
1               5                   10

<210> SEQ ID NO 81
<211> LENGTH: 10
<212> TYPE: PRT
<213> ORGANISM: Vicugna pacos

<400> SEQUENCE: 81

Gly Phe Thr Leu Lys Asn His His Ile Gly
1               5                   10

<210> SEQ ID NO 82
<211> LENGTH: 10
```

```
<212> TYPE: PRT
<213> ORGANISM: Vicugna pacos

<400> SEQUENCE: 82

Gly Arg Ile Phe Ser Ala Tyr Ala Met Gly
1               5                   10

<210> SEQ ID NO 83
<211> LENGTH: 13
<212> TYPE: PRT
<213> ORGANISM: Vicugna pacos

<400> SEQUENCE: 83

Gly Arg Thr Phe Ser Asn Tyr Val Asn Tyr Ala Met Gly
1               5                   10

<210> SEQ ID NO 84
<211> LENGTH: 10
<212> TYPE: PRT
<213> ORGANISM: Vicugna pacos

<400> SEQUENCE: 84

Gly Asp Thr Phe Ser Asn Tyr Val Met Ala
1               5                   10

<210> SEQ ID NO 85
<211> LENGTH: 10
<212> TYPE: PRT
<213> ORGANISM: Vicugna pacos

<400> SEQUENCE: 85

Gly Arg Thr Phe Ser Ser Ala Ala Met Gly
1               5                   10

<210> SEQ ID NO 86
<211> LENGTH: 10
<212> TYPE: PRT
<213> ORGANISM: Vicugna pacos

<400> SEQUENCE: 86

Gly Arg Thr Phe Ser Ile Asn Tyr Met Gly
1               5                   10

<210> SEQ ID NO 87
<211> LENGTH: 10
<212> TYPE: PRT
<213> ORGANISM: Vicugna pacos

<400> SEQUENCE: 87

Gly Ser Thr Phe Ser Ile Asn Asn Met Gly
1               5                   10

<210> SEQ ID NO 88
<211> LENGTH: 10
<212> TYPE: PRT
<213> ORGANISM: Vicugna pacos

<400> SEQUENCE: 88

Gly Ser Ile Val Ser Ile Asn Ala Met Gly
1               5                   10

<210> SEQ ID NO 89
<211> LENGTH: 10
<212> TYPE: PRT
<213> ORGANISM: Vicugna pacos
```

<400> SEQUENCE: 89

Gly Ser Ile Phe Ser Ile Lys Thr Met Gly
1               5                   10

<210> SEQ ID NO 90
<211> LENGTH: 10
<212> TYPE: PRT
<213> ORGANISM: Vicugna pacos

<400> SEQUENCE: 90

Gly Arg Thr Phe Ser Val Asn Ala Met Ala
1               5                   10

<210> SEQ ID NO 91
<211> LENGTH: 10
<212> TYPE: PRT
<213> ORGANISM: Vicugna pacos

<400> SEQUENCE: 91

Gly Ser Met Phe Ser Ile Asn Ala Trp Gly
1               5                   10

<210> SEQ ID NO 92
<211> LENGTH: 10
<212> TYPE: PRT
<213> ORGANISM: Vicugna pacos

<400> SEQUENCE: 92

Gly Ser Ile Phe Ser Ile Asn Ala Trp Gly
1               5                   10

<210> SEQ ID NO 93
<211> LENGTH: 10
<212> TYPE: PRT
<213> ORGANISM: Vicugna pacos

<400> SEQUENCE: 93

Gly Ser Ile Ile Ser Ile Asn Ala Met Ala
1               5                   10

<210> SEQ ID NO 94
<211> LENGTH: 10
<212> TYPE: PRT
<213> ORGANISM: Vicugna pacos

<400> SEQUENCE: 94

Gly Phe Thr Val Ser Thr Ser Met Ile Asn
1               5                   10

<210> SEQ ID NO 95
<211> LENGTH: 10
<212> TYPE: PRT
<213> ORGANISM: Vicugna pacos

<400> SEQUENCE: 95

Gly Phe Pro Phe Ser Ser Ala Pro Met Ser
1               5                   10

<210> SEQ ID NO 96
<211> LENGTH: 10
<212> TYPE: PRT
<213> ORGANISM: Vicugna pacos

<400> SEQUENCE: 96

```
Gly Phe Pro Phe Asn Ile Tyr Pro Met Ser
1               5                   10

<210> SEQ ID NO 97
<211> LENGTH: 14
<212> TYPE: PRT
<213> ORGANISM: Vicugna pacos

<400> SEQUENCE: 97

Trp Phe Arg Gln Ala Pro Gly Lys Glu Arg Glu Gly Ile Ser
1               5                   10

<210> SEQ ID NO 98
<211> LENGTH: 14
<212> TYPE: PRT
<213> ORGANISM: Vicugna pacos

<400> SEQUENCE: 98

Trp Phe Arg Gln Ala Pro Gly Lys Glu Arg Glu Gly Ile Ser
1               5                   10

<210> SEQ ID NO 99
<211> LENGTH: 14
<212> TYPE: PRT
<213> ORGANISM: Vicugna pacos

<400> SEQUENCE: 99

Trp Tyr Arg Gln Ala Pro Gly Lys Gln Arg Glu Leu Val Ala
1               5                   10

<210> SEQ ID NO 100
<211> LENGTH: 14
<212> TYPE: PRT
<213> ORGANISM: Vicugna pacos

<400> SEQUENCE: 100

Trp Phe Arg Gln Ala Pro Gly Lys Glu Arg Glu Gly Val Ser
1               5                   10

<210> SEQ ID NO 101
<211> LENGTH: 14
<212> TYPE: PRT
<213> ORGANISM: Vicugna pacos

<400> SEQUENCE: 101

Trp Phe Arg Gln Ala Pro Gly Lys Glu Arg Glu Gly Val Ser
1               5                   10

<210> SEQ ID NO 102
<211> LENGTH: 14
<212> TYPE: PRT
<213> ORGANISM: Vicugna pacos

<400> SEQUENCE: 102

Trp Tyr Arg Gln Ala Pro Gly Lys Gln Arg Glu Leu Val Ala
1               5                   10

<210> SEQ ID NO 103
<211> LENGTH: 14
<212> TYPE: PRT
<213> ORGANISM: Vicugna pacos

<400> SEQUENCE: 103

Trp Phe Arg Gln Ala Pro Gly Lys Ala Arg Glu Phe Val Ala
```

-continued

```
1               5                   10

<210> SEQ ID NO 104
<211> LENGTH: 14
<212> TYPE: PRT
<213> ORGANISM: Vicugna pacos

<400> SEQUENCE: 104

Trp Phe Arg Gln Ala Pro Gly Lys Glu Arg Glu Gly Val Ser
1               5                   10

<210> SEQ ID NO 105
<211> LENGTH: 14
<212> TYPE: PRT
<213> ORGANISM: Vicugna pacos

<400> SEQUENCE: 105

Trp Tyr Arg Gln Val Ser Gly Glu Gln Arg Glu Leu Val Ala
1               5                   10

<210> SEQ ID NO 106
<211> LENGTH: 14
<212> TYPE: PRT
<213> ORGANISM: Vicugna pacos

<400> SEQUENCE: 106

Trp Tyr Arg Gln Ala Pro Gly Lys Gln Arg Glu Leu Val Ala
1               5                   10

<210> SEQ ID NO 107
<211> LENGTH: 14
<212> TYPE: PRT
<213> ORGANISM: Vicugna pacos

<400> SEQUENCE: 107

Trp Tyr Arg Gln Ala Pro Gly Lys Gln Arg Glu Leu Val Ala
1               5                   10

<210> SEQ ID NO 108
<211> LENGTH: 14
<212> TYPE: PRT
<213> ORGANISM: Vicugna pacos

<400> SEQUENCE: 108

Trp Tyr Arg Gln Ala Pro Gly Lys Gln Arg Glu Leu Val Ala
1               5                   10

<210> SEQ ID NO 109
<211> LENGTH: 14
<212> TYPE: PRT
<213> ORGANISM: Vicugna pacos

<400> SEQUENCE: 109

Trp Phe Arg Gln Ala Pro Gly Lys Glu Arg Glu Gly Val Ser
1               5                   10

<210> SEQ ID NO 110
<211> LENGTH: 14
<212> TYPE: PRT
<213> ORGANISM: Vicugna pacos

<400> SEQUENCE: 110

Trp Phe Arg Gln Ala Pro Gly Lys Glu Arg Glu Gly Val Ser
1               5                   10
```

<210> SEQ ID NO 111
<211> LENGTH: 14
<212> TYPE: PRT
<213> ORGANISM: Vicugna pacos

<400> SEQUENCE: 111

Trp Leu Arg Gln Ala Pro Gly Lys Glu Arg Glu Gly Val Ala
1               5                   10

<210> SEQ ID NO 112
<211> LENGTH: 14
<212> TYPE: PRT
<213> ORGANISM: Vicugna pacos

<400> SEQUENCE: 112

Trp Phe Arg Gln Ala Pro Gly Lys Glu Arg Glu Phe Val Ala
1               5                   10

<210> SEQ ID NO 113
<211> LENGTH: 14
<212> TYPE: PRT
<213> ORGANISM: Vicugna pacos

<400> SEQUENCE: 113

Trp Phe Arg Gln Phe Pro Gly Lys Glu Arg Glu Phe Val Ala
1               5                   10

<210> SEQ ID NO 114
<211> LENGTH: 14
<212> TYPE: PRT
<213> ORGANISM: Vicugna pacos

<400> SEQUENCE: 114

Trp Phe Arg Gln Ala Pro Gly Lys Glu Arg Glu Ile Val Ala
1               5                   10

<210> SEQ ID NO 115
<211> LENGTH: 14
<212> TYPE: PRT
<213> ORGANISM: Vicugna pacos

<400> SEQUENCE: 115

Trp Phe Arg Gln Ala Pro Gly Lys Glu Arg Glu Pro Val Ala
1               5                   10

<210> SEQ ID NO 116
<211> LENGTH: 14
<212> TYPE: PRT
<213> ORGANISM: Vicugna pacos

<400> SEQUENCE: 116

Trp Tyr Arg Gln Ala Pro Gly Lys Gln Arg Glu Leu Val Ala
1               5                   10

<210> SEQ ID NO 117
<211> LENGTH: 14
<212> TYPE: PRT
<213> ORGANISM: Vicugna pacos

<400> SEQUENCE: 117

Trp Tyr Arg Gln Ala Pro Gly Lys Gln Arg Glu Leu Val Ala
1               5                   10

<210> SEQ ID NO 118

-continued

```
<211> LENGTH: 14
<212> TYPE: PRT
<213> ORGANISM: Vicugna pacos

<400> SEQUENCE: 118

Trp Tyr Arg Gln Ala Pro Gly Lys Gln Arg Glu Leu Val Ala
1               5                   10

<210> SEQ ID NO 119
<211> LENGTH: 14
<212> TYPE: PRT
<213> ORGANISM: Vicugna pacos

<400> SEQUENCE: 119

Trp Tyr Arg Gln Ala Pro Gly Lys Gln Arg Glu Leu Val Ala
1               5                   10

<210> SEQ ID NO 120
<211> LENGTH: 14
<212> TYPE: PRT
<213> ORGANISM: Vicugna pacos

<400> SEQUENCE: 120

Trp Tyr Arg Gln Ala Pro Gly Lys Gln Arg Glu Leu Val Ala
1               5                   10

<210> SEQ ID NO 121
<211> LENGTH: 14
<212> TYPE: PRT
<213> ORGANISM: Vicugna pacos

<400> SEQUENCE: 121

Trp Tyr Arg Gln Ala Pro Gly Lys Gln Arg Glu Leu Val Ala
1               5                   10

<210> SEQ ID NO 122
<211> LENGTH: 14
<212> TYPE: PRT
<213> ORGANISM: Vicugna pacos

<400> SEQUENCE: 122

Trp Tyr Arg Gln Ala Pro Gly Lys Gln Arg Glu Leu Val Ala
1               5                   10

<210> SEQ ID NO 123
<211> LENGTH: 14
<212> TYPE: PRT
<213> ORGANISM: Vicugna pacos

<400> SEQUENCE: 123

Trp Tyr Arg Gln Ala Pro Gly Lys Glu Arg Glu Leu Val Ala
1               5                   10

<210> SEQ ID NO 124
<211> LENGTH: 14
<212> TYPE: PRT
<213> ORGANISM: Vicugna pacos

<400> SEQUENCE: 124

Trp Ala Arg Gln Val Pro Gly Lys Glu Leu Glu Trp Leu Val
1               5                   10

<210> SEQ ID NO 125
<211> LENGTH: 14
<212> TYPE: PRT
```

<213> ORGANISM: Vicugna pacos

<400> SEQUENCE: 125

Trp Val Arg Gln Ala Pro Gly Lys Glu Leu Glu Trp Val Ser
1               5                   10

<210> SEQ ID NO 126
<211> LENGTH: 14
<212> TYPE: PRT
<213> ORGANISM: Vicugna pacos

<400> SEQUENCE: 126

Trp Val Arg Gln Ala Pro Gly Lys Gly Phe Glu Trp Val Ser
1               5                   10

<210> SEQ ID NO 127
<211> LENGTH: 9
<212> TYPE: PRT
<213> ORGANISM: Vicugna pacos

<400> SEQUENCE: 127

Cys Ile Ser Tyr Lys Gly Gly Ser Thr
1               5

<210> SEQ ID NO 128
<211> LENGTH: 9
<212> TYPE: PRT
<213> ORGANISM: Vicugna pacos

<400> SEQUENCE: 128

Cys Ile Ser Tyr Lys Gly Gly Ser Thr
1               5

<210> SEQ ID NO 129
<211> LENGTH: 9
<212> TYPE: PRT
<213> ORGANISM: Vicugna pacos

<400> SEQUENCE: 129

Ala Ile Thr Ser Gly Ser Gly Ser Thr
1               5

<210> SEQ ID NO 130
<211> LENGTH: 9
<212> TYPE: PRT
<213> ORGANISM: Vicugna pacos

<400> SEQUENCE: 130

Cys Ile Ser Ser Ser Asp Gly Ser Thr
1               5

<210> SEQ ID NO 131
<211> LENGTH: 9
<212> TYPE: PRT
<213> ORGANISM: Vicugna pacos

<400> SEQUENCE: 131

Cys Ile Ser Ser Ser Gly Gly Ser Thr
1               5

<210> SEQ ID NO 132
<211> LENGTH: 8
<212> TYPE: PRT
<213> ORGANISM: Vicugna pacos

```
<400> SEQUENCE: 132

Ala Ile Thr Ser Gly Gly Ser Thr
1               5

<210> SEQ ID NO 133
<211> LENGTH: 8
<212> TYPE: PRT
<213> ORGANISM: Vicugna pacos

<400> SEQUENCE: 133

Ala Ile Ser Trp Asn Gly Gly Ser
1               5

<210> SEQ ID NO 134
<211> LENGTH: 9
<212> TYPE: PRT
<213> ORGANISM: Vicugna pacos

<400> SEQUENCE: 134

Cys Ile Ser Ser Ile Gly Gly Ser Ala
1               5

<210> SEQ ID NO 135
<211> LENGTH: 8
<212> TYPE: PRT
<213> ORGANISM: Vicugna pacos

<400> SEQUENCE: 135

Ala Ile Thr Ser Gly Gly Ser Thr
1               5

<210> SEQ ID NO 136
<211> LENGTH: 8
<212> TYPE: PRT
<213> ORGANISM: Vicugna pacos

<400> SEQUENCE: 136

Ala Ile Thr Ser Gly Gly Asn Thr
1               5

<210> SEQ ID NO 137
<211> LENGTH: 7
<212> TYPE: PRT
<213> ORGANISM: Vicugna pacos

<400> SEQUENCE: 137

Gly Ile Thr Gly Gly Asn Thr
1               5

<210> SEQ ID NO 138
<211> LENGTH: 8
<212> TYPE: PRT
<213> ORGANISM: Vicugna pacos

<400> SEQUENCE: 138

Ala Ile Thr Gly Ser Gly Arg Thr
1               5

<210> SEQ ID NO 139
<211> LENGTH: 10
<212> TYPE: PRT
<213> ORGANISM: Vicugna pacos

<400> SEQUENCE: 139
```

```
Cys Ile Gly Gly Ser Gly Ser Gly Leu Thr
1               5                   10

<210> SEQ ID NO 140
<211> LENGTH: 9
<212> TYPE: PRT
<213> ORGANISM: Vicugna pacos

<400> SEQUENCE: 140

Cys Ile Ser Ser Asn Asp Gly Thr Thr
1               5

<210> SEQ ID NO 141
<211> LENGTH: 9
<212> TYPE: PRT
<213> ORGANISM: Vicugna pacos

<400> SEQUENCE: 141

Ser Ile Asn Ser Ser Gly Gly Ser Thr
1               5

<210> SEQ ID NO 142
<211> LENGTH: 9
<212> TYPE: PRT
<213> ORGANISM: Vicugna pacos

<400> SEQUENCE: 142

Ala Ile Ser Arg Ser Gly Asp Ser Thr
1               5

<210> SEQ ID NO 143
<211> LENGTH: 9
<212> TYPE: PRT
<213> ORGANISM: Vicugna pacos

<400> SEQUENCE: 143

Ser Ile Ser Trp Ser Ser Val Thr Thr
1               5

<210> SEQ ID NO 144
<211> LENGTH: 8
<212> TYPE: PRT
<213> ORGANISM: Vicugna pacos

<400> SEQUENCE: 144

Ala Ile Arg Leu Ser Gly Ala Arg
1               5

<210> SEQ ID NO 145
<211> LENGTH: 9
<212> TYPE: PRT
<213> ORGANISM: Vicugna pacos

<400> SEQUENCE: 145

Leu Ile Asn Leu Asp Asp Gly Glu Thr
1               5

<210> SEQ ID NO 146
<211> LENGTH: 9
<212> TYPE: PRT
<213> ORGANISM: Vicugna pacos

<400> SEQUENCE: 146

Ala Ile Thr Ser Gly Ser Gly Ser Thr
1               5
```

<210> SEQ ID NO 147
<211> LENGTH: 7
<212> TYPE: PRT
<213> ORGANISM: Vicugna pacos

<400> SEQUENCE: 147

Gly Ile Thr Gly Gly Asn Thr
1               5

<210> SEQ ID NO 148
<211> LENGTH: 8
<212> TYPE: PRT
<213> ORGANISM: Vicugna pacos

<400> SEQUENCE: 148

Leu Val Thr Gly Ser Gly Arg Thr
1               5

<210> SEQ ID NO 149
<211> LENGTH: 8
<212> TYPE: PRT
<213> ORGANISM: Vicugna pacos

<400> SEQUENCE: 149

Ala Val Ser Ser Gly Gly Ser Thr
1               5

<210> SEQ ID NO 150
<211> LENGTH: 9
<212> TYPE: PRT
<213> ORGANISM: Vicugna pacos

<400> SEQUENCE: 150

Ser Ile Thr Ser Ser Gly Leu Asp Thr
1               5

<210> SEQ ID NO 151
<211> LENGTH: 9
<212> TYPE: PRT
<213> ORGANISM: Vicugna pacos

<400> SEQUENCE: 151

Ser Ile Thr Ser Gly Gly Gly Ser Thr
1               5

<210> SEQ ID NO 152
<211> LENGTH: 8
<212> TYPE: PRT
<213> ORGANISM: Vicugna pacos

<400> SEQUENCE: 152

Glu Ile Thr Ser Ser Gly Ser Thr
1               5

<210> SEQ ID NO 153
<211> LENGTH: 8
<212> TYPE: PRT
<213> ORGANISM: Vicugna pacos

<400> SEQUENCE: 153

Ala Ile Ser Ser Gly Gly Ser Thr
1               5

-continued

```
<210> SEQ ID NO 154
<211> LENGTH: 8
<212> TYPE: PRT
<213> ORGANISM: Vicugna pacos

<400> SEQUENCE: 154

Asp Val Leu Pro Ser Gly Ser Thr
1               5

<210> SEQ ID NO 155
<211> LENGTH: 9
<212> TYPE: PRT
<213> ORGANISM: Vicugna pacos

<400> SEQUENCE: 155

Tyr Ile Gly Tyr Thr Gly Thr Ile Thr
1               5

<210> SEQ ID NO 156
<211> LENGTH: 9
<212> TYPE: PRT
<213> ORGANISM: Vicugna pacos

<400> SEQUENCE: 156

Tyr Ile Ser His Gly Gly Thr Thr Thr
1               5

<210> SEQ ID NO 157
<211> LENGTH: 40
<212> TYPE: PRT
<213> ORGANISM: Vicugna pacos

<400> SEQUENCE: 157

Thr Tyr Ala Asp Ser Val Lys Gly Arg Phe Thr Ile Ser Lys Asp Asn
1               5                   10                  15

Ala Lys Asn Thr Ala Tyr Leu Gln Met Asn Ser Leu Lys Pro Glu Asp
            20                  25                  30

Thr Gly Ile Tyr Ser Cys Ala Ala
        35                  40

<210> SEQ ID NO 158
<211> LENGTH: 40
<212> TYPE: PRT
<213> ORGANISM: Vicugna pacos

<400> SEQUENCE: 158

Thr Tyr Ala Asp Ser Val Lys Gly Arg Phe Thr Ile Ser Lys Asp Asn
1               5                   10                  15

Ala Lys Asn Thr Ala Tyr Leu Gln Met Asn Asn Leu Lys Pro Glu Asp
            20                  25                  30

Thr Gly Ile Tyr Tyr Cys Ala Ala
        35                  40

<210> SEQ ID NO 159
<211> LENGTH: 40
<212> TYPE: PRT
<213> ORGANISM: Vicugna pacos

<400> SEQUENCE: 159

Asn Tyr Ala Asp Ser Val Lys Gly Arg Phe Thr Ile Ser Arg Asp Asn
1               5                   10                  15

Ala Lys Asn Thr Met Tyr Leu Gln Met Asn Ser Leu Lys Pro Glu Asp
            20                  25                  30
```

Thr Ala Val Tyr Tyr Cys Asn Ala
        35                  40

<210> SEQ ID NO 160
<211> LENGTH: 40
<212> TYPE: PRT
<213> ORGANISM: Vicugna pacos

<400> SEQUENCE: 160

Tyr Tyr Ala Asp Ser Val Lys Gly Arg Phe Thr Ile Ser Ser Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys Ala Ala
        35                  40

<210> SEQ ID NO 161
<211> LENGTH: 40
<212> TYPE: PRT
<213> ORGANISM: Vicugna pacos

<400> SEQUENCE: 161

Asn Tyr Ala Asp Ser Val Lys Gly Arg Phe Thr Ile Ser Arg Asp Asn
1               5                   10                  15

Ser Lys Lys Ser Val Tyr Leu Gln Met Asn Ser Leu Lys Pro Glu Asp
            20                  25                  30

Thr Ala Ile Tyr Thr Cys Ala Ala
        35                  40

<210> SEQ ID NO 162
<211> LENGTH: 40
<212> TYPE: PRT
<213> ORGANISM: Vicugna pacos

<400> SEQUENCE: 162

Asn Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys Asn Ala
        35                  40

<210> SEQ ID NO 163
<211> LENGTH: 40
<212> TYPE: PRT
<213> ORGANISM: Vicugna pacos

<400> SEQUENCE: 163

Lys Tyr Ala Asp Ser Val Lys Gly Arg Phe Ala Ile Ser Arg Asp Ile
1               5                   10                  15

Ala Lys Asn Thr Val Ser Leu Gln Met Asn Ser Leu Glu Pro Glu Asp
            20                  25                  30

Thr Ala Val Tyr Tyr Cys Ala Ala
        35                  40

<210> SEQ ID NO 164
<211> LENGTH: 40
<212> TYPE: PRT
<213> ORGANISM: Vicugna pacos

<400> SEQUENCE: 164

Asn Tyr Ala Asp Ser Val Lys Gly Arg Phe Thr Ile Ser Arg Asp Asn
1               5                   10                  15

Val Lys Asn Thr Val Tyr Leu Gln Met Asn Ser Leu Lys Pro Glu Asp
            20                  25                  30

Thr Ala Ile Tyr Tyr Cys Ala Ala
        35                  40

<210> SEQ ID NO 165
<211> LENGTH: 40
<212> TYPE: PRT
<213> ORGANISM: Vicugna pacos

<400> SEQUENCE: 165

Asn Tyr Ala Asp Ser Val Lys Gly Arg Phe Thr Ile Ser Arg Asp Ser
1               5                   10                  15

Ala Lys Asn Thr Val Tyr Leu Gln Met Asn Ser Leu Lys Pro Glu Asp
            20                  25                  30

Thr Ala Val Tyr Tyr Cys Asn Ala
        35                  40

<210> SEQ ID NO 166
<211> LENGTH: 40
<212> TYPE: PRT
<213> ORGANISM: Vicugna pacos

<400> SEQUENCE: 166

Asn Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys Asn Ala
        35                  40

<210> SEQ ID NO 167
<211> LENGTH: 40
<212> TYPE: PRT
<213> ORGANISM: Vicugna pacos

<400> SEQUENCE: 167

His Tyr Ala Asp Ser Val Lys Gly Arg Phe Thr Ile Ser Arg Asp Asn
1               5                   10                  15

Ala Lys Asn Thr Met Tyr Leu Gln Met Asn Gly Leu Lys Pro Glu Asp
            20                  25                  30

Thr Ala Val Tyr Tyr Cys Asn Ala
        35                  40

<210> SEQ ID NO 168
<211> LENGTH: 40
<212> TYPE: PRT
<213> ORGANISM: Vicugna pacos

<400> SEQUENCE: 168

Asn Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys Asn Leu
        35                  40

```
<210> SEQ ID NO 169
<211> LENGTH: 41
<212> TYPE: PRT
<213> ORGANISM: Vicugna pacos

<400> SEQUENCE: 169

Thr Tyr Val Glu Asn Ser Val Lys Asp Arg Phe Thr Ile Ser Arg Asp
1               5                   10                  15

Asn Ala Gln Asn Thr Val Tyr Leu His Met Asn Ser Leu Lys Pro Glu
            20                  25                  30

Asp Thr Gly Ile Tyr Tyr Cys Ala Ala
        35                  40

<210> SEQ ID NO 170
<211> LENGTH: 40
<212> TYPE: PRT
<213> ORGANISM: Vicugna pacos

<400> SEQUENCE: 170

His Tyr Ala Ser Pro Val Lys Gly Arg Phe Thr Ile Ser Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys Ala Ala
        35                  40

<210> SEQ ID NO 171
<211> LENGTH: 40
<212> TYPE: PRT
<213> ORGANISM: Vicugna pacos

<400> SEQUENCE: 171

Asn Tyr Ala Asp Ser Val Gln Gly Arg Phe Thr Ile Ser Arg Asp Asn
1               5                   10                  15

Ala Lys Asn Thr Val Phe Leu Gln Met Asn Ser Leu Lys Ser Glu Asp
            20                  25                  30

Thr Ala Val Tyr Tyr Cys Ala Arg
        35                  40

<210> SEQ ID NO 172
<211> LENGTH: 40
<212> TYPE: PRT
<213> ORGANISM: Vicugna pacos

<400> SEQUENCE: 172

Asp Tyr Ala Asp Ser Val Lys Gly Arg Phe Thr Ile Ser Arg Asp Ser
1               5                   10                  15

Ala Lys Asn Met Val Tyr Leu Gln Met Asn Ser Leu Lys Pro Glu Asp
            20                  25                  30

Thr Ala Leu Tyr His Cys Ala Ala
        35                  40

<210> SEQ ID NO 173
<211> LENGTH: 40
<212> TYPE: PRT
<213> ORGANISM: Vicugna pacos

<400> SEQUENCE: 173

Tyr Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
```

-continued

```
                20                  25                  30

Thr Ala Val Tyr Tyr Cys Ala Ala
        35                  40

<210> SEQ ID NO 174
<211> LENGTH: 40
<212> TYPE: PRT
<213> ORGANISM: Vicugna pacos

<400> SEQUENCE: 174

Tyr Val Pro Asp Ser Val Lys Gly Arg Phe Thr Ile Ser Arg Asp Asn
1               5                   10                  15

Ala Lys Asn Ala Met Tyr Leu Gln Met Thr Ser Leu Lys Pro Glu Asp
                20                  25                  30

Thr Ala Arg Tyr Tyr Cys Ala Ala
        35                  40

<210> SEQ ID NO 175
<211> LENGTH: 40
<212> TYPE: PRT
<213> ORGANISM: Vicugna pacos

<400> SEQUENCE: 175

Tyr Tyr Ala Asp Ile Ala Lys Gly Arg Phe Thr Leu Ser Lys Asp Asn
1               5                   10                  15

Ala Lys Asn Ser Val Tyr Leu Gln Met Asn Ser Leu Lys Pro Glu Asp
                20                  25                  30

Thr Ala Val Tyr Tyr Cys Ala Val
        35                  40

<210> SEQ ID NO 176
<211> LENGTH: 40
<212> TYPE: PRT
<213> ORGANISM: Vicugna pacos

<400> SEQUENCE: 176

Asn Tyr Ala Asp Ser Val Lys Gly Arg Phe Thr Ile Ser Arg Asp Asn
1               5                   10                  15

Ala Lys Lys Thr Met Tyr Leu Gln Met Asn Ser Leu Lys Pro Glu Asp
                20                  25                  30

Thr Ala Val Tyr Tyr Cys Asn Ala
        35                  40

<210> SEQ ID NO 177
<211> LENGTH: 40
<212> TYPE: PRT
<213> ORGANISM: Vicugna pacos

<400> SEQUENCE: 177

His Tyr Ala Asp Ser Val Lys Gly Arg Phe Thr Ile Ser Arg Asp Asn
1               5                   10                  15

Ala Lys Asn Thr Met Tyr Leu Gln Met Asn Ser Leu Lys Pro Glu Asp
                20                  25                  30

Thr Ala Val Tyr Tyr Cys Asn Ala
        35                  40

<210> SEQ ID NO 178
<211> LENGTH: 40
<212> TYPE: PRT
<213> ORGANISM: Vicugna pacos
```

-continued

<400> SEQUENCE: 178

Asn Leu Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
            20                  25                  30

Thr Ala Val Tyr Tyr Cys Asn Val
        35                  40

<210> SEQ ID NO 179
<211> LENGTH: 40
<212> TYPE: PRT
<213> ORGANISM: Vicugna pacos

<400> SEQUENCE: 179

Asn Tyr Ala Asp Ser Val Lys Gly Arg Phe Thr Ile Ser Arg Asp Asn
1               5                   10                  15

Ala Lys Asn Ala Val Tyr Leu Gln Met Asn Ser Leu Lys Pro Glu Asp
            20                  25                  30

Thr Ala Val Tyr Tyr Cys Asn Ala
        35                  40

<210> SEQ ID NO 180
<211> LENGTH: 40
<212> TYPE: PRT
<213> ORGANISM: Vicugna pacos

<400> SEQUENCE: 180

Gln Tyr Ala Glu Gly Met Lys Gly Arg Phe Thr Ile Ser Lys Gly Asn
1               5                   10                  15

Asp Lys Phe Ser Thr Tyr Leu Gln Met Asn Asn Leu Lys Pro Asp Asp
            20                  25                  30

Thr Ala Val Tyr Tyr Cys Asn Ala
        35                  40

<210> SEQ ID NO 181
<211> LENGTH: 40
<212> TYPE: PRT
<213> ORGANISM: Vicugna pacos

<400> SEQUENCE: 181

Glu Tyr Ala Glu Ser Val Lys Gly Arg Phe Thr Ile Ser Arg Asp Ser
1               5                   10                  15

Ala Lys Asn Met Leu Tyr Leu Gln Met Asn Ser Leu Arg Pro Glu Asp
            20                  25                  30

Thr Ala Val Tyr Tyr Cys Asn Ala
        35                  40

<210> SEQ ID NO 182
<211> LENGTH: 40
<212> TYPE: PRT
<213> ORGANISM: Vicugna pacos

<400> SEQUENCE: 182

Asn Tyr Ala Asp Ser Val Lys Gly Arg Phe Thr Ile Ser Gly Asp Asn
1               5                   10                  15

Ala Lys Asn Ser Val Tyr Leu His Met Asn Asn Leu Glu Pro Glu Asp
            20                  25                  30

Thr Ala Val Tyr Tyr Cys Lys Ala
        35                  40

```
<210> SEQ ID NO 183
<211> LENGTH: 40
<212> TYPE: PRT
<213> ORGANISM: Vicugna pacos

<400> SEQUENCE: 183

Tyr Tyr Ala Asp Ser Val Lys Gly Arg Phe Thr Ile Ser Gly Asp Ile
1               5                   10                  15

Ala Lys Asn Leu Leu Trp Leu Gln Met Asn Ser Leu Lys Pro Glu Asp
            20                  25                  30

Thr Ala Met Tyr Tyr Cys Ala Pro
        35                  40

<210> SEQ ID NO 184
<211> LENGTH: 40
<212> TYPE: PRT
<213> ORGANISM: Vicugna pacos

<400> SEQUENCE: 184

Tyr Tyr Ala Asp Pro Val Lys Gly Arg Phe Thr Ile Ser Arg Asp Asn
1               5                   10                  15

Ala Gln Asn Thr Ile Tyr Leu Gln Met Asn Tyr Leu Lys Pro Glu Asp
            20                  25                  30

Thr Ala Ile Tyr Tyr Cys Ala Ile
        35                  40

<210> SEQ ID NO 185
<211> LENGTH: 40
<212> TYPE: PRT
<213> ORGANISM: Vicugna pacos

<400> SEQUENCE: 185

Asp Tyr Ala Asn Ser Val Lys Gly Arg Phe Thr Ile Ser Arg Asp Asn
1               5                   10                  15

Ala Lys Asn Arg Leu Tyr Leu Gln Met Asn Ser Leu Lys Pro Glu Asp
            20                  25                  30

Thr Ala Val Tyr Phe Cys Ala Gln
        35                  40

<210> SEQ ID NO 186
<211> LENGTH: 40
<212> TYPE: PRT
<213> ORGANISM: Vicugna pacos

<400> SEQUENCE: 186

Asp Tyr Ser Asp Ala Val Lys Gly Arg Phe Thr Ile Ser Arg Asp Asn
1               5                   10                  15

Ala Lys Asn Arg Leu Tyr Leu Gln Met Asp Ser Leu Lys Pro Glu Asp
            20                  25                  30

Thr Ala Val Tyr Phe Cys Ala Gln
        35                  40

<210> SEQ ID NO 187
<211> LENGTH: 9
<212> TYPE: PRT
<213> ORGANISM: Vicugna pacos

<400> SEQUENCE: 187

Gly Phe Val Cys Tyr Asn Tyr Asp Tyr
1               5
```

<210> SEQ ID NO 188
<211> LENGTH: 9
<212> TYPE: PRT
<213> ORGANISM: Vicugna pacos

<400> SEQUENCE: 188

Gly Phe Val Cys Tyr Asn Tyr Asp Tyr
1               5

<210> SEQ ID NO 189
<211> LENGTH: 13
<212> TYPE: PRT
<213> ORGANISM: Vicugna pacos

<400> SEQUENCE: 189

Asp Met Asp Ser Ser Leu Ser Gly Gly Tyr Val Asp Val
1               5                   10

<210> SEQ ID NO 190
<211> LENGTH: 22
<212> TYPE: PRT
<213> ORGANISM: Vicugna pacos

<400> SEQUENCE: 190

Asp Phe Phe Arg Trp Asp Ser Gly Ser Tyr Tyr Val Arg Gly Cys Arg
1               5                   10                  15

His Ala Thr Tyr Asp Tyr
            20

<210> SEQ ID NO 191
<211> LENGTH: 24
<212> TYPE: PRT
<213> ORGANISM: Vicugna pacos

<400> SEQUENCE: 191

Glu Arg Ala Pro Pro Tyr Tyr Ser Gly Tyr Tyr Phe Phe Asp Ser Thr
1               5                   10                  15

Cys Val Ala Ala Ser Tyr Asp Tyr
            20

<210> SEQ ID NO 192
<211> LENGTH: 13
<212> TYPE: PRT
<213> ORGANISM: Vicugna pacos

<400> SEQUENCE: 192

Asp Gly Val Val Ala Trp Asp Gln Pro Tyr Asp Asn Tyr
1               5                   10

<210> SEQ ID NO 193
<211> LENGTH: 17
<212> TYPE: PRT
<213> ORGANISM: Vicugna pacos

<400> SEQUENCE: 193

Asp Arg Arg Pro Tyr Asn Asp Trp Trp Asp Asp Trp Ser Trp Trp Val
1               5                   10                  15

Tyr

<210> SEQ ID NO 194
<211> LENGTH: 18
<212> TYPE: PRT
<213> ORGANISM: Vicugna pacos

<400> SEQUENCE: 194

Glu Ala Gln Thr Pro Tyr Asn Asp Gly Asp Cys Thr Arg Ala Ser Tyr
1               5                   10                  15

Asp Tyr

<210> SEQ ID NO 195
<211> LENGTH: 11
<212> TYPE: PRT
<213> ORGANISM: Vicugna pacos

<400> SEQUENCE: 195

Asp Ala Leu Thr Met Leu Pro Pro Phe Asp Phe
1               5                   10

<210> SEQ ID NO 196
<211> LENGTH: 12
<212> TYPE: PRT
<213> ORGANISM: Vicugna pacos

<400> SEQUENCE: 196

Ala Ile Val Thr Met Thr Ser Pro Tyr Ser Asp Tyr
1               5                   10

<210> SEQ ID NO 197
<211> LENGTH: 5
<212> TYPE: PRT
<213> ORGANISM: Vicugna pacos

<400> SEQUENCE: 197

Asn Trp Gly Ala Tyr
1               5

<210> SEQ ID NO 198
<211> LENGTH: 13
<212> TYPE: PRT
<213> ORGANISM: Vicugna pacos

<400> SEQUENCE: 198

Leu Met Val Asp Tyr Gly Leu Gly Leu Gly Thr Asp Tyr
1               5                   10

<210> SEQ ID NO 199
<211> LENGTH: 17
<212> TYPE: PRT
<213> ORGANISM: Vicugna pacos

<400> SEQUENCE: 199

Asp Thr Tyr Tyr Tyr Cys Ser Lys Arg Val Trp Arg Asn Asp Tyr Gly
1               5                   10                  15

Ser

<210> SEQ ID NO 200
<211> LENGTH: 16
<212> TYPE: PRT
<213> ORGANISM: Vicugna pacos

<400> SEQUENCE: 200

Glu Thr Pro Ser Ile Gly Ser Pro Cys Thr Ser Ala Ser Tyr Asp Tyr
1               5                   10                  15

<210> SEQ ID NO 201
<211> LENGTH: 16

```
<212> TYPE: PRT
<213> ORGANISM: Vicugna pacos

<400> SEQUENCE: 201

Leu Arg Arg Tyr Tyr Gly Leu Asn Leu Asp Pro Gly Ser Tyr Asp Tyr
1               5                   10                  15

<210> SEQ ID NO 202
<211> LENGTH: 15
<212> TYPE: PRT
<213> ORGANISM: Vicugna pacos

<400> SEQUENCE: 202

Arg Thr Val Ser Ala Pro Pro Ser Ala Ala Trp Gly Tyr Gly Tyr
1               5                   10                  15

<210> SEQ ID NO 203
<211> LENGTH: 18
<212> TYPE: PRT
<213> ORGANISM: Vicugna pacos

<400> SEQUENCE: 203

His Leu Ala Gln Tyr Ser Asp Tyr Ala Tyr Arg Asp Pro His Gln Phe
1               5                   10                  15

Gly Ala

<210> SEQ ID NO 204
<211> LENGTH: 9
<212> TYPE: PRT
<213> ORGANISM: Vicugna pacos

<400> SEQUENCE: 204

Gly His Thr Trp Gly Gln Tyr Ala Tyr
1               5

<210> SEQ ID NO 205
<211> LENGTH: 10
<212> TYPE: PRT
<213> ORGANISM: Vicugna pacos

<400> SEQUENCE: 205

Arg Gly Arg Phe Asp Asp Asn Tyr Glu Tyr
1               5                   10

<210> SEQ ID NO 206
<211> LENGTH: 13
<212> TYPE: PRT
<213> ORGANISM: Vicugna pacos

<400> SEQUENCE: 206

Asp Met Asp Ser Ser Leu Ser Gly Gly Tyr Val Asp Val
1               5                   10

<210> SEQ ID NO 207
<211> LENGTH: 5
<212> TYPE: PRT
<213> ORGANISM: Vicugna pacos

<400> SEQUENCE: 207

Asn Trp Gly Ala Tyr
1               5

<210> SEQ ID NO 208
<211> LENGTH: 11
```

<212> TYPE: PRT
<213> ORGANISM: Vicugna pacos

<400> SEQUENCE: 208

Leu Val Ile Gly Pro Leu Glu Gly Tyr Asp Tyr
1               5                   10

<210> SEQ ID NO 209
<211> LENGTH: 13
<212> TYPE: PRT
<213> ORGANISM: Vicugna pacos

<400> SEQUENCE: 209

Asp Gly Val Val Ala Trp Asp Gln Pro Tyr Asp Asn Tyr
1               5                   10

<210> SEQ ID NO 210
<211> LENGTH: 9
<212> TYPE: PRT
<213> ORGANISM: Vicugna pacos

<400> SEQUENCE: 210

Glu Arg Trp Asp Asn Gly Met Val Tyr
1               5

<210> SEQ ID NO 211
<211> LENGTH: 23
<212> TYPE: PRT
<213> ORGANISM: Vicugna pacos

<400> SEQUENCE: 211

Glu Arg Trp Asp Gly Tyr Ala Leu Gly Tyr Ser Pro Asn His Gly Ser
1               5                   10                  15

Gly His Arg Pro Tyr Asn Tyr
            20

<210> SEQ ID NO 212
<211> LENGTH: 12
<212> TYPE: PRT
<213> ORGANISM: Vicugna pacos

<400> SEQUENCE: 212

Val Ala Val Thr Phe Thr Thr Pro Arg Ser Asp Tyr
1               5                   10

<210> SEQ ID NO 213
<211> LENGTH: 8
<212> TYPE: PRT
<213> ORGANISM: Vicugna pacos

<400> SEQUENCE: 213

Gly Gly Gly Trp Arg Pro Gly Ala
1               5

<210> SEQ ID NO 214
<211> LENGTH: 8
<212> TYPE: PRT
<213> ORGANISM: Vicugna pacos

<400> SEQUENCE: 214

Asn Arg Glu Thr Met Pro Pro Phe
1               5

<210> SEQ ID NO 215

```
<211> LENGTH: 12
<212> TYPE: PRT
<213> ORGANISM: Vicugna pacos

<400> SEQUENCE: 215

Gly Tyr Ala Arg Leu Ile Ala Asp Ser Asp Leu Val
1               5                   10

<210> SEQ ID NO 216
<211> LENGTH: 12
<212> TYPE: PRT
<213> ORGANISM: Vicugna pacos

<400> SEQUENCE: 216

Gly Tyr Ala Arg Leu Met Thr Asp Ser Glu Leu Val
1               5                   10

<210> SEQ ID NO 217
<211> LENGTH: 11
<212> TYPE: PRT
<213> ORGANISM: Vicugna pacos

<400> SEQUENCE: 217

Trp Gly Gln Gly Thr Gln Val Thr Val Ser Ser
1               5                   10

<210> SEQ ID NO 218
<211> LENGTH: 11
<212> TYPE: PRT
<213> ORGANISM: Vicugna pacos

<400> SEQUENCE: 218

Trp Gly Pro Gly Thr Gln Val Thr Val Ser Ser
1               5                   10

<210> SEQ ID NO 219
<211> LENGTH: 11
<212> TYPE: PRT
<213> ORGANISM: Vicugna pacos

<400> SEQUENCE: 219

Trp Gly Gln Gly Thr Gln Val Thr Val Ser Ser
1               5                   10

<210> SEQ ID NO 220
<211> LENGTH: 11
<212> TYPE: PRT
<213> ORGANISM: Vicugna pacos

<400> SEQUENCE: 220

Trp Gly Gln Gly Thr Gln Val Thr Val Ser Ser
1               5                   10

<210> SEQ ID NO 221
<211> LENGTH: 11
<212> TYPE: PRT
<213> ORGANISM: Vicugna pacos

<400> SEQUENCE: 221

Trp Gly Gln Gly Thr Gln Val Thr Val Ser Ser
1               5                   10

<210> SEQ ID NO 222
<211> LENGTH: 11
<212> TYPE: PRT
```

<210> SEQ ID NO 222
<211> LENGTH: 11
<212> TYPE: PRT
<213> ORGANISM: Vicugna pacos

<400> SEQUENCE: 222

Trp Gly Gln Gly Thr Gln Val Thr Val Ser Ser
1               5                   10

<210> SEQ ID NO 223
<211> LENGTH: 11
<212> TYPE: PRT
<213> ORGANISM: Vicugna pacos

<400> SEQUENCE: 223

Trp Gly Gln Gly Thr Gln Val Thr Val Ser Ser
1               5                   10

<210> SEQ ID NO 224
<211> LENGTH: 11
<212> TYPE: PRT
<213> ORGANISM: Vicugna pacos

<400> SEQUENCE: 224

Trp Gly Gln Gly Ile Gln Val Thr Val Ser Ser
1               5                   10

<210> SEQ ID NO 225
<211> LENGTH: 11
<212> TYPE: PRT
<213> ORGANISM: Vicugna pacos

<400> SEQUENCE: 225

Trp Gly Gln Gly Thr Gln Val Thr Val Ser Ser
1               5                   10

<210> SEQ ID NO 226
<211> LENGTH: 11
<212> TYPE: PRT
<213> ORGANISM: Vicugna pacos

<400> SEQUENCE: 226

Trp Gly Gln Gly Thr Gln Val Thr Val Ser Ser
1               5                   10

<210> SEQ ID NO 227
<211> LENGTH: 11
<212> TYPE: PRT
<213> ORGANISM: Vicugna pacos

<400> SEQUENCE: 227

Trp Gly Gln Gly Thr Gln Val Thr Val Ser Ser
1               5                   10

<210> SEQ ID NO 228
<211> LENGTH: 11
<212> TYPE: PRT
<213> ORGANISM: Vicugna pacos

<400> SEQUENCE: 228

Trp Gly Gln Gly Thr Gln Val Thr Val Ser Ser
1               5                   10

<210> SEQ ID NO 229
<211> LENGTH: 11
<212> TYPE: PRT
<213> ORGANISM: Vicugna pacos

<400> SEQUENCE: 229

Trp Gly Gln Gly Thr Gln Val Thr Val Ser Ser
1               5                   10

<210> SEQ ID NO 230
<211> LENGTH: 11
<212> TYPE: PRT
<213> ORGANISM: Vicugna pacos

<400> SEQUENCE: 230

Trp Gly Gln Gly Thr Gln Val Thr Val Ser Ser
1               5                   10

<210> SEQ ID NO 231
<211> LENGTH: 11
<212> TYPE: PRT
<213> ORGANISM: Vicugna pacos

<400> SEQUENCE: 231

Trp Gly Gln Gly Thr Gln Val Thr Val Ser Ser
1               5                   10

<210> SEQ ID NO 232
<211> LENGTH: 11
<212> TYPE: PRT
<213> ORGANISM: Vicugna pacos

<400> SEQUENCE: 232

Trp Gly Gln Gly Thr Gln Val Thr Val Ser Ser
1               5                   10

<210> SEQ ID NO 233
<211> LENGTH: 11
<212> TYPE: PRT
<213> ORGANISM: Vicugna pacos

<400> SEQUENCE: 233

Trp Gly Gln Gly Thr Gln Val Thr Val Ser Ser
1               5                   10

<210> SEQ ID NO 234
<211> LENGTH: 11
<212> TYPE: PRT
<213> ORGANISM: Vicugna pacos

<400> SEQUENCE: 234

Trp Gly Gln Gly Thr Gln Val Thr Val Ser Ser
1               5                   10

<210> SEQ ID NO 235
<211> LENGTH: 11
<212> TYPE: PRT
<213> ORGANISM: Vicugna pacos

<400> SEQUENCE: 235

Trp Gly Gln Gly Thr Gln Val Thr Val Ser Ser
1               5                   10

<210> SEQ ID NO 236
<211> LENGTH: 11
<212> TYPE: PRT
<213> ORGANISM: Vicugna pacos

<400> SEQUENCE: 236

Trp Gly Gln Gly Thr Gln Val Thr Val Ser Ser
1               5                   10

<210> SEQ ID NO 237
<211> LENGTH: 11
<212> TYPE: PRT
<213> ORGANISM: Vicugna pacos

<400> SEQUENCE: 237

Trp Gly Gln Gly Thr Gln Val Thr Val Ser Ser
1               5                   10

<210> SEQ ID NO 238
<211> LENGTH: 11
<212> TYPE: PRT
<213> ORGANISM: Vicugna pacos

<400> SEQUENCE: 238

Trp Gly Gln Gly Thr Gln Val Thr Val Ser Ser
1               5                   10

<210> SEQ ID NO 239
<211> LENGTH: 11
<212> TYPE: PRT
<213> ORGANISM: Vicugna pacos

<400> SEQUENCE: 239

Trp Gly Gln Gly Thr Gln Val Thr Val Ser Ser
1               5                   10

<210> SEQ ID NO 240
<211> LENGTH: 11
<212> TYPE: PRT
<213> ORGANISM: Vicugna pacos

<400> SEQUENCE: 240

Trp Gly Lys Gly Thr Gln Val Thr Val Ser Ser
1               5                   10

<210> SEQ ID NO 241
<211> LENGTH: 11
<212> TYPE: PRT
<213> ORGANISM: Vicugna pacos

<400> SEQUENCE: 241

Trp Gly Gln Gly Thr Gln Val Thr Val Ser Ser
1               5                   10

<210> SEQ ID NO 242
<211> LENGTH: 11
<212> TYPE: PRT
<213> ORGANISM: Vicugna pacos

<400> SEQUENCE: 242

Trp Gly Arg Gly Thr Gln Val Thr Val Ser Ser
1               5                   10

<210> SEQ ID NO 243
<211> LENGTH: 11
<212> TYPE: PRT
<213> ORGANISM: Vicugna pacos

<400> SEQUENCE: 243

Trp Gly Gln Gly Thr Gln Val Thr Val Ser Ser
1               5                   10

<210> SEQ ID NO 244
<211> LENGTH: 11
<212> TYPE: PRT
<213> ORGANISM: Vicugna pacos

<400> SEQUENCE: 244

Arg Gly Gln Gly Thr Gln Val Thr Val Ser Ser
1               5                   10

<210> SEQ ID NO 245
<211> LENGTH: 11
<212> TYPE: PRT
<213> ORGANISM: Vicugna pacos

<400> SEQUENCE: 245

Arg Gly Gln Gly Thr Gln Val Thr Val Ser Ser
1               5                   10

<210> SEQ ID NO 246
<211> LENGTH: 11
<212> TYPE: PRT
<213> ORGANISM: Vicugna pacos

<400> SEQUENCE: 246

Arg Gly Gln Gly Thr Gln Val Thr Val Ser Ser
1               5                   10

<210> SEQ ID NO 247
<211> LENGTH: 125
<212> TYPE: PRT
<213> ORGANISM: Artificial Sequence
<220> FEATURE:
<223> OTHER INFORMATION: Anti-mouse MMR Nanobody clone 1

<400> SEQUENCE: 247

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ile Phe Ser Ile Asn
            20                  25                  30

Ala Ile Gly Trp Tyr Arg Gln Ala Pro Gly Lys Gln Arg Glu Leu Val
        35                  40                  45

Ala Thr Ile Thr Leu Ser Gly Ser Thr Asn Tyr Ala Asp Ser Val Lys
    50                  55                  60

Gly Arg Phe Ser Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asn Thr Tyr Ser Asp Ser Asp Val Tyr Gly Tyr Trp Gly Gln Gly
            100                 105                 110

Thr Gln Val Thr Val Ser Ser His His His His His
        115                 120                 125

<210> SEQ ID NO 248
<211> LENGTH: 10
<212> TYPE: PRT
<213> ORGANISM: Artificial Sequence
<220> FEATURE:
<223> OTHER INFORMATION: Linker sequence

<400> SEQUENCE: 248

Gly Ser Gly Ser Gly Ser Gly Ser Gly Ser

```
                1               5                  10

<210> SEQ ID NO 249
<211> LENGTH: 20
<212> TYPE: PRT
<213> ORGANISM: Artificial Sequence
<220> FEATURE:
<223> OTHER INFORMATION: Linker sequence

<400> SEQUENCE: 249

Gly Ser Gly Ser Gly Ser Gly Ser Gly Ser Gly Ser Gly Ser Gly Ser
1               5                   10                  15

Gly Ser Gly Ser
            20

<210> SEQ ID NO 250
<211> LENGTH: 15
<212> TYPE: PRT
<213> ORGANISM: Artificial Sequence
<220> FEATURE:
<223> OTHER INFORMATION: Linker sequence

<400> SEQUENCE: 250

Gly Gly Gly Gly Ser Gly Gly Gly Gly Ser Gly Gly Gly Gly Ser
1               5                   10                  15

<210> SEQ ID NO 251
<211> LENGTH: 17
<212> TYPE: PRT
<213> ORGANISM: Artificial Sequence
<220> FEATURE:
<223> OTHER INFORMATION: Linker sequence

<400> SEQUENCE: 251

Ala His His Ser Glu Asp Pro Ser Ser Lys Ala Pro Lys Ala Pro Met
1               5                   10                  15

Ala

<210> SEQ ID NO 252
<211> LENGTH: 16
<212> TYPE: PRT
<213> ORGANISM: Artificial Sequence
<220> FEATURE:
<223> OTHER INFORMATION: Linker sequence

<400> SEQUENCE: 252

Ser Pro Ser Thr Pro Pro Thr Pro Ser Pro Ser Thr Pro Pro Ala Ser
1               5                   10                  15

<210> SEQ ID NO 253
<211> LENGTH: 4
<212> TYPE: PRT
<213> ORGANISM: Artificial Sequence
<220> FEATURE:
<223> OTHER INFORMATION: Factor Xa cleavage site

<400> SEQUENCE: 253

Ile Glu Gly Arg
1

<210> SEQ ID NO 254
<211> LENGTH: 4
<212> TYPE: PRT
<213> ORGANISM: Artificial Sequence
<220> FEATURE:
<223> OTHER INFORMATION: thrombin cleavage site
```

<400> SEQUENCE: 254

Leu Val Pro Arg
1

<210> SEQ ID NO 255
<211> LENGTH: 5
<212> TYPE: PRT
<213> ORGANISM: Artificial Sequence
<220> FEATURE:
<223> OTHER INFORMATION: enterokinase cleaving site

<400> SEQUENCE: 255

Asp Asp Asp Asp Lys
1               5

<210> SEQ ID NO 256
<211> LENGTH: 8
<212> TYPE: PRT
<213> ORGANISM: Artificial Sequence
<220> FEATURE:
<223> OTHER INFORMATION: PreScission cleavage site

<400> SEQUENCE: 256

Leu Glu Val Leu Phe Gln Gly Pro
1               5

<210> SEQ ID NO 257
<211> LENGTH: 22
<212> TYPE: DNA
<213> ORGANISM: Artificial Sequence
<220> FEATURE:
<223> OTHER INFORMATION: leader sequence specific CALL001

<400> SEQUENCE: 257
gtcctggctc tcttctacaa gg                                          22

<210> SEQ ID NO 258
<211> LENGTH: 23
<212> TYPE: DNA
<213> ORGANISM: Artificial Sequence
<220> FEATURE:
<223> OTHER INFORMATION: CH2 exon specific CALL002

<400> SEQUENCE: 258
ggtacgtgct gttgaactgt tcc                                         23

<210> SEQ ID NO 259
<211> LENGTH: 29
<212> TYPE: DNA
<213> ORGANISM: Artificial Sequence
<220> FEATURE:
<223> OTHER INFORMATION: primer A6E

<400> SEQUENCE: 259
gatgtgcagc tgcaggagtc tggrggagg                                   29

<210> SEQ ID NO 260
<211> LENGTH: 34
<212> TYPE: DNA
<213> ORGANISM: Artificial Sequence
<220> FEATURE:
<223> OTHER INFORMATION: primer PMCF

<400> SEQUENCE: 260
ctagtgcggc cgctgaggag acggtgacct gggt                             34

```
<210> SEQ ID NO 261
<211> LENGTH: 10
<212> TYPE: PRT
<213> ORGANISM: Artificial Sequence
<220> FEATURE:
<223> OTHER INFORMATION: HA tag

<400> SEQUENCE: 261

Tyr Pro Tyr Asp Val Pro Asp Tyr Gly Ser
1               5                   10

<210> SEQ ID NO 262
<211> LENGTH: 19
<212> TYPE: PRT
<213> ORGANISM: Artificial Sequence
<220> FEATURE:
<223> OTHER INFORMATION: HA and 6xHis tag

<400> SEQUENCE: 262

Ala Ala Ala Tyr Pro Tyr Asp Val Pro Asp Tyr Gly Ser His His His
1               5                   10                  15

His His His
```